(12) United States Patent
Deleersnijder et al.

(10) Patent No.: US 7,083,965 B2
(45) Date of Patent: Aug. 1, 2006

(54) HUMAN ENZYMES OF THE METALLOPROTEASE FAMILY

(75) Inventors: Willy Deleersnijder, Weesp (NL); Rico Wiegers, Weesp (NL); Michael Weske, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 0 days.

(21) Appl. No.: 10/870,003

(22) Filed: Jun. 18, 2004

(65) Prior Publication Data

US 2004/0224356 A1 Nov. 11, 2004

Related U.S. Application Data

(60) Division of application No. 10/147,928, filed on May 20, 2002, which is a continuation of application No. PCT/EP00/11532, filed on Nov. 17, 2000, now Pat. No. 6,855,532.

(30) Foreign Application Priority Data

| Nov. 19, 1999 | (EP) | ................................. 99203862 |
| Nov. 19, 1999 | (NL) | ................................. 1013616 |
| May 13, 2000 | (NL) | ................................. 1015356 |
| May 31, 2000 | (EP) | ................................. 00201937 |

(51) Int. Cl.
*C12N 9/64* (2006.01)
*C12N 1/20* (2006.01)
*C12N 5/06* (2006.01)
*C12N 5/00* (2006.01)
*C07H 21/04* (2006.01)

(52) U.S. Cl. .................... 435/226; 536/23.2; 536/23.1; 536/23.5; 424/94.67; 435/320.1; 435/69.1; 435/325; 435/348; 435/410; 435/254.1; 435/252.3

(58) Field of Classification Search ................ 435/226, 435/69.1, 320.1, 325, 348, 410, 254.1; 424/94.67; 536/23.2, 23.1, 23.5
See application file for complete search history.

(56) References Cited

FOREIGN PATENT DOCUMENTS

| CA | WO 00/57750 | * | 8/2000 |
| FR | EP 1069188 A1 | * | 1/2001 |

OTHER PUBLICATIONS

Bonvouloir N. et al. Molecular Cloning, Tissue Distribution, and Chromosome Localization of MMEL2, a Gene Coding for a Novel Human Member of the Neutral Endopeptidase-24.11 Family, DNA and Cell Biology, 2001, 20, 493-498.*

* cited by examiner

*Primary Examiner*—Rebecca E. Prouty
*Assistant Examiner*—Malgorzata A. Walicka
(74) *Attorney, Agent, or Firm*—Crowell & Moring LLP

(57) ABSTRACT

This invention relates to newly identified polypeptides which have zinc metalloprotease activities and are referred to as IGS5, and polynucleotides encoding such polypeptides, to their use in therapy and in identifying compounds which may be stimulators and/or inhibitors which are useful in therapy, and to production of such polypeptides and polynucleotides.

6 Claims, 10 Drawing Sheets

```
         StuI       start        POMC SIGNAL SEQUENCE
     GACAAGGCCT ATTATGCCGA GATCGTGCTG CAGCCGCTCG
     CTGTTCCGGA TAATACGGCT CTAGCACGAC GTCGGCGAGC GGGGCCCTGT TGCTGGCCTT GCTGCTTCAA* GCCTCCATGG
     CCCCGGGACA ACGACCGGAA CGACGAAGTT CGGAGGTACC GS linker         His6
     AAGTGCGTGG CGGTTCTCAC CATCACCACC ATCACAGCGA
     TTCACGCACC GCCAAGAGTG GTAGTGGTGG TAGTGTCGCT GGTCTGCACC ACCCCTGGCT GCGTGATAGC AGCTGCCAGG
     CCAGACGTGG TGGGGACCGA CGCACTATCG TCGACGGTCC ATCCTCCAGA ACATGGACCC
     TAGGAGGTCT TGTACCTGGG
     HuIGS5 overlapping sequence
```

FIG.4.

GSHHHHHHSEVCTTPGCVIAAARILQNMDPTTEPCDDFYQFACGGWLRRHVIPETNS
RYSIFDVLRDELEVIL<u>KAVLE</u>N<u>STAKD</u>RPAVEKARTL<u>YRSCM</u>N<u>QSVIE</u>KRGSQPLLD
ILEVVGGWPV<u>AMDRW</u>N<u>ETVGL</u>EWELERQLALMNSQFNRRVLIDLFI<u>WNDDQ</u>N<u>SSRHI</u>
IYIDQPTLGMPSREYYFNGGSNRKVREAYLQFMVSVATLLREDANLPRDSCLVQEDM
MQVLELETQLAKATVPQEERHDVIALYHRMGLEELQSQF<u>GLKGF</u>N<u>WTLFI</u>QTVLSSV
KIKLLPDEEVVVYGIPYLQNLENIIDTYSARTIQNYLVWRLVLDRIGSLSQRFKDTR
VNYRKALFGTMVEEVRWRECVGYVNSNMENAVGSLYVREAFPGDSKSMVRELIDKVR
TVFVETLDELGWMDEESKKKAQEKAMSIREQIGHPDYILEEMNRRLDEE<u>YSNL</u>N<u>FSE</u>
<u>DL</u>YFENSLQNLKVGAQRSLRKLREKVDPNLWIIGAAVVNAFYSPNRNQIVFPAGILQ
PPFFSKEQPQALNFGGIGMVIGHEITHGFDDNGRNFDKNGNM<u>MDWWS</u>N<u>FSTQH</u>FREQ
SECM<u>IYQYG</u>N<u>YSWDL</u>ADEQNVNGFNTLGENIADNGGVRQAYKAYLKWMAEGGKDQQL
PGLDLTHEQLFFINYAQVWCGSYRPEFAIQSIKTDVHSPLKYRVLGSLQNLAAFADT
FHCARGTPMHPKERCRVW

FIG.6.

| Lane | Sample | DTT |
|---|---|---|
| I.1 | Prestained Marker | + |
| 2 | Start before pretreatment | + |
| 3 | Start after pretreatment | + |
| 4 | Flow through | + |
| 5 | Prestained Marker | + |
| 6 | / | |
| II.1 | Prestained Marker | + |
| 2 | Pool 1 500mM MMP-eluate | + |
| 3 | Pool 2 " | + |
| 4 | Pool 3 " | + |
| 5 | Pool 4 " | + |
| 6 | Prestained Marker | + |

| Lane | Sample | DTT |
|---|---|---|
| 1 | Prestained Marker (Gibco) | + |
| 2 | Start crude | + |
| 3 | Start Lentil | + |
| 4 | Flow through Lentil | + |
| 5 | 500mM MMP Lentil-eluate (Pool 1) | + |
| 6 | 500mM MMP Lentil-eluate (Pool 2) | + |
| 7 | 500mM MMP Lentil-eluate (Pool 3) | + |
| 8 | 200mM imidazole IMAC-eluaat (< Pool 1) | + |
| 9 | 200mM imidazole IMAC-eluaat (< Pool 2) | + |
| 10 | 200mM pool after dialysis | + |
| 11 | 200mM pool after dialysis | - |
| 12 | Prestained Marker (Gibco) | + |
| 13 | Prestained Marker (Pierce) | + |

| Lane | Sample | DTT |
|---|---|---|
| III.1 | Prestained Marker | + |
| 2 | Flow through | + |
| 3 | 20mM Pool | + |
| 4 | 50mM Pool | + |
| 5 | 100mM Pool | + |
| 6 | 200mM Pool | + |

SEQUENCE LISTING

```
<160> NUMBER OF SEQ ID NOS: 31

<210> SEQ ID NO 1
<211> LENGTH: 2076
<212> TYPE: DNA
<213> ORGANISM: Homo sapiens
<220> FEATURE:
<221> NAME/KEY: CDS
<222> LOCATION: (1)..(2073)

<400> SEQUENCE: 1 tgc acc acc cct ggc tgc gtg ata gca gct gcc agg atc ctc cag aac        48
Cys Thr Thr Pro Gly Cys Val Ile Ala Ala Ala Arg Ile Leu Gln Asn
 1               5                  10                  15 atg gac ccg acc acg gaa ccg tgt gac gac ttc tac cag ttt gca tgc        96
Met Asp Pro Thr Thr Glu Pro Cys Asp Asp Phe Tyr Gln Phe Ala Cys
             20                  25                  30 gga ggc tgg ctg cgg cgc cac gtg atc cct gag acc aac tca aga tac       144
Gly Gly Trp Leu Arg Arg His Val Ile Pro Glu Thr Asn Ser Arg Tyr
         35                  40                  45 agc atc ttt gac gtc ctc cgc gac gag ctg gag gtc atc ctc aaa gcg       192
Ser Ile Phe Asp Val Leu Arg Asp Glu Leu Glu Val Ile Leu Lys Ala
     50                  55                  60 gtg ctg gag aat tcg act gcc aag gac cgg ccg gct gtg gag aag gcc       240
Val Leu Glu Asn Ser Thr Ala Lys Asp Arg Pro Ala Val Glu Lys Ala
 65                  70                  75                  80 agg acg ctg tac cgc tcc tgc atg aac cag agt gtg ata gag aag cga       288
Arg Thr Leu Tyr Arg Ser Cys Met Asn Gln Ser Val Ile Glu Lys Arg
                 85                  90                  95 ggc tct cag ccc ctg ctg gac atc ttg gag gtg gtg gga ggc tgg ccg       336
Gly Ser Gln Pro Leu Leu Asp Ile Leu Glu Val Val Gly Gly Trp Pro
            100                 105                 110
```

| | | |
|---|---|---|
| gtg gcg atg gac agg tgg aac gag acc gta gga ctc gag tgg gag ctg<br>Val Ala Met Asp Arg Trp Asn Glu Thr Val Gly Leu Glu Trp Glu Leu<br>              115                    120                    125 | 384 |
| gag cgg cag ctg gcg ctg atg aac tca cag ttc aac agg cgc gtc ctc<br>Glu Arg Gln Leu Ala Leu Met Asn Ser Gln Phe Asn Arg Arg Val Leu<br>130                    135                    140 | 432 |
| atc gac ctc ttc atc tgg aac gac gac cag aac tcc agc cgg cac atc<br>Ile Asp Leu Phe Ile Trp Asn Asp Asp Gln Asn Ser Ser Arg His Ile<br>145                    150                    155                    160 | 480 |
| atc tac ata gac cag ccc acc ttg ggc atg ccc tcc cga gag tac tac<br>Ile Tyr Ile Asp Gln Pro Thr Leu Gly Met Pro Ser Arg Glu Tyr Tyr<br>              165                    170                    175 | 528 |
| ttc aac ggc ggc agc aac cgg aag gtg cgg gaa gcc tac ctg cag ttc<br>Phe Asn Gly Gly Ser Asn Arg Lys Val Arg Glu Ala Tyr Leu Gln Phe<br>                  180                    185                    190 | 576 |
| atg gtg tca gtg gcc acg ttg ctg cgg gag gat gca aac ctg ccc agg<br>Met Val Ser Val Ala Thr Leu Leu Arg Glu Asp Ala Asn Leu Pro Arg<br>              195                    200                    205 | 624 |
| gac agc tgc ctg gtg cag gag gac atg atg cag gtg ctg gag ctg gag<br>Asp Ser Cys Leu Val Gln Glu Asp Met Met Gln Val Leu Glu Leu Glu<br>          210                    215                    220 | 672 |
| aca cag ctg gcc aag gcc acg gta ccc cag gag gag aga cac gac gtc<br>Thr Gln Leu Ala Lys Ala Thr Val Pro Gln Glu Glu Arg His Asp Val<br>225                    230                    235                    240 | 720 |
| atc gcc ttg tac cac cgg atg gga ctg gag gag ctg caa agc cag ttt<br>Ile Ala Leu Tyr His Arg Met Gly Leu Glu Glu Leu Gln Ser Gln Phe<br>              245                    250                    255 | 768 |
| ggc ctg aag gga ttt aac tgg act ctg ttc ata caa act gtg cta tcc<br>Gly Leu Lys Gly Phe Asn Trp Thr Leu Phe Ile Gln Thr Val Leu Ser<br>                  260                    265                    270 | 816 |
| tct gtc aaa atc aag ctg ctg cca gat gag gaa gtg gtg gtc tat ggc<br>Ser Val Lys Ile Lys Leu Leu Pro Asp Glu Glu Val Val Val Tyr Gly<br>              275                    280                    285 | 864 |
| atc ccc tac ctg cag aac ctt gaa aac atc atc gac acc tac tca gcc<br>Ile Pro Tyr Leu Gln Asn Leu Glu Asn Ile Ile Asp Thr Tyr Ser Ala<br>          290                    295                    300 | 912 |
| agg acc ata cag aac tac ctg gtc tgg cgc ctg gtg ctg gac cgc att<br>Arg Thr Ile Gln Asn Tyr Leu Val Trp Arg Leu Val Leu Asp Arg Ile<br>305                    310                    315                    320 | 960 |
| ggt agc cta agc cag aga ttc aag gac aca cga gtg aac tac cgc aag<br>Gly Ser Leu Ser Gln Arg Phe Lys Asp Thr Arg Val Asn Tyr Arg Lys<br>                  325                    330                    335 | 1008 |
| gcg ctg ttt ggc aca atg gtg gag gag gtg cgc tgg cgt gaa tgt gtg<br>Ala Leu Phe Gly Thr Met Val Glu Glu Val Arg Trp Arg Glu Cys Val<br>                  340                    345                    350 | 1056 |
| ggc tac gtc aac agc aac atg gag aac gcc gtg ggc tcc ctc tac gtc<br>Gly Tyr Val Asn Ser Asn Met Glu Asn Ala Val Gly Ser Leu Tyr Val<br>              355                    360                    365 | 1104 |
| agg gag gcg ttc cct gga gac agc aag agc atg gtc aga gaa ctc att<br>Arg Glu Ala Phe Pro Gly Asp Ser Lys Ser Met Val Arg Glu Leu Ile<br>          370                    375                    380 | 1152 |
| gac aag gtg cgg aca gtg ttt gtg gag acg ctg gac gag ctg ggc tgg<br>Asp Lys Val Arg Thr Val Phe Val Glu Thr Leu Asp Glu Leu Gly Trp<br>385                    390                    395                    400 | 1200 |
| atg gac gag gag tcc aag aag aag gcg cag gag aag gcc atg agc atc<br>Met Asp Glu Glu Ser Lys Lys Lys Ala Gln Glu Lys Ala Met Ser Ile<br>                  405                    410                    415 | 1248 |
| cgg gag cag atc ggg cac cct gac tac atc ctg gag gag atg aac agg<br>Arg Glu Gln Ile Gly His Pro Asp Tyr Ile Leu Glu Glu Met Asn Arg<br>                  420                    425                    430 | 1296 |

```
cgc ctg gac gag gag tac tcc aat ctg aac ttc tca gag gac ctg tac    1344
Arg Leu Asp Glu Glu Tyr Ser Asn Leu Asn Phe Ser Glu Asp Leu Tyr
        435                 440                 445 ttt gag aac agt ctg cag aac ctc aag gtg ggc gcc cag cgg agc ctc    1392
Phe Glu Asn Ser Leu Gln Asn Leu Lys Val Gly Ala Gln Arg Ser Leu
    450                 455                 460 agg aag ctt cgg gaa aag gtg gac cca aat ctc tgg atc atc ggg gcg    1440
Arg Lys Leu Arg Glu Lys Val Asp Pro Asn Leu Trp Ile Ile Gly Ala
465                 470                 475                 480 gcg gtg gtc aat gcg ttc tac tcc cca aac cga aac cag att gta ttc    1488
Ala Val Val Asn Ala Phe Tyr Ser Pro Asn Arg Asn Gln Ile Val Phe
                485                 490                 495 cct gcc ggg atc ctc cag ccc ccc ttc ttc agc aag gag cag cca cag    1536
Pro Ala Gly Ile Leu Gln Pro Pro Phe Phe Ser Lys Glu Gln Pro Gln
            500                 505                 510 gcc ttg aac ttt gga ggc att ggg atg gtg atc ggg cac gag atc acg    1584
Ala Leu Asn Phe Gly Gly Ile Gly Met Val Ile Gly His Glu Ile Thr
        515                 520                 525 cac ggc ttt gac gac aat ggc cgg aac ttc gac aag aat ggc aac atg    1632
His Gly Phe Asp Asp Asn Gly Arg Asn Phe Asp Lys Asn Gly Asn Met
    530                 535                 540 atg gat tgg tgg agt aac ttc tcc acc cag cac ttc cgg gag cag tca    1680
Met Asp Trp Trp Ser Asn Phe Ser Thr Gln His Phe Arg Glu Gln Ser
545                 550                 555                 560 gag tgc atg atc tac cag tac ggc aac tac tcc tgg gac ctg gca gac    1728
Glu Cys Met Ile Tyr Gln Tyr Gly Asn Tyr Ser Trp Asp Leu Ala Asp
                565                 570                 575 gaa cag aac gtg aac gga ttc aac acc ctt ggg gaa aac att gct gac    1776
Glu Gln Asn Val Asn Gly Phe Asn Thr Leu Gly Glu Asn Ile Ala Asp
            580                 585                 590 aac gga ggg gtg cgg caa gcc tat aag gcc tac ctc aag tgg atg gca    1824
Asn Gly Gly Val Arg Gln Ala Tyr Lys Ala Tyr Leu Lys Trp Met Ala
        595                 600                 605 gag ggt ggc aag gac cag cag ctg ccc ggc ctg gat ctc acc cat gag    1872
Glu Gly Gly Lys Asp Gln Gln Leu Pro Gly Leu Asp Leu Thr His Glu
    610                 615                 620 cag ctc ttc ttc atc aac tac gcc cag gtg tgg tgc ggg tcc tac cgg    1920
Gln Leu Phe Phe Ile Asn Tyr Ala Gln Val Trp Cys Gly Ser Tyr Arg
625                 630                 635                 640 ccc gag ttc gcc atc caa tcc atc aag aca gac gtc cac agt ccc ctg    1968
Pro Glu Phe Ala Ile Gln Ser Ile Lys Thr Asp Val His Ser Pro Leu
                645                 650                 655 aag tac agg gta ctg ggg tcg ctg cag aac ctg gcc gcc ttc gca gac    2016
Lys Tyr Arg Val Leu Gly Ser Leu Gln Asn Leu Ala Ala Phe Ala Asp
            660                 665                 670 acg ttc cac tgt gcc cgg ggc acc ccc atg cac ccc aag gag cga tgc    2064
Thr Phe His Cys Ala Arg Gly Thr Pro Met His Pro Lys Glu Arg Cys
        675                 680                 685 cgc gtg tgg tag                                                     2076
Arg Val Trp
    690

<210> SEQ ID NO 2
<211> LENGTH: 691
<212> TYPE: PRT
<213> ORGANISM: Homo sapiens

<400> SEQUENCE: 2

Cys Thr Thr Pro Gly Cys Val Ile Ala Ala Ala Arg Ile Leu Gln Asn
 1               5                  10                  15
```

```
Met Asp Pro Thr Thr Glu Pro Cys Asp Asp Phe Tyr Gln Phe Ala Cys
            20                  25                  30
Gly Gly Trp Leu Arg Arg His Val Ile Pro Glu Thr Asn Ser Arg Tyr
        35                  40                  45
Ser Ile Phe Asp Val Leu Arg Asp Glu Leu Glu Val Ile Leu Lys Ala
    50                  55                  60
Val Leu Glu Asn Ser Thr Ala Lys Asp Arg Pro Ala Val Glu Lys Ala
65                  70                  75                  80
Arg Thr Leu Tyr Arg Ser Cys Met Asn Gln Ser Val Ile Glu Lys Arg
                85                  90                  95
Gly Ser Gln Pro Leu Leu Asp Ile Leu Glu Val Val Gly Gly Trp Pro
            100                 105                 110
Val Ala Met Asp Arg Trp Asn Glu Thr Val Gly Leu Glu Trp Glu Leu
            115                 120                 125
Glu Arg Gln Leu Ala Leu Met Asn Ser Gln Phe Asn Arg Arg Val Leu
        130                 135                 140
Ile Asp Leu Phe Ile Trp Asn Asp Asp Gln Asn Ser Ser Arg His Ile
145                 150                 155                 160
Ile Tyr Ile Asp Gln Pro Thr Leu Gly Met Pro Ser Arg Glu Tyr Tyr
                165                 170                 175
Phe Asn Gly Gly Ser Asn Arg Lys Val Arg Glu Ala Tyr Leu Gln Phe
            180                 185                 190
Met Val Ser Val Ala Thr Leu Leu Arg Glu Asp Ala Asn Leu Pro Arg
        195                 200                 205
Asp Ser Cys Leu Val Gln Glu Asp Met Met Gln Val Leu Glu Leu Glu
    210                 215                 220
Thr Gln Leu Ala Lys Ala Thr Val Pro Gln Glu Glu Arg His Asp Val
225                 230                 235                 240
Ile Ala Leu Tyr His Arg Met Gly Leu Glu Glu Leu Gln Ser Gln Phe
                245                 250                 255
Gly Leu Lys Gly Phe Asn Trp Thr Leu Phe Ile Gln Thr Val Leu Ser
            260                 265                 270
Ser Val Lys Ile Lys Leu Leu Pro Asp Glu Glu Val Val Val Tyr Gly
        275                 280                 285
Ile Pro Tyr Leu Gln Asn Leu Glu Asn Ile Ile Asp Thr Tyr Ser Ala
    290                 295                 300
Arg Thr Ile Gln Asn Tyr Leu Val Trp Arg Leu Val Leu Asp Arg Ile
305                 310                 315                 320
Gly Ser Leu Ser Gln Arg Phe Lys Asp Thr Arg Val Asn Tyr Arg Lys
                325                 330                 335
Ala Leu Phe Gly Thr Met Val Glu Glu Val Arg Trp Arg Glu Cys Val
            340                 345                 350
Gly Tyr Val Asn Ser Asn Met Glu Asn Ala Val Gly Ser Leu Tyr Val
        355                 360                 365
Arg Glu Ala Phe Pro Gly Asp Ser Lys Ser Met Val Arg Glu Leu Ile
    370                 375                 380
Asp Lys Val Arg Thr Val Phe Val Glu Thr Leu Asp Glu Leu Gly Trp
385                 390                 395                 400
Met Asp Glu Glu Ser Lys Lys Lys Ala Gln Glu Lys Ala Met Ser Ile
                405                 410                 415
Arg Glu Gln Ile Gly His Pro Asp Tyr Ile Leu Glu Glu Met Asn Arg
            420                 425                 430
```

-continued

```
Arg Leu Asp Glu Glu Tyr Ser Asn Leu Asn Phe Ser Glu Asp Leu Tyr
        435                 440                 445

Phe Glu Asn Ser Leu Gln Asn Leu Lys Val Gly Ala Gln Arg Ser Leu
    450                 455                 460

Arg Lys Leu Arg Glu Lys Val Asp Pro Asn Leu Trp Ile Ile Gly Ala
465                 470                 475                 480

Ala Val Val Asn Ala Phe Tyr Ser Pro Asn Arg Asn Gln Ile Val Phe
                485                 490                 495

Pro Ala Gly Ile Leu Gln Pro Pro Phe Phe Ser Lys Glu Gln Pro Gln
            500                 505                 510

Ala Leu Asn Phe Gly Gly Ile Gly Met Val Ile Gly His Glu Ile Thr
        515                 520                 525

His Gly Phe Asp Asp Asn Gly Arg Asn Phe Asp Lys Asn Gly Asn Met
    530                 535                 540

Met Asp Trp Trp Ser Asn Phe Ser Thr Gln His Phe Arg Glu Gln Ser
545                 550                 555                 560

Glu Cys Met Ile Tyr Gln Tyr Gly Asn Tyr Ser Trp Asp Leu Ala Asp
                565                 570                 575

Glu Gln Asn Val Asn Gly Phe Asn Thr Leu Gly Glu Asn Ile Ala Asp
            580                 585                 590

Asn Gly Gly Val Arg Gln Ala Tyr Lys Ala Tyr Leu Lys Trp Met Ala
        595                 600                 605

Glu Gly Gly Lys Asp Gln Gln Leu Pro Gly Leu Asp Leu Thr His Glu
    610                 615                 620

Gln Leu Phe Phe Ile Asn Tyr Ala Gln Val Trp Cys Gly Ser Tyr Arg
625                 630                 635                 640

Pro Glu Phe Ala Ile Gln Ser Ile Lys Thr Asp Val His Ser Pro Leu
                645                 650                 655

Lys Tyr Arg Val Leu Gly Ser Leu Gln Asn Leu Ala Ala Phe Ala Asp
            660                 665                 670

Thr Phe His Cys Ala Arg Gly Thr Pro Met His Pro Lys Glu Arg Cys
        675                 680                 685

Arg Val Trp
    690

<210> SEQ ID NO 3
<211> LENGTH: 2340
<212> TYPE: DNA
<213> ORGANISM: Homo sapiens
<220> FEATURE:
<221> NAME/KEY: CDS
<222> LOCATION: (1)..(2337)

<400> SEQUENCE: 3 atg ggg aag tcc gaa ggc ccc gtg ggg atg gtg gag agc gct ggc cgt     48
Met Gly Lys Ser Glu Gly Pro Val Gly Met Val Glu Ser Ala Gly Arg
1               5                   10                  15 gca ggg cag aag cgc ccg ggg ttc ctg gag ggg ggg ctg ctg ctg ctg     96
Ala Gly Gln Lys Arg Pro Gly Phe Leu Glu Gly Gly Leu Leu Leu Leu
                20                  25                  30 ctg ctg ctg gtg acc gct gcc ctg gtg gcc ttg ggt gtc ctc tac gcc    144
Leu Leu Leu Val Thr Ala Ala Leu Val Ala Leu Gly Val Leu Tyr Ala
            35                  40                  45 gac cgc aga ggg aag cag ctg cca cgc ctt gct agc cgg ctg tgc ttc    192
Asp Arg Arg Gly Lys Gln Leu Pro Arg Leu Ala Ser Arg Leu Cys Phe
        50                  55                  60 tta cag gag gag agg acc ttt gta aaa cga aaa ccc cga ggg atc cca    240
```

```
Leu Gln Glu Glu Arg Thr Phe Val Lys Arg Lys Pro Arg Gly Ile Pro
 65                  70                  75                  80 gag gcc caa gag gtg agc gag gtc tgc acc acc cct ggc tgc gta ata      288
Glu Ala Gln Glu Val Ser Glu Val Cys Thr Thr Pro Gly Cys Val Ile
                     85                  90                  95 gca gct gcc agg atc ctc cag aac atg gac ccg acc acg gaa ccg tgt      336
Ala Ala Ala Arg Ile Leu Gln Asn Met Asp Pro Thr Thr Glu Pro Cys
                100                 105                 110 gac gac ttc tac cag ttt gca tgc gga ggc tgg ctg cgg cgc cac gtg      384
Asp Asp Phe Tyr Gln Phe Ala Cys Gly Gly Trp Leu Arg Arg His Val
            115                 120                 125 atc cct gag acc aac tca aga tac agc atc ttt gac gtc ctc cgc gac      432
Ile Pro Glu Thr Asn Ser Arg Tyr Ser Ile Phe Asp Val Leu Arg Asp
130                 135                 140 gag ctg gag gtc atc ctc aaa gcg gtg ctg gag aat tcg act gcc aag      480
Glu Leu Glu Val Ile Leu Lys Ala Val Leu Glu Asn Ser Thr Ala Lys
145                 150                 155                 160 gac cgg ccg gct gtg gag aag gcc agg acg ctg tac cgc tcc tgc atg      528
Asp Arg Pro Ala Val Glu Lys Ala Arg Thr Leu Tyr Arg Ser Cys Met
                165                 170                 175 aac cag agt gtg ata gag aag cga ggc tct cag ccc ctg ctg gac atc      576
Asn Gln Ser Val Ile Glu Lys Arg Gly Ser Gln Pro Leu Leu Asp Ile
                180                 185                 190 ttg gag gtg gtg gga ggc tgg ccg gtg gcg atg gac agg tgg aac gag      624
Leu Glu Val Val Gly Gly Trp Pro Val Ala Met Asp Arg Trp Asn Glu
            195                 200                 205 acc gta gga ctc gag tgg gag ctg gag cgg cag ctg gcg ctg atg aac      672
Thr Val Gly Leu Glu Trp Glu Leu Glu Arg Gln Leu Ala Leu Met Asn
210                 215                 220 tca cag ttc aac agg cgc gtc ctc atc gac ctc ttc atc tgg aac gac      720
Ser Gln Phe Asn Arg Arg Val Leu Ile Asp Leu Phe Ile Trp Asn Asp
225                 230                 235                 240 gac cag aac tcc agc cgg cac atc atc tac ata gac cag ccc acc ttg      768
Asp Gln Asn Ser Ser Arg His Ile Ile Tyr Ile Asp Gln Pro Thr Leu
                245                 250                 255 ggc atg ccc tcc cga gag tac tac ttc aac ggc ggc agc aac cgg aag      816
Gly Met Pro Ser Arg Glu Tyr Tyr Phe Asn Gly Gly Ser Asn Arg Lys
                260                 265                 270 gtg cgg gaa gcc tac ctg cag ttc atg gtg tca gtg gcc acg ttg ctg      864
Val Arg Glu Ala Tyr Leu Gln Phe Met Val Ser Val Ala Thr Leu Leu
            275                 280                 285 cgg gag gat gca aac ctg ccc agg gac agc tgc ctg gtg cag gag gac      912
Arg Glu Asp Ala Asn Leu Pro Arg Asp Ser Cys Leu Val Gln Glu Asp
290                 295                 300 atg atg cag gtg ctg gag ctg gag aca cag ctg gcc aag gcc acg gta      960
Met Met Gln Val Leu Glu Leu Glu Thr Gln Leu Ala Lys Ala Thr Val
305                 310                 315                 320 ccc cag gag gag aga cac gac gtc atc gcc ttg tac cac cgg atg gga     1008
Pro Gln Glu Glu Arg His Asp Val Ile Ala Leu Tyr His Arg Met Gly
                325                 330                 335 ctg gag gag ctg caa agc cag ttt ggc ctg aag gga ttt aac tgg act     1056
Leu Glu Glu Leu Gln Ser Gln Phe Gly Leu Lys Gly Phe Asn Trp Thr
            340                 345                 350 ctg ttc ata caa act gtg cta tcc tct gtc aaa atc aag ctg ctg cca     1104
Leu Phe Ile Gln Thr Val Leu Ser Ser Val Lys Ile Lys Leu Leu Pro
355                 360                 365 gat gag gaa gtg gtg gtc tat ggc atc ccc tac ctg cag aac ctt gaa     1152
Asp Glu Glu Val Val Val Tyr Gly Ile Pro Tyr Leu Gln Asn Leu Glu
370                 375                 380
```

```
aac atc atc gac acc tac tca gcc agg acc ata cag aac tac ctg gtc      1200
Asn Ile Ile Asp Thr Tyr Ser Ala Arg Thr Ile Gln Asn Tyr Leu Val
385                 390                 395                 400 tgg cgc ctg gtg ctg gac cgc att ggt agc cta agc cag aga ttc aag      1248
Trp Arg Leu Val Leu Asp Arg Ile Gly Ser Leu Ser Gln Arg Phe Lys
                405                 410                 415 gac aca cga gtg aac tac cgc aag gcg ctg ttt ggc aca atg gtg gag      1296
Asp Thr Arg Val Asn Tyr Arg Lys Ala Leu Phe Gly Thr Met Val Glu
420                 425                 430 gag gtg cgc tgg cgt gaa tgt gtg ggc tac gtc aac agc aac atg gag      1344
Glu Val Arg Trp Arg Glu Cys Val Gly Tyr Val Asn Ser Asn Met Glu
        435                 440                 445 aac gcc gtg ggc tcc ctc tac gtc agg gag gcg ttc cct gga gac agc      1392
Asn Ala Val Gly Ser Leu Tyr Val Arg Glu Ala Phe Pro Gly Asp Ser
450                 455                 460 aag agc atg gtc aga gaa ctc att gac aag gtg cgg aca gtg ttt gtg      1440
Lys Ser Met Val Arg Glu Leu Ile Asp Lys Val Arg Thr Val Phe Val
465                 470                 475                 480 gag acg ctg gac gag ctg ggc tgg atg gac gag gag tcc aag aag aag      1488
Glu Thr Leu Asp Glu Leu Gly Trp Met Asp Glu Glu Ser Lys Lys Lys
                485                 490                 495 gcg cag gag aag gcc atg agc atc cgg gag cag atc ggg cac cct gac      1536
Ala Gln Glu Lys Ala Met Ser Ile Arg Glu Gln Ile Gly His Pro Asp
                500                 505                 510 tac atc ctg gag gag atg aac agg cgc ctg gac gag gag tac tcc aat      1584
Tyr Ile Leu Glu Glu Met Asn Arg Arg Leu Asp Glu Glu Tyr Ser Asn
        515                 520                 525 ctg aac ttc tca gag gac ctg tac ttt gag aac agt ctg cag aac ctc      1632
Leu Asn Phe Ser Glu Asp Leu Tyr Phe Glu Asn Ser Leu Gln Asn Leu
530                 535                 540 aag gtg ggc gcc cag cgg agc ctc agg aag ctt cgg gaa aag gtg gac      1680
Lys Val Gly Ala Gln Arg Ser Leu Arg Lys Leu Arg Glu Lys Val Asp
545                 550                 555                 560 cca aat ctc tgg atc atc ggg gcg gcg gtg gtc aat gcg ttc tac tcc      1728
Pro Asn Leu Trp Ile Ile Gly Ala Ala Val Val Asn Ala Phe Tyr Ser
                565                 570                 575 cca aac cga aac cag att gta ttc cct gcc ggg atc ctc cag ccc ccc      1776
Pro Asn Arg Asn Gln Ile Val Phe Pro Ala Gly Ile Leu Gln Pro Pro
                580                 585                 590 ttc ttc agc aag gag cag cca cag gcc ttg aac ttt gga ggc att ggg      1824
Phe Phe Ser Lys Glu Gln Pro Gln Ala Leu Asn Phe Gly Gly Ile Gly
        595                 600                 605 atg gtg atc ggg cac gag atc acg cac ggc ttt gac gac aat ggc cgg      1872
Met Val Ile Gly His Glu Ile Thr His Gly Phe Asp Asp Asn Gly Arg
610                 615                 620 aac ttc gac aag aat ggc aac atg atg gat tgg tgg agt aac ttc tcc      1920
Asn Phe Asp Lys Asn Gly Asn Met Met Asp Trp Trp Ser Asn Phe Ser
625                 630                 635                 640 acc cag cac ttc cgg gag cag tca gag tgc atg atc tac cag tac ggc      1968
Thr Gln His Phe Arg Glu Gln Ser Glu Cys Met Ile Tyr Gln Tyr Gly
                645                 650                 655 aac tac tcc tgg gac ctg gca gac gaa cag aac gtg aac gga ttc aac      2016
Asn Tyr Ser Trp Asp Leu Ala Asp Glu Gln Asn Val Asn Gly Phe Asn
                660                 665                 670 acc ctt ggg gaa aac att gct gac aac gga ggg gtg cgg caa gcc tat      2064
Thr Leu Gly Glu Asn Ile Ala Asp Asn Gly Gly Val Arg Gln Ala Tyr
        675                 680                 685 aag gcc tac ctc aag tgg atg gca gag ggt ggc aag gac cag cag ctg      2112
Lys Ala Tyr Leu Lys Trp Met Ala Glu Gly Gly Lys Asp Gln Gln Leu
690                 695                 700
```

-continued

```
ccc ggc ctg gat ctc acc cat gag cag ctc ttc ttc atc aac tac gcc      2160
Pro Gly Leu Asp Leu Thr His Glu Gln Leu Phe Phe Ile Asn Tyr Ala
705                 710                 715                 720 cag gtg tgg tgc ggg tcc tac cgg ccc gag ttc gcc atc caa tcc atc      2208
Gln Val Trp Cys Gly Ser Tyr Arg Pro Glu Phe Ala Ile Gln Ser Ile
            725                 730                 735 aag aca gac gtc cac agt ccc ctg aag tac agg gta ctg ggg tcg ctg      2256
Lys Thr Asp Val His Ser Pro Leu Lys Tyr Arg Val Leu Gly Ser Leu
        740                 745                 750 cag aac ctg gcc gcc ttc gca gac acg ttc cac tgt gcc cgg ggc acc      2304
Gln Asn Leu Ala Ala Phe Ala Asp Thr Phe His Cys Ala Arg Gly Thr
    755                 760                 765 ccc atg cac ccc aag gag cga tgc cgc gtg tgg tag                      2340
Pro Met His Pro Lys Glu Arg Cys Arg Val Trp
770                 775
```

<210> SEQ ID NO 4
<211> LENGTH: 779
<212> TYPE: PRT
<213> ORGANISM: Homo sapiens

<400> SEQUENCE: 4

```
Met Gly Lys Ser Glu Gly Pro Val Gly Met Val Glu Ser Ala Gly Arg
1               5                   10                  15

Ala Gly Gln Lys Arg Pro Gly Phe Leu Glu Gly Gly Leu Leu Leu Leu
            20                  25                  30

Leu Leu Leu Val Thr Ala Ala Leu Val Ala Leu Gly Val Leu Tyr Ala
        35                  40                  45

Asp Arg Arg Gly Lys Gln Leu Pro Arg Leu Ala Ser Arg Leu Cys Phe
    50                  55                  60

Leu Gln Glu Glu Arg Thr Phe Val Lys Arg Lys Pro Arg Gly Ile Pro
65                  70                  75                  80

Glu Ala Gln Glu Val Ser Glu Val Cys Thr Thr Pro Gly Cys Val Ile
                85                  90                  95

Ala Ala Ala Arg Ile Leu Gln Asn Met Asp Pro Thr Thr Glu Pro Cys
            100                 105                 110

Asp Asp Phe Tyr Gln Phe Ala Cys Gly Gly Trp Leu Arg Arg His Val
        115                 120                 125

Ile Pro Glu Thr Asn Ser Arg Tyr Ser Ile Phe Asp Val Leu Arg Asp
    130                 135                 140

Glu Leu Glu Val Ile Leu Lys Ala Val Leu Glu Asn Ser Thr Ala Lys
145                 150                 155                 160

Asp Arg Pro Ala Val Glu Lys Ala Arg Thr Leu Tyr Arg Ser Cys Met
                165                 170                 175

Asn Gln Ser Val Ile Glu Lys Arg Gly Ser Gln Pro Leu Leu Asp Ile
            180                 185                 190

Leu Glu Val Val Gly Gly Trp Pro Val Ala Met Asp Arg Trp Asn Glu
        195                 200                 205

Thr Val Gly Leu Glu Trp Glu Leu Glu Arg Gln Leu Ala Leu Met Asn
    210                 215                 220

Ser Gln Phe Asn Arg Arg Val Leu Ile Asp Leu Phe Ile Trp Asn Asp
225                 230                 235                 240

Asp Gln Asn Ser Ser Arg His Ile Ile Tyr Ile Asp Gln Pro Thr Leu
                245                 250                 255

Gly Met Pro Ser Arg Glu Tyr Tyr Phe Asn Gly Gly Ser Asn Arg Lys
            260                 265                 270
```

```
Val Arg Glu Ala Tyr Leu Gln Phe Met Val Ser Val Ala Thr Leu Leu
        275                 280                 285

Arg Glu Asp Ala Asn Leu Pro Arg Asp Ser Cys Leu Val Gln Glu Asp
        290                 295                 300

Met Met Gln Val Leu Glu Leu Glu Thr Gln Leu Ala Lys Ala Thr Val
305                 310                 315                 320

Pro Gln Glu Glu Arg His Asp Val Ile Ala Leu Tyr His Arg Met Gly
            325                 330                 335

Leu Glu Glu Leu Gln Ser Gln Phe Gly Leu Lys Gly Phe Asn Trp Thr
                340                 345                 350

Leu Phe Ile Gln Thr Val Leu Ser Ser Val Lys Ile Lys Leu Leu Pro
        355                 360                 365

Asp Glu Glu Val Val Val Tyr Gly Ile Pro Tyr Leu Gln Asn Leu Glu
        370                 375                 380

Asn Ile Ile Asp Thr Tyr Ser Ala Arg Thr Ile Gln Asn Tyr Leu Val
385                 390                 395                 400

Trp Arg Leu Val Leu Asp Arg Ile Gly Ser Leu Ser Gln Arg Phe Lys
            405                 410                 415

Asp Thr Arg Val Asn Tyr Arg Lys Ala Leu Phe Gly Thr Met Val Glu
            420                 425                 430

Glu Val Arg Trp Arg Glu Cys Val Gly Tyr Val Asn Ser Asn Met Glu
        435                 440                 445

Asn Ala Val Gly Ser Leu Tyr Val Arg Glu Ala Phe Pro Gly Asp Ser
        450                 455                 460

Lys Ser Met Val Arg Glu Leu Ile Asp Lys Val Arg Thr Val Phe Val
465                 470                 475                 480

Glu Thr Leu Asp Glu Leu Gly Trp Met Asp Glu Ser Lys Lys Lys
            485                 490                 495

Ala Gln Glu Lys Ala Met Ser Ile Arg Glu Gln Ile Gly His Pro Asp
        500                 505                 510

Tyr Ile Leu Glu Glu Met Asn Arg Arg Leu Asp Glu Glu Tyr Ser Asn
            515                 520                 525

Leu Asn Phe Ser Glu Asp Leu Tyr Phe Glu Asn Ser Leu Gln Asn Leu
530                 535                 540

Lys Val Gly Ala Gln Arg Ser Leu Arg Lys Leu Arg Glu Lys Val Asp
545                 550                 555                 560

Pro Asn Leu Trp Ile Ile Gly Ala Ala Val Val Asn Ala Phe Tyr Ser
            565                 570                 575

Pro Asn Arg Asn Gln Ile Val Phe Pro Ala Gly Ile Leu Gln Pro Pro
        580                 585                 590

Phe Phe Ser Lys Glu Gln Pro Gln Ala Leu Asn Phe Gly Gly Ile Gly
        595                 600                 605

Met Val Ile Gly His Glu Ile Thr His Gly Phe Asp Asp Asn Gly Arg
        610                 615                 620

Asn Phe Asp Lys Asn Gly Asn Met Met Asp Trp Trp Ser Asn Phe Ser
625                 630                 635                 640

Thr Gln His Phe Arg Glu Gln Ser Glu Cys Met Ile Tyr Gln Tyr Gly
            645                 650                 655

Asn Tyr Ser Trp Asp Leu Ala Asp Glu Gln Asn Val Asn Gly Phe Asn
            660                 665                 670

Thr Leu Gly Glu Asn Ile Ala Asp Asn Gly Gly Val Arg Gln Ala Tyr
        675                 680                 685
```

```
Lys Ala Tyr Leu Lys Trp Met Ala Glu Gly Gly Lys Asp Gln Gln Leu
    690             695                 700

Pro Gly Leu Asp Leu Thr His Glu Gln Leu Phe Phe Ile Asn Tyr Ala
705                 710                 715                 720

Gln Val Trp Cys Gly Ser Tyr Arg Pro Glu Phe Ala Ile Gln Ser Ile
                725                 730                 735

Lys Thr Asp Val His Ser Pro Leu Lys Tyr Arg Val Leu Gly Ser Leu
                740                 745                 750

Gln Asn Leu Ala Ala Phe Ala Asp Thr Phe His Cys Ala Arg Gly Thr
                755                 760                 765

Pro Met His Pro Lys Glu Arg Cys Arg Val Trp
770                 775

<210> SEQ ID NO 5
<211> LENGTH: 2262
<212> TYPE: DNA
<213> ORGANISM: Homo sapiens
<220> FEATURE:
<221> NAME/KEY: CDS
<222> LOCATION: (1)..(2259)

<400> SEQUENCE: 5 atg ggg aag tcc gaa ggc cca gtg ggg atg gtg gag agc gcc ggc cgt    48
Met Gly Lys Ser Glu Gly Pro Val Gly Met Val Glu Ser Ala Gly Arg
1               5                   10                  15 gca ggg cag aag cgc ccg ggg ttc ctg gag ggg ggg ctg ctg ctg ctg    96
Ala Gly Gln Lys Arg Pro Gly Phe Leu Glu Gly Gly Leu Leu Leu Leu
                20                  25                  30 ctg ctg ctg gtg acc gct gcc ctg gtg gcc ttg ggt gtc ctc tac gcc   144
Leu Leu Leu Val Thr Ala Ala Leu Val Ala Leu Gly Val Leu Tyr Ala
            35                  40                  45 gac cgc aga ggg atc cca gag gcc caa gag gtg agc gag gtc tgc acc   192
Asp Arg Arg Gly Ile Pro Glu Ala Gln Glu Val Ser Glu Val Cys Thr
        50                  55                  60 acc cct ggc tgc gtg ata gca gct gcc agg atc ctc cag aac atg gac   240
Thr Pro Gly Cys Val Ile Ala Ala Ala Arg Ile Leu Gln Asn Met Asp
65                  70                  75                  80 ccg acc acg gaa ccg tgt gac gac ttc tac cag ttt gca tgc gga ggc   288
Pro Thr Thr Glu Pro Cys Asp Asp Phe Tyr Gln Phe Ala Cys Gly Gly
                85                  90                  95 tgg ctg cgg cgc cac gtg atc cct gag acc aac tca aga tac agc atc   336
Trp Leu Arg Arg His Val Ile Pro Glu Thr Asn Ser Arg Tyr Ser Ile
                100                 105                 110 ttt gac gtc ctc cgc gac gag ctg gag gtc atc ctc aaa gcg gtg ctg   384
Phe Asp Val Leu Arg Asp Glu Leu Glu Val Ile Leu Lys Ala Val Leu
            115                 120                 125 gag aat tcg act gcc aag gac cgg ccg gct gtg gag aag gcc agg acg   432
Glu Asn Ser Thr Ala Lys Asp Arg Pro Ala Val Glu Lys Ala Arg Thr
        130                 135                 140 ctg tac cgc tcc tgc atg aac cag agt gtg ata gag aag cga ggc tct   480
Leu Tyr Arg Ser Cys Met Asn Gln Ser Val Ile Glu Lys Arg Gly Ser
145                 150                 155                 160 cag ccc ctg ctg gac atc ttg gag gtg gtg gga ggc tgg ccg gtg gcg   528
Gln Pro Leu Leu Asp Ile Leu Glu Val Val Gly Gly Trp Pro Val Ala
                165                 170                 175 atg gac agg tgg aac gag acc gta gga ctc gag tgg gag ctg gag cgg   576
Met Asp Arg Trp Asn Glu Thr Val Gly Leu Glu Trp Glu Leu Glu Arg
                180                 185                 190 cag ctg gcg ctg atg aac tca cag ttc aac agg cgc gtc ctc atc gac   624
Gln Leu Ala Leu Met Asn Ser Gln Phe Asn Arg Arg Val Leu Ile Asp
```

```
                195                 200                 205
ctc ttc atc tgg aac gac gac cag aac tcc agc cgg cac atc atc tac      672
Leu Phe Ile Trp Asn Asp Asp Gln Asn Ser Ser Arg His Ile Ile Tyr
    210                 215                 220 ata gac cag ccc acc ttg ggc atg ccc tcc cga gag tac tac ttc aac      720
Ile Asp Gln Pro Thr Leu Gly Met Pro Ser Arg Glu Tyr Tyr Phe Asn
225                 230                 235                 240 ggc ggc agc aac cgg aag gtg cgg gaa gcc tac ctg cag ttc atg gtg      768
Gly Gly Ser Asn Arg Lys Val Arg Glu Ala Tyr Leu Gln Phe Met Val
                245                 250                 255 tca gtg gcc acg ttg ctg cgg gag gat gca aac ctg ccc agg gac agc      816
Ser Val Ala Thr Leu Leu Arg Glu Asp Ala Asn Leu Pro Arg Asp Ser
            260                 265                 270 tgc ctg gtg cag gag gac atg atg cag gtg ctg gag ctg gag aca cag      864
Cys Leu Val Gln Glu Asp Met Met Gln Val Leu Glu Leu Glu Thr Gln
        275                 280                 285 ctg gcc aag gcc acg gta ccc cag gag gag aga cac gac gtc atc gcc      912
Leu Ala Lys Ala Thr Val Pro Gln Glu Glu Arg His Asp Val Ile Ala
    290                 295                 300 ttg tac cac cgg atg gga ctg gag gag ctg caa agc cag ttt ggc ctg      960
Leu Tyr His Arg Met Gly Leu Glu Glu Leu Gln Ser Gln Phe Gly Leu
305                 310                 315                 320 aag gga ttt aac tgg act ctg ttc ata caa act gtg cta tcc tct gtc     1008
Lys Gly Phe Asn Trp Thr Leu Phe Ile Gln Thr Val Leu Ser Ser Val
                325                 330                 335 aaa atc aag ctg ctg cca gat gag gaa gtg gtg gtc tat ggc atc ccc     1056
Lys Ile Lys Leu Leu Pro Asp Glu Glu Val Val Val Tyr Gly Ile Pro
            340                 345                 350 tac ctg cag aac ctt gaa aac atc atc gac acc tac tca gcc agg acc     1104
Tyr Leu Gln Asn Leu Glu Asn Ile Ile Asp Thr Tyr Ser Ala Arg Thr
        355                 360                 365 ata cag aac tac ctg gtc tgg cgc ctg gtg ctg gac cgc att ggt agc     1152
Ile Gln Asn Tyr Leu Val Trp Arg Leu Val Leu Asp Arg Ile Gly Ser
    370                 375                 380 cta agc cag aga ttc aag gac aca cga gtg aac tac cgc aag gcg ctg     1200
Leu Ser Gln Arg Phe Lys Asp Thr Arg Val Asn Tyr Arg Lys Ala Leu
385                 390                 395                 400 ttt ggc aca atg gtg gag gag gtg cgc tgg cgt gaa tgt gtg ggc tac     1248
Phe Gly Thr Met Val Glu Glu Val Arg Trp Arg Glu Cys Val Gly Tyr
                405                 410                 415 gtc aac agc aac atg gag aac gcc gtg ggc tcc ctc tac gtc agg gag     1296
Val Asn Ser Asn Met Glu Asn Ala Val Gly Ser Leu Tyr Val Arg Glu
            420                 425                 430 gcg ttc cct gga gac agc aag agc atg gtc aga gaa ctc att gac aag     1344
Ala Phe Pro Gly Asp Ser Lys Ser Met Val Arg Glu Leu Ile Asp Lys
        435                 440                 445 gtg cgg aca gtg ttt gtg gag acg ctg gac gag ctg ggc tgg atg gac     1392
Val Arg Thr Val Phe Val Glu Thr Leu Asp Glu Leu Gly Trp Met Asp
    450                 455                 460 gag gag tcc aag aag aag gcg cag gag aag gcc atg agc atc cgg gag     1440
Glu Glu Ser Lys Lys Lys Ala Gln Glu Lys Ala Met Ser Ile Arg Glu
465                 470                 475                 480 cag atc ggg cac cct gac tac atc ctg gag gag atg aac agg cgc ctg     1488
Gln Ile Gly His Pro Asp Tyr Ile Leu Glu Glu Met Asn Arg Arg Leu
                485                 490                 495 gac gag gag tac tcc aat ctg aac ttc tca gag gac ctg tac ttt gag     1536
Asp Glu Glu Tyr Ser Asn Leu Asn Phe Ser Glu Asp Leu Tyr Phe Glu
            500                 505                 510 aac agt ctg cag aac ctc aag gtg ggc gcc cag cgg agc ctc agg aag     1584
```

-continued

| | | |
|---|---|---|
| Asn Ser Leu Gln Asn Leu Lys Val Gly Ala Gln Arg Ser Leu Arg Lys<br>515 520 525 | | |
| ctt cgg gaa aag gtg gac cca aat ctc tgg atc atc ggg gcg gcg gtg<br>Leu Arg Glu Lys Val Asp Pro Asn Leu Trp Ile Ile Gly Ala Ala Val<br>530 535 540 | 1632 | |
| gtc aat gcg ttc tac tcc cca aac cga aac cag att gta ttc cct gcc<br>Val Asn Ala Phe Tyr Ser Pro Asn Arg Asn Gln Ile Val Phe Pro Ala<br>545 550 555 560 | 1680 | |
| ggg atc ctc cag ccc ccc ttc ttc agc aag gag cag cca cag gcc ttg<br>Gly Ile Leu Gln Pro Pro Phe Phe Ser Lys Glu Gln Pro Gln Ala Leu<br>565 570 575 | 1728 | |
| aac ttt gga ggc att ggg atg gtg atc ggg cac gag atc acg cac ggc<br>Asn Phe Gly Gly Ile Gly Met Val Ile Gly His Glu Ile Thr His Gly<br>580 585 590 | 1776 | |
| ttt gac gac aat ggc cgg aac ttc gac aag aat ggc aac atg atg gat<br>Phe Asp Asp Asn Gly Arg Asn Phe Asp Lys Asn Gly Asn Met Met Asp<br>595 600 605 | 1824 | |
| tgg tgg agt aac ttc tcc acc cag cac ttc cgg gag cag tca gag tgc<br>Trp Trp Ser Asn Phe Ser Thr Gln His Phe Arg Glu Gln Ser Glu Cys<br>610 615 620 | 1872 | |
| atg atc tac cag tac ggc aac tac tcc tgg gac ctg gca gac gaa cag<br>Met Ile Tyr Gln Tyr Gly Asn Tyr Ser Trp Asp Leu Ala Asp Glu Gln<br>625 630 635 640 | 1920 | |
| aac gtg aac gga ttc aac acc ctt ggg gaa aac att gct gac aac gga<br>Asn Val Asn Gly Phe Asn Thr Leu Gly Glu Asn Ile Ala Asp Asn Gly<br>645 650 655 | 1968 | |
| ggg gtg cgg caa gcc tat aag gcc tac ctc aag tgg atg gca gag ggt<br>Gly Val Arg Gln Ala Tyr Lys Ala Tyr Leu Lys Trp Met Ala Glu Gly<br>660 665 670 | 2016 | |
| ggc aag gac cag cag ctg ccc ggc ctg gat ctc acc cat gag cag ctc<br>Gly Lys Asp Gln Gln Leu Pro Gly Leu Asp Leu Thr His Glu Gln Leu<br>675 680 685 | 2064 | |
| ttc ttc atc aac tac gcc cag gtg tgg tgc ggg tcc tac cgg ccc gag<br>Phe Phe Ile Asn Tyr Ala Gln Val Trp Cys Gly Ser Tyr Arg Pro Glu<br>690 695 700 | 2112 | |
| ttc gcc atc caa tcc atc aag aca gac gtc cac agt ccc ctg aag tac<br>Phe Ala Ile Gln Ser Ile Lys Thr Asp Val His Ser Pro Leu Lys Tyr<br>705 710 715 720 | 2160 | |
| agg gta ctg ggg tcg ctg cag aac ctg gcc gcc ttc gca gac acg ttc<br>Arg Val Leu Gly Ser Leu Gln Asn Leu Ala Ala Phe Ala Asp Thr Phe<br>725 730 735 | 2208 | |
| cac tgt gcc cgg ggc acc ccc atg cac ccc aag gag cga tgc cgc gtg<br>His Cys Ala Arg Gly Thr Pro Met His Pro Lys Glu Arg Cys Arg Val<br>740 745 750 | 2256 | |
| tgg tag<br>Trp | 2262 | |

<210> SEQ ID NO 6
<211> LENGTH: 753
<212> TYPE: PRT
<213> ORGANISM: Homo sapiens

<400> SEQUENCE: 6

Met Gly Lys Ser Glu Gly Pro Val Gly Met Val Glu Ser Ala Gly Arg
1               5                   10                  15

Ala Gly Gln Lys Arg Pro Gly Phe Leu Glu Gly Gly Leu Leu Leu Leu
                20                  25                  30

Leu Leu Leu Val Thr Ala Ala Leu Val Ala Leu Gly Val Leu Tyr Ala
            35                  40                  45

```
Asp Arg Arg Gly Ile Pro Glu Ala Gln Glu Val Ser Glu Val Cys Thr
 50                  55                  60

Thr Pro Gly Cys Val Ile Ala Ala Ala Arg Ile Leu Gln Asn Met Asp
 65                  70                  75                  80

Pro Thr Thr Glu Pro Cys Asp Asp Phe Tyr Gln Phe Ala Cys Gly Gly
                 85                  90                  95

Trp Leu Arg Arg His Val Ile Pro Glu Thr Asn Ser Arg Tyr Ser Ile
                100                 105                 110

Phe Asp Val Leu Arg Asp Glu Leu Glu Val Ile Leu Lys Ala Val Leu
                115                 120                 125

Glu Asn Ser Thr Ala Lys Asp Arg Pro Ala Val Glu Lys Ala Arg Thr
    130                 135                 140

Leu Tyr Arg Ser Cys Met Asn Gln Ser Val Ile Glu Lys Arg Gly Ser
145                 150                 155                 160

Gln Pro Leu Leu Asp Ile Leu Glu Val Gly Gly Trp Pro Val Ala
                165                 170                 175

Met Asp Arg Trp Asn Glu Thr Val Gly Leu Glu Trp Glu Leu Glu Arg
                180                 185                 190

Gln Leu Ala Leu Met Asn Ser Gln Phe Asn Arg Val Leu Ile Asp
                195                 200                 205

Leu Phe Ile Trp Asn Asp Asp Gln Asn Ser Ser Arg His Ile Ile Tyr
    210                 215                 220

Ile Asp Gln Pro Thr Leu Gly Met Pro Ser Arg Glu Tyr Tyr Phe Asn
225                 230                 235                 240

Gly Gly Ser Asn Arg Lys Val Arg Glu Ala Tyr Leu Gln Phe Met Val
                245                 250                 255

Ser Val Ala Thr Leu Leu Arg Glu Asp Ala Asn Leu Pro Arg Asp Ser
                260                 265                 270

Cys Leu Val Gln Glu Asp Met Met Gln Val Leu Glu Leu Glu Thr Gln
                275                 280                 285

Leu Ala Lys Ala Thr Val Pro Gln Glu Glu Arg His Asp Val Ile Ala
    290                 295                 300

Leu Tyr His Arg Met Gly Leu Glu Glu Leu Gln Ser Phe Gly Leu
305                 310                 315                 320

Lys Gly Phe Asn Trp Thr Leu Phe Ile Gln Thr Val Leu Ser Ser Val
                325                 330                 335

Lys Ile Lys Leu Leu Pro Asp Glu Val Val Val Tyr Gly Ile Pro
                340                 345                 350

Tyr Leu Gln Asn Leu Glu Asn Ile Ile Asp Thr Tyr Ser Ala Arg Thr
    355                 360                 365

Ile Gln Asn Tyr Leu Val Trp Arg Leu Val Leu Asp Arg Ile Gly Ser
    370                 375                 380

Leu Ser Gln Arg Phe Lys Asp Thr Arg Val Asn Tyr Arg Lys Ala Leu
385                 390                 395                 400

Phe Gly Thr Met Val Glu Val Arg Trp Arg Glu Cys Val Gly Tyr
                405                 410                 415

Val Asn Ser Asn Met Glu Asn Ala Val Gly Ser Leu Tyr Val Arg Glu
                420                 425                 430

Ala Phe Pro Gly Asp Ser Lys Ser Met Val Arg Glu Leu Ile Asp Lys
                435                 440                 445

Val Arg Thr Val Phe Val Glu Thr Leu Asp Glu Leu Gly Trp Met Asp
    450                 455                 460

Glu Glu Ser Lys Lys Lys Ala Gln Glu Lys Ala Met Ser Ile Arg Glu
```

-continued

```
                465                 470                 475                 480
        Gln Ile Gly His Pro Asp Tyr Ile Leu Glu Glu Met Asn Arg Arg Leu
                        485                 490                 495
        Asp Glu Glu Tyr Ser Asn Leu Asn Phe Ser Glu Asp Leu Tyr Phe Glu
                        500                 505                 510
        Asn Ser Leu Gln Asn Leu Lys Val Gly Ala Gln Arg Ser Leu Arg Lys
                        515                 520                 525
        Leu Arg Glu Lys Val Asp Pro Asn Leu Trp Ile Ile Gly Ala Ala Val
                        530                 535                 540
        Val Asn Ala Phe Tyr Ser Pro Asn Arg Asn Gln Ile Val Phe Pro Ala
        545                 550                 555                 560
        Gly Ile Leu Gln Pro Pro Phe Phe Ser Lys Glu Gln Pro Gln Ala Leu
                        565                 570                 575
        Asn Phe Gly Gly Ile Gly Met Val Ile Gly His Glu Ile Thr His Gly
                        580                 585                 590
        Phe Asp Asp Asn Gly Arg Asn Phe Asp Lys Asn Gly Asn Met Met Asp
                        595                 600                 605
        Trp Trp Ser Asn Phe Ser Thr Gln His Phe Arg Glu Gln Ser Glu Cys
                        610                 615                 620
        Met Ile Tyr Gln Tyr Gly Asn Tyr Ser Trp Asp Leu Ala Asp Glu Gln
        625                 630                 635                 640
        Asn Val Asn Gly Phe Asn Thr Leu Gly Glu Asn Ile Ala Asp Asn Gly
                        645                 650                 655
        Gly Val Arg Gln Ala Tyr Lys Ala Tyr Leu Lys Trp Met Ala Glu Gly
                        660                 665                 670
        Gly Lys Asp Gln Gln Leu Pro Gly Leu Asp Leu Thr His Glu Gln Leu
                        675                 680                 685
        Phe Phe Ile Asn Tyr Ala Gln Val Trp Cys Gly Ser Tyr Arg Pro Glu
                        690                 695                 700
        Phe Ala Ile Gln Ser Ile Lys Thr Asp Val His Ser Pro Leu Lys Tyr
        705                 710                 715                 720
        Arg Val Leu Gly Ser Leu Gln Asn Leu Ala Ala Phe Ala Asp Thr Phe
                        725                 730                 735
        His Cys Ala Arg Gly Thr Pro Met His Pro Lys Glu Arg Cys Arg Val
                        740                 745                 750
        Trp

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Reverse
      Primer

<400> SEQUENCE: 7
acacggcatc gctccttg                                                        18

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Degenerated
      Forward Primer

<400> SEQUENCE: 8
```

```
cccctggac ggtgaaygcn twyta                                          25
```

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Reverse
      Primer

<400> SEQUENCE: 9

```
aatccgttca cgttctgttc gtctgcc                                       27
```

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Degenerated
      Forward Primer

<400> SEQUENCE: 10

```
cctggaggag ctgvhntgga tgra                                          24
```

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Adaptor
      Primer

<400> SEQUENCE: 11

```
ccatcctaat acgactcact atagggc                                       27
```

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 12

```
gtccttgcca ccctctgcca tcc                                           23
```

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 13

```
accaccccg ccccgatgat ccagag                                         26
```

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Specific
      Anti-Sense Primer/Reverse Oligonucleotide Primer

<400> SEQUENCE: 14

```
acagccggct agcaaggcgt ggcagctg                                      28
```

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Specific
      Anti-Sense Primer

<400> SEQUENCE: 15
acgacagccg gctagcaagg cgtggcag                                28

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Degenerated
      Forward Primer

<400> SEQUENCE: 16
ggnctsatgg tnctsctsct scts                                    24

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Specific
      Forward Primer

<400> SEQUENCE: 17
ctcctgagtg agcaaaggtt cc                                      22

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Specific
      Reverse Primer

<400> SEQUENCE: 18
gcaaactggt agaagtcgtc acac                                    24

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 19
gacaaggcct attatgccga gatcgtgctg cagccgctcg                   40

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 20
aaggccagca acagggcccc cgagcggctg cagcacgatc                   40

<210> SEQ ID NO 21
<211> LENGTH: 40
<212> TYPE: DNA

```
<213> ORGANISM: Artificial Sequence
<220> FEATURE:
<223> OTHER INFORMATION: Description of Artificial Sequence: Primer

<400> SEQUENCE: 21
ggggccctgt tgctggcctt gctgcttcaa gcctccatgg                    40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 22
gtgagaaccg ccacgcactt ccatggaggc ttgaagcagc                    40

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 23
aagtgcgtgg cggttctcac catcaccacc atcacagcga                    40

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 24
agccaggggt ggtgcagacc tcgctgtgat ggtggtgatg                    40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 25
ggtctgcacc acccctggct gcgtgatagc agctgccagg                    40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 26
gggtccatgt tctggaggat cctggcagct gctatcacgc                    40

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 27
gacaaggcct attatg                                              16
```

```
<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 28
gggtccatgt tctg                                                          14

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 29
agcgaggtct gcac                                                          14

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 30
gtagatgatg tgccg                                                         15

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 31
gcactagtct tggctaccac acgcggcatc gctccttg                                38
```

HUMAN ENZYMES OF THE METALLOPROTEASE FAMILY

CROSS REFERENCE TO RELATED APPLICATIONS

The present application is a divisional application of U.S. application Ser. No. 10/147,928 filed May 20, 2002, now U.S. Pat. No. 6,855,532, which is a continuation of international patent application no. PCT/EP00/11532, filed Nov. 17, 2000, designating the United States of America, the entire disclosure of which is incorporated herein by reference. Priority is claimed based on European patent application no. 99 20 3862.0, filed Nov. 19, 1999; Dutch patent application no. 1013616, filed Nov. 19, 1999; European application no. 00201937.0, filed May 31, 2001; and Dutch patent application no. 1015356, filed May 31, 2000.

FIELD OF THE INVENTION

This invention relates to newly identified polypeptides and polynucleotides encoding such polypeptides, to their use in therapy and in identifying compounds which may be stimulators and/or inhibitors which are potentially useful in therapy, and to production of such polypeptides and polynucleotides. More particularly, the polypeptides and polynucleotides of the present invention relate to enzymes which are members of the metalloprotease family of polypeptides or of other structurally and functionally related polypeptides. These enzymes are hereinafter referred to as IGS5. The invention also relates to inhibiting or stimulating/activating the action of such polypeptides and polynucleotides, to a vector containing said polynucleotides and to a host cell containing such vector. The invention further relates to a method for screening compounds capable of stimulating or inhibiting said IGS5 enzymes.

BACKGROUND OF THE INVENTION

The drug discovery process is currently undergoing a fundamental revolution as it embraces "functional genomics," that is, high throughput genome- or gene-based biology. This approach as a means to identify genes and gene products as therapeutic targets is rapidly superceding earlier approaches based on "positional cloning." A phenotype, such as a biological function or genetic disease, would be identified and this would then be tracked back to the responsible gene, based on its genetic map position.

Functional genomics relies heavily on high-throughput DNA sequencing technologies and various tools of bioinformatics to identify gene sequences of potential interest from the many molecular biology databases now available. There is a continuing need to identify and characterize further genes and their related polypeptides/proteins, as targets for drug discovery.

Among the polypeptides of interest in drug discovery there are metalloproteases and other structurally and functionally related enzymes. Several diseases have been identified where metalloproteases play a critical role in the pathology of the disease. For example, a number of zinc metalloproteases or other structurally and functionally related enzymes have been identified and characterized in the state of the art, and it has become apparent that the participation of these enzymes, e.g. zinc metalloproteases, plays a role in a diverse array of biological functions encompassing both normal and disease situations. Zinc metalloproteases are subset of such enzymes whose catalytic functions are critically dependent on the zinc ion at the active site. This group of enzymes, which comprises various families classified on the basis of both sequence and structural information, are for example described to be intimately involved in such processes as embryonic development, cartilage and bone formation, processing of peptide hormones, reproduction, cardiovascular diseases, arthritis and cancer. Already active site-directed inhibitors of some of the zinc metalloproteases are being used therapeutically as e.g. antihypertensives.

On the basis of sequence and structural information around the zinc binding site of the zinc metalloproteases these enzymes may be classified into several families which may be further classified into superfamilies such as the "metzincins" (astacin, serratia, reprolysin, matrixin), the "gluzincins" (thermolysin, neprilysin, angiotensin converting enzyme, aminopeptidase), or the "zincins" comprising the superfamilies of metzincins and gluzincins. Such grouping not only aids in the elucidation of common catalytic and biosynthetic processing mechanisms, but also is invaluable in elucidating the function(s) of newly identified proteins which possess similar zinc binding motifs. Some individual examples of metalloproteases, e.g. zinc enzymes, already identified in the state of the art comprise neprilysin, endothelin converting enzyme, angiotensin converting enzyme, thermolysin, aminopeptidase, astacin, serratia, reprolysin, matrixin, insulinase, carboxypeptidase and DD-carboxypeptidase.

From the above evidence based on the state of the art it is apparent that metalloproteases and other structurally and functionally related enzymes play key roles in health and disease. Thus there is a continued need to further uncover important functions and potential therapeutic applications for this group of enzymes and to provide novel metalloproteases with the subsequent development of novel synthetic stimulators (activators) or inhibitors, which can help provide new treatments for a variety of diseases of socio-economic importance.

SUMMARY OF THE INVENTION

In one aspect, the present invention relates to IGS5, in particular to IGS5 polypeptides and IGS5 polynucleotides, preferably those related to the human species, to recombinant materials and methods for their production.

In another aspect, the invention relates to methods for using such polypeptides, polynucleotides and recombinant materials, including the treatment of diseases in which metalloproteases or structurally and functionally related enzymes play a critical role in the pathology.

Examples of diseases, in context of which the use of the polypeptides and polynucleotides of the present invention is thought to be useful, include, but are not limited to: CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation and dyskinesias, such as Huntington's disease or Gilles dela Tourett's syndrome, anorexia, bulimia, stroke, addiction/dependency/craving, sleep disorder, epilepsy, migraine; attention deficit/hyperactivity disorder (ADHD); cardiovascular diseases including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders including irritable bowel syndrome (IBS), inflammatory bowel disease (IBD), gastroesophagal reflux disease (GERD), motility disorders and conditions of delayed gastric emptying, such as postoperative or diabetic gastroparesis, and diabetes, ulcers—e.g. gastric ulcer; diarrhoea; other diseases including osteoporosis; inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus.

In a further aspect, the invention relates to methods for identifying agonists and antagonists or inhibitors using the materials provided by the invention, and treating conditions associated with IGS5 imbalance with the identified compounds.

In a still further aspect, the invention relates to diagnostic assays for detecting diseases associated with inappropriate IGS5 activity or levels.

The Polypeptides of the present invention are in particular of interest in the context of cardiovascular diseases.

BRIEF DESCRIPTION OF THE DRAWINGS

FIG. 4 Sequence of the 180 bp fragment, encoding the POMC signal sequence, the Gly-Ser linker, the His6 tag and the start of the IGS5 ectodomain sequence, assembled by overlap PCR using different oligonucleotides. (*silent mutation (bp 57 of the pomc signal sequence)).

FIG. 6 Predicted protein sequence of the mature recombinant soluble His-tagged human IGS5, as expressed in Sf9 cells upon infection with recombinant baculovirus IGBV73 (after cleavage of the 26AA long POMC signal sequence). Potential N-glycosylation sites are underlined.

Detection was performed with anti-His antibody (21E1B4EPR300, Innogenetics, 1 μg/ml final concentration). Second antibody was rabbit anti mouse-Alkaline Phosphatase conjugated (Sigma A-1902). Revelation of the bands was done with NBT-BCIP. Mr marker is the Biolabs broad range MW marker (catno7707S).

Figure 8:
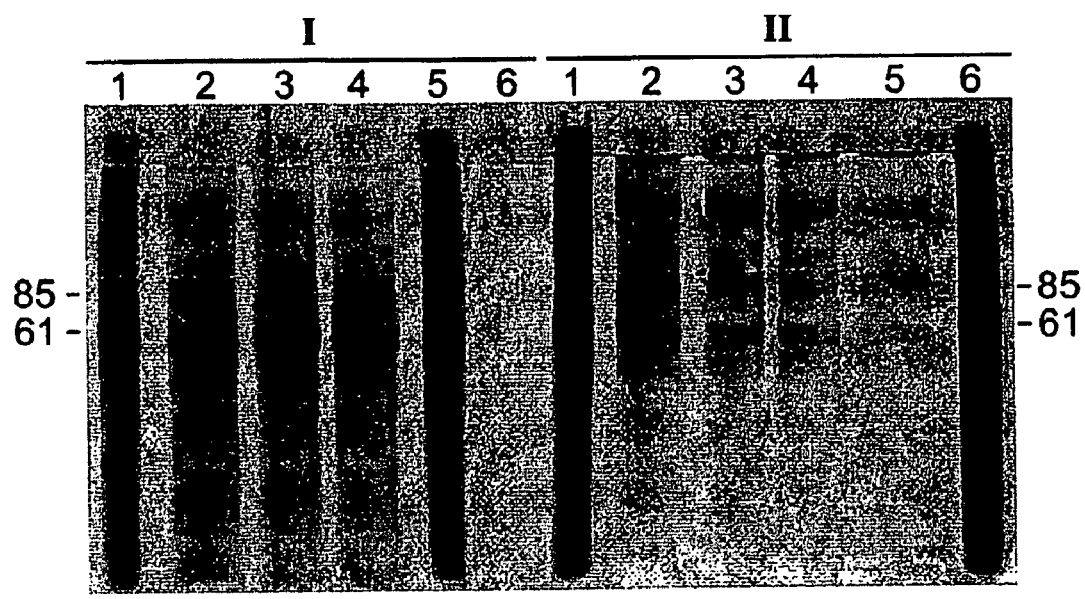

FIG. 8 SDS PAGE analysis under reducing conditions (+DTT) on 12.5% PHASTgel (Pharmacia; 4 μl/slot) of the Lentil chromatography steps. Proteins were visualised by silver staining.

Figure 9:
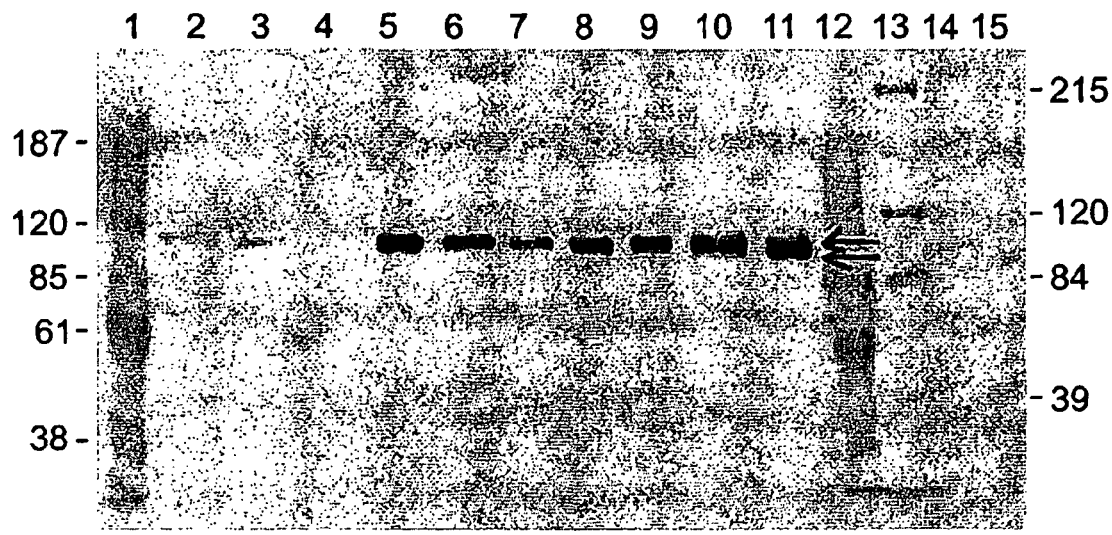

FIG. 9 Western blot analysis of IGS5 at different stages of the purification procedure. Samples were separated on a 7.5% Minigel (Biorad MINI-Protean II) and analyzed via Western blot using the anti His6 primary mab 21E1B4, followed by an alkaline phosphatase conjugated rabbit anti mouse Ig as a secondary antibody and detection by NBT/BCIP (nitroblue tetrazolium/5-bromo,4-chloro,3-indolylphosphate). The column under DTT (1,4-dithio-DL-threitol) denotes whether the proteins were reduced or not with DTT.

Figure 10:
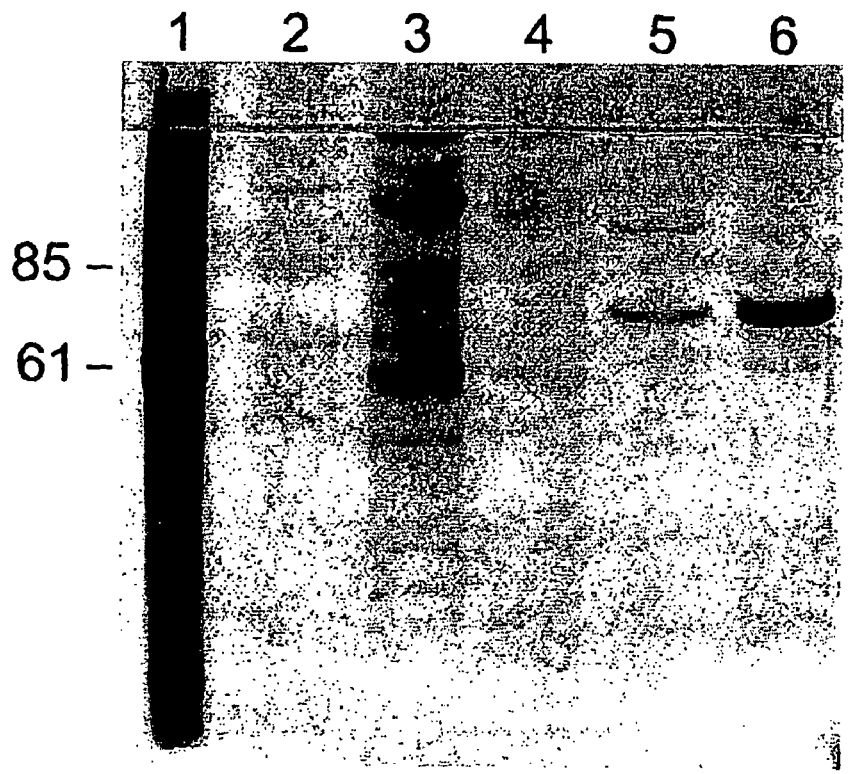

FIG. 10 SDS PAGE analysis under reducing conditions (+DTT) on 12.5% PHASTgel (Pharmacia, 4 μl slots) of different imidazole elution pools of the Zn-IMAC chromatography of pool 1 from the lentil chromatography eluate. Proteins were visualised by silver staining.

DETAILED DESCRIPTION OF THE INVENTION

Definitions

The following definitions are provided to facilitate understanding of certain terms used frequently herein.

"IGS5" refers, among others, to a polypeptide comprising the amino acid sequence set forth in one of SEQ ID NO:2, SEQ ID NO:4 and SEQ ID NO:6, or respective variants thereof. Thus "IGS5" particularly includes IGS5PROT, IGS5PROT1 and IGS5PROT2 (see below).

"Enzyme Activity" or "Biological Activity" refers to the metabolic or physiologic function of said IGS5 or these activities with decreased undesirable side effects. Also included are antigenic and immunogenic activities of said IGS5.

"IGS5-gene" refers to a polynucleotide comprising the nucleotide sequence set forth in one of SEQ ID NO:1, SEQ ID NO:3 and SEQ ID NO:5, or respective variants, e.g. allelic variants, thereof and/or their complements.

"Antibodies" as used herein includes polyclonal and monoclonal antibodies, chimeric, single chain, and humanized antibodies, as well as Fab fragments, including the products of a Fab or other immunoglobulin expression library.

"Isolated" means altered "by the hand of man" from the natural state and/or separated from the natural environment. Thus, if an "isolated" composition or substance that occurs in nature has been "isolated," it has been changed or removed from its original environment, or both. For example, a polynucleotide or a polypeptide naturally present in a living animal is not "isolated," but the same polynucleotide or polypeptide separated from the coexisting materials of its natural state is "isolated," as the term is employed herein.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol; cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, "Proteins—Structure and Molecular Properties," 2nd Ed., T. E. Creighton, W. H. Freeman and Company, New York, 1993; Wold, F., "Post-translational Protein Modifications: Perspectives and Prospects," pp. 1–12 in "Post-translational Covalent Modification of Proteins," B. C. Johnson, Ed., Academic Press, New York, 1983; Seifter et al., "Analysis for protein modifications and nonprotein cofactors," Meth. Enzymol. (1990) 182:626–646; and Rattan et al., "Protein Synthesis: Post-translational Modifications and Aging," Ann. NY Acad. Sci. (1992) 663:48–62).

"Variant" refers to a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known as a measure of identity in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences, e.g. in generally by alignment of the sequences so that the highest order match is obtained. Thus "Identity" and or the alternative wording "Similarity" has an art-recognized meaning and can be readily calculated by known methods, including but not limited to those described in "Computational Molecular Biology," Lesk, A. M., Ed., Oxford University Press, New York, 1988; "Biocomputing: Informatics and Genome Projects," Smith, D. W., Ed., Academic Press, New York, 1993; "Computer Analysis of Sequence Data," Part I, Griffin, A. M., and Griffin, H. G., Eds., Humana Press, New Jersey, 1994; "Sequence Analysis in Molecular Biology," von Heinje, G., Academic Press, 1987; "Sequence Analysis Primer," Gribskov, M. and Devereux, J., Eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403–410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403–410 (1990). The well known Smith Waterman algorithm may also be used to determine identity. A publicly available program useful to determine identity or similarity of polypeptide sequences or polynucleotide sequence, respectively, is known as the "gap" program from Genetics Computer Group, Madison Wis., which is usually run with the default parameters for comparisons (along with no penalty for end gaps). The preferred (i.e. default) parameters for polypeptide sequence comparison include the following: Algorithm as described by Needleman and Wunsch, J. Mol. Biol. 48: 443–453 (1970); Comparison Matrix BLOSSUM62 from Hentikoff and Hentikoff, Proc. Natl. Acad. Sci. USA. 89:10915–10919 (1992); Gap Penalty: 12; Gap Length Penalty: 14. The preferred (i.e. default) parameters for polynucleotide sequence comparison include the following: Algorithm as described by Needleman and Wunsch, J. Mol. Biol. 48: 443–453 (1970); Comparison Matrix: matches=+10, mismatch=0; Gap Penalty: 50; Gap Length Penalty: 3. The word "homology" may substitute for the word "identity."

As an illustration, by a polynucleotide having a nucleotide sequence having at least, for example, 95% "identity" to a reference nucleotide sequence, for example to a reference nucleotid sequence selected from the group of SEQ ID NO:1, SEQ ID NO:3 and SEQ ID NO:5, is intended that the nucleotide sequence of the polynucleotide is identical to the reference sequence except that the polynucleotide sequence may include up to five point mutations per each 100 nucleotides of the respective reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence, or in a number of nucleotides of up to 5% of the total nucleotides in the reference sequence there may be a combination of deletion, insertion and substitution. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example 95% "identity" to a reference amino acid sequence, for example to a reference amino acid sequence selected from the group of SEQ ID NO:2, SEQ ID NO:4 and SEQ ID NO:6, is intended that the amino acid sequence of the polypeptide is identical to the reference sequence except that the polypeptide sequence may include up to five amino acid alterations per each 100 amino acids of the respective reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

"Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared as herein described. Falling within this generic term are the terms "ortholog," meaning a polynucleotide or polypeptide that is the functional equivalent of a polynucleotide or polypeptide in another species, and "paralog" meaning a functionally similar sequence when considered within the same species. Hence, in humans for example, within the family of endothelin converting enzymes ECE-1 is a paralog of the other members, e.g. of ECE-2.

"Fusion protein" refers to a protein encoded by two, often unrelated, fused genes or fragments thereof. This term may be illustrated for example by fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties (see, e.g., EP-A 0232 262). On the other hand, for some uses it would be desirable to be able to delete the Fc part after the fusion protein has been expressed, detected and purified.

Polypeptides of the Invention

The present invention relates to IGS5 polypeptides (or IGS5 enzymes, e.g. to IGS5PROT, IGS5PROT1 or IGS5PROT2, respectively), in particular to human IGS5 polypeptides (or human IGS5 enzymes), and also to IGS5 polypeptide fragments comprising a substantial portion of said entire IGS5 polypeptide. Thus, in a first aspect, the IGS5 polypeptides of the present invention include isolated polypeptides, in particular isolated human species polypeptides, comprising an amino acid sequence which has at least 70% identity, preferably at least 80% and in particular at least 85% identity, more preferably at least 90% identity, yet more preferably at least 95% identity, still more preferably at least 97–99% identity, to one of that selected from the group of SEQ ID NO:2, SEQ ID NO:4 SEQ and SEQ ID NO:6, over the entire length of the respective SEQ ID NO:2, SEQ ID NO:4 SEQ and SEQ ID NO:6. Such polypeptides include those comprising one of the amino acid sequences selected from the group of SEQ ID NO:2, SEQ ID NO:4 SEQ and ID NO:6.

In a second aspect, the IGS5 polypeptides of the present invention include isolated polypeptides, in particular isolated human IGS5 polypeptides, having an amino acid sequence of at least 70% identity, preferably at least 80% and in particular at least 85% identity, more preferably at least 90% identity, yet more preferably at least 95% identity, still more preferably at least 97–99% identity, to one of the amino acid sequences selected from the group of SEQ ID NO:2, SEQ ID NO:4 SEQ and ID NO:6, over the entire length of the respective SEQ ID NO:2, SEQ ID NO:4 SEQ and ID NO:6. Such polypeptides include the IGS5 polypeptide of SEQ ID NO:2, of SEQ ID NO:4 and SEQ ID NO:6, respectively.

Further polypeptides of the present invention include isolated IGS5 polypeptides comprising the sequence contained in one of SEQ ID NO:2, SEQ ID NO:4 SEQ and ID NO:6, and which in particular are human species polypeptides.

Polypeptides of the present invention are members of the metalloprotease family of polypeptides. They are of interest because several dysfunctions, disorders or diseases have been identified where metalloproteases play a critical role in the pathology of the disease. Examples of the diseases, in context of which the polypeptides and polynucleotides of the present invention are thought to be useful, include amongst others: CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation and dyskinesias, such as Huntington's disease or Gilles dela Tourett's syndrome, anorexia, bulimia, stroke, addiction/dependency/craving, sleep disorder, epilepsy, migraine; attention deficit/hyperactivity disorder (ADHD); cardiovascular diseases including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders including irritable bowel syndrome (IBS), inflammatory bowel disease (IBD), gastroesophagal reflux disease (GERD), motility disorders and conditions of delayed gastric emptying, such as post-operative or diabetic gastroparesis, and diabetes, ulcers—e.g. gastric ulcer; diarrhoea; other diseases including osteoporosis; inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus. The Polypeptides of the present invention are in particular of interest in the context of cardiovascular diseases. Furthermore, the IGS5 polypeptides of the invention are also of interest for identifying stimulators or inhibitors of these polypeptides, for providing diagnostic assays for detecting diseases associated with inappropriate IGS5 activity or levels, and for treating conditions associated with IGS5 imbalance with compounds identified to be stimulators or inhibitors. Hence, the IGS5 polypeptides of the invention may be used for designing or screening for selective stimulators or inhibitors, and thus can lead to the development of new drugs. The properties of the IGS5 polypeptides, in particular of the human species IGS5 polypeptides, of the present invention are hereinafter referred to as "IGS5 activity" or "IGS5 polypeptide activity" or "biological activity of IGS5." Also included amongst these activities are antigenic and immunogenic activities of said IGS5 polypeptides, in particular the antigenic and immunogenic activities of one of the polypeptides selected from the group of SEQ ID NO:2, SEQ ID NO:4 SEQ and ID NO:6. Preferably, a polypeptide of the present invention exhibits at least one biological activity of IGS5, preferably of human IGS5.

The IGS5 polypeptides of the present invention may be in the form of a "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr, among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

The present invention furthermore pertains to fragments of the IGS5 polypeptides, in particular to IGS5 polypeptide fragments comprising a substantial portion of the entire IGS5 polypeptide. A fragment is a polypeptide having an amino acid sequence that entirely is the same as part, but not all, of the amino acid sequence of the aforementioned IGS5 polypeptides. As with IGS5 polypeptides, fragments may be "free-standing," or comprised within a larger polypeptide of which they form a part or region, most preferably as a single continuous region.

Preferred fragments include, for example, truncation polypeptides having the amino acid sequence of IGS5 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are these that mediate enzyme activity, including those with a decreased undesirable activity. Also included are those that are antigenic or immunogenic in an animal, especially in a human.

With regard to the variant of the invention pertaining to polypeptide fragments comprising a substantial portion of the entire IGS5 polypeptide as shown in one of SEQ ID NO:2, SEQ ID NO:4 SEQ and ID NO:6, the term "substantial" has the meaning that the fragment of the IGS5 polypeptide has in particular a size of at least about 50 amino acids, preferably a size of at least about 100 amino acids, more preferably a size of at least about 200 amino acids, most preferably a size of at least about 300 amino acids. In this context "about" includes the particularly recited sizes larger or smaller by several, 5, 4, 3, 2 or 1 amino acids. The IGS5 polypeptide fragments according to the invention preferably show at least to some extent at least one of the properties which are characteristic for the IGS5 polypeptides themselves.

With regard to the IGS5 polypeptides of the present invention it was found that they may be involved in the metabolism of biologically active peptides. In particular it was found that these IGS5 polypeptides are metalloprotease type enzymes which may act on a variety of vasoactive peptides. Vasoactive peptides known in the state of the art include atrial natriuretic peptide (ANP), bradykinin, big endothelin (Big ET-1), endothelin (ET-1), substance P, and angiotensin-1 In the context of the present invention it was found that the IGS5 ectodomain, which is a novel human metalloprotease, hydrolyzes e.g. in vitro a variety of said vasoactive peptides including Big ET-1, ET-1, ANP and bradykinin.

Furthermore, the IGS5 metalloprotease type enzymes of the present invention may be inhibited by reference compounds that are used to determine the inhibition properties with regard to enzymes having ECE/NEP-characteristics, e.g. inhibition by compounds such as phosphoramidon. No inhibition of IGS5 is observed for reference compounds that specifically inhibit NEP, e.g. no inhibition of IGS5 by compounds such as thiorphan. Nor any inhibition of IGS5 is observed for reference compounds that specifically inhibit ECE, e.g. no inhibition of IGS5 by compounds such as the selective ECE inhibitor CGS-35066 (De Lombart et al., J. Med. Chem. 2000, Feb. 10; 43(3):488–504). The inhibition data of these reference compounds with regard to the inhibition of the IGS5 metalloprotease type enzymes of the present invention are further described in the experimental part below, in particular in Example 7.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

In another aspect, the present invention relates to IGS5 polynucleotides (e.g. to IGS5DNA, IGS5DNA1 or IGS5DNA2, respectively), in particular to human IGS5 polynucleotides. Such polynucleotides include isolated polynucleotides, preferably isolated human species polynucleotides, comprising a nucleotide sequence encoding a polypeptide which has at least 70% identity, preferably at least 80% and in particular at least 85% identity, more preferably at least 90% identity, yet more preferably at least 95% identity, to one of the amino acid sequences selected from the group of SEQ ID NO:2, SEQ ID NO:4 and SEQ ID NO:6, over the entire length of the respective SEQ ID NO:2, SEQ ID NO:4 or SEQ ID NO:6. In this regard, polynucleotides encoding polypeptides which have at least 97% identity are highly preferred, whilst those with at least 98–99% identity are more highly preferred, and those with at least 99%, in particular 99.9%, identity are most highly preferred. Such polynucleotides include polynucleotides comprising the nucleotide sequence contained in one of the SEQ ID NO:1, SEQ ID NO:3 or SEQ ID NO:5, encoding the respective polypeptide of SEQ ID NO:2, SEQ ID NO:4 or SEQ ID NO:6.

In a variant of this aspect, the polynucleotides of the present invention include isolated polynucleotides, in particular isolated human polynucleotides, comprising a nucleotide sequence that has at least 70% identity, preferably at least 80% and in particular at least 85% identity, more preferably at least 90% identity, yet more preferably at least 95% identity, to a nucleotide sequence encoding one of the polypeptides selected from the group of SEQ ID NO:2, SEQ ID NO:4 and SEQ ID NO:6, over the entire coding region. In this regard, polynucleotides which have at least 97% identity are highly preferred, whilst those with at least 98–99% identity are more highly preferred, and those with at least 99%, in particular 99.9%, identity are most highly preferred.

Further polynucleotides of the present invention include isolated polynucleotides, in particular isolated human polynucleotides, comprising a nucleotide sequence which has at least 70% identity, preferably at least 80% and in particular at least 85% identity, more preferably at least 90% identity, yet more preferably at least 95% identity, to one of the nucleotide sequences selected from the group of SEQ ID NO:1, SEQ ID NO:3 and SEQ ID NO: 5, over the entire length of the respective SEQ ID NO:1, SEQ ID NO:3 or SEQ ID NO:5. Particularly, polynucleotides of the present invention include isolated polynucleotides having a nucleotide sequence of at least 70% identity, preferably at least 80% and in particular at least 85% identity, more preferably at least 90% identity, yet more preferably at least 95% identity, to the respective reference nucleotide sequence over the entire length of the reference nucleotide sequence. In this regard, polynucleotides which comprise or have a nucleotide sequence of at least 97% identity to one of the nucleotide sequences selected from the group of SEQ ID NO:1, SEQ ID NO:3 and SEQ ID NO:5 are highly preferred, whilst those with at least 98–99% identity, are more highly preferred, and those with at least 99%, in particular 99.9%, identity are most highly preferred. Such polynucleotides include a polynucleotides comprising one of the polynucleotides of SEQ ID NO:1, SEQ ID NO:3 or SEQ ID NO:5, as well as the polynucleotides of SEQ ID NO:1, SEQ ID NO:3 or SEQ ID NO:5 themselves, which in particular are human species polynucleotides.

The invention also provides polynucleotides which are complementary to all the above described polynucleotides.

The nucleotide sequence of SEQ ID NO:1 (designated "IGS5DNA") is a cDNA sequence from human origin (*Homo sapiens*) with a length of 2076 nucleotides and comprises a polypeptide encoding sequence (from nucleotide no. 1 to no. 2073) encoding a polypeptide of 691 amino acids, the polypeptide of SEQ ID NO:2 (designated "IGS5PROT"). The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2.

The nucleotide sequence of SEQ ID NO:3 (designated "IGS5DNA1") is a cDNA sequence from human origin (*Homo sapiens*) with a length of 2340 nucleotides (including the stop codon tag) and comprises a polypeptide encoding sequence (from nucleotide no. 1 to no. 2337) encoding a polypeptide of 779 amino acids, the polypeptide of SEQ ID NO:4 (designated "IGS5PROT1"). The nucleotide sequence encoding the polypeptide of SEQ ID NO:4 may be identical to the polypeptide encoding sequence contained in SEQ ID NO:3 or it may be a sequence other than the one contained in SEQ ID NO:3, which, as a result of the redundancy (degeneracy) of the genetic code, also encodes the polypeptide of SEQ ID NO:4.

The nucleotide sequence of SEQ ID NO:5 (designated "IGS5DNA2") is a cDNA sequence from human origin (*Homo sapiens*) with a length of 2262 nucleotides (including the stop codon tag) and comprises a polypeptide encoding sequence (from nucleotide no. 1 to no. 2259) encoding a polypeptide of 753 amino acids, the polypeptide of SEQ ID NO:6 (designated "IGS5PROT2"). The nucleotide sequence encoding the polypeptide of SEQ ID NO:6 may be identical to the polypeptide encoding sequence contained in SEQ ID NO:5 or it may be a sequence other than the one contained in SEQ ID NO:5, which, as a result of the redundancy (degeneracy) of the genetic code, also encodes the polypeptide of SEQ ID NO:6.

The characteristics of the type of polypeptides encoded by the polynucleotides of the invention are described in more detail below.

Biological and Pharmacological Features of Metalloproteases

The polypeptides of the present invention, and in particular those being human species polypeptides, are structurally and functionally related to other proteins of the metalloprotease family, e.g. showing homology and/or structural similarity with metalloproteases or related enzymes, such as e.g. matrix metalloproteases (MMPs), angiotensin converting enzyme (ACE), endothelin converting enzyme (ECE) or neutral endopeptidase (NEP), respectively. Thus, for example, the polypeptide of the SEQ ID NO:2 is structurally and functionally related to other proteins of the metalloprotease family, having homology and/or structural similarity with enzymes such as neutral endopeptidase or endothelin converting enzyme (e.g. ECE-1), and in particular with neutral endopeptidase. Thus, preferred polypeptides and polynucleotides of the present invention are expected to have, inter alia, similar biological functions/properties to their homologous polypeptides and polynucleotides. Furthermore, preferred polypeptides and polynucleotides of the present invention have at least one IGS5 activity.

The general features of metalloproteases and their activities, in particular with regard to the present invention, are already described above. For further understanding of the nature and characteristics of the polypeptides and polynucleotides of the present invention, in particular the function of these polypeptides and polynucleotides, some more specific features of each of the enzymes like MMPs, ACE, ECE or NEP, respectively, are summarized as follows.

Matrix metalloproteases (MMPs), also designated matrixins, are a family of zinc metalloproteases that function in the turnover of components of the extracellular matrix. To date, several members of the matrixin family have been identified in humans. MMPs are synthesized and secreted from a number of cell types such as fibroblasts, epithelial cells, phagocytes, lymphocytes and cancer cells. MMPs are synthesized as pre-pro-enzymes which are destined to be secreted as proenzymes from all producing cells except neutrophils. Under physiological conditions these enzymes play central roles in morphogenesis, tissue remodelling and resorption. In excess, they participate in the destruction of the extracellular matrix associated with many connective tissue diseases such as in arthritis, periodontitis, glomerulonephritis, and with cancer cell invasion and metastasis. Thus, the MMPs play a central role, for example, in the normal embryo-genesis and tissue remodelling and in many diseases such as arthritis, cancer, periodontitis, glomerulonephritis, encephalomyelitis, atherosclerosis and tissue ulceration. The importance of the matrixins in both physiological and pathological catabolism of connective tissue matrix has been emphasized, because little MMP activity can be detected in normal steady-state tissues, but the synthesis of many MMPs is transcriptionally regulated by inflammatory cytokines, hormones, growth factors and on cellular transformation. The biological activities of MMPs are further controlled extracellularly during steps in their activation from inactive precursors (proMMPs), as well as through interaction with the extracellular substratum and endogenous inhibitors. The MMPs are an important class of zinc-dependent metalloproteases involved in degradation and remodeling of the extracellular matrix. Inhibitors of these enzymes have therapeutic potential in e.g. cancer, arthritis, osteoporosis and Alzheimer's disease, and several of these inhibitors are under clinical evaluation.

Angiotensin I Converting Enzyme (ACE; peptidyl dipeptidase A; EC 3.4.15.1) is a member of the angiotensin converting enzyme family of zinc metalloproteases. ACE is primarily expressed at the surface of endothelial, epithelial and neuroepithelial cells (somatic ACE) as an ectoenzyme, meaning that it is anchored to the plasma membrane with the bulk of its mass, including its catalytic site/s, facing the extracellular milieu. ACE is found in the plasma membrane of vascular endothelial cells, with high levels found at the vascular endothelial surface of the lung such that the active sites of ACE are posed to metabolize circulating substrates. In addition to the endothelial location of ACE, the enzyme is also expressed in the brush borders of absorptive epithelia of the small intestine and the kidney proximal convoluted tubule. ACE is also found in mononuclear cells, such as monocytes after macrophage differentiation and T-lymphocytes, and in fibroblasts. In vitro autoradiography, employing radiolabelled specific ACE inhibitors, and immunohistochemical studies have mapped the principal locations of ACE in the brain. ACE was found primarily in the choroid plexus, which may be the source of ACE in cerebrospinal fluid, ependyma, subformical organ, basal ganglia (caudate-putamen and globus pallidus), substantia nigra and pituitary. A soluble form of ACE has been detected in many biological fluids such as serum, seminal fluid, amniotic fluid and cerebrospinal fluid. The soluble form of ACE appears to be derived from the membrane-bound form of the enzyme in endothelial cells. A main physiological activity of ACE is that it cleaves the C-terminal dipeptide from angiotensin I to produce the potent vasopressor peptide angiotensin II and inactivates the vasodilatory peptide bradykinin by the sequential removal of two C-terminal dipeptides. As a consequence of the involvement of ACE in the metabolism of these two vasoactive peptides angiotensin II and bradykinin, ACE has become a crucial molecular target in the treatment of hypertension and congestive heart failure. This has led to the development of highly potent and specific ACE inhibitors which have become clinically important and widespread as orally active drugs to control these conditions of hypertension and congestive heart failure. Whilst the metabolism of vasoactive peptides remains the best known physiological function of ACE, the enzyme has been also implicated in a range of other physiological processes unrelated to blood pressure regulation such as immunity, reproduction and neuropeptide metabolism due to the localization of ACE and/or the in vitro cleavage of a range of biologically active peptides.

Neutral Endopeptidase (NEP, neprilysin, EC 3.4.24.11) is a zinc metalloprotease and classified as a member of the neprilysin family. NEP was first isolated from the brush border membranes of rabbit kidney. Later, an NEP-like enzyme was identified in rat brain as being involved in the degradation of the opioid peptides, enkephalins. The cloning of the ectoenzyme NEP and subsequent site-directed mutagenesis experiments have shown that, as well as having a similar specificity to thermolysin, it also has a similar active site organization. NEP also shows a thermolysin-like specificity for cleaving peptides on the N-terminal side of hydrophobic residues. With regard to the general distribution of NEP it has been determined in the brain and spinal cord, and lesion and electron microscopic studies generally support a predominantly neuronal localization of NEP, although the enzyme could be present on oligodendrocytes surrounding the fibers of the striato-pallidal and striato-nigral pathways and on Schwann cells in the peripheral nervous system. NEP does not appear to be concentrated on specific membrane interfaces such as the synapse, but is rather uniformly distributed on the surface of neuronal perikarya and dendrites. In the periphery, NEP is particularly abundant in the brush border membranes of the kidney and intestine, the lymph nodes and the placenta, and is found in lower concentrations in many other tissues including the vascular wall of the aorta. By finding that the common acute lymphoblastic leukemia antigen was NEP, it was also shown in the state of the art that the enzyme is transiently present at the surface of lymphohaematopoietic cells and elevated levels are found on mature lymphocytes in certain disease states. The clinical interest in NEP, in particular the interest in NEP inhibitors as potential clinical agents derives from the actions of NEP, in conjunction with another zinc metalloprotease, the aminopeptidase N (APN, membrane alanyl aminopeptidase, EC 3.4.11.2), in degrading the enkephalins and also from its role in degrading atrial natriuretic peptide (ANP). For example, it is known that dual inhibitors of NEP and angiotensin converting enzyme (ACE) are potent antihypertensives, resulting from simultaneously increasing the circulating levels of atrial natriuretic peptide, due to NEP inhibition, and decreasing the circulating levels of angiotensin II, due to ACE inhibition. Further interest in the clinical potential of NEP inhibitors came when the peripheral enzyme was shown to degrade the circulating natriuretic and diuretic peptide, atrial natriuretic peptide. NEP inhibitors were therefore investigated for their antihypertensive properties. From a further example it is known that inhibition of enkephalin metabolism by the synthetic NEP inhibitor, thiorphan, gave naloxone-reversible antinociceptive responses in mice. This opened the possibility that, by increasing the levels of endogenous opioids in the regions of their target receptors, an analgesia could be obtained relatively free of the side-effects of morphine or other classical opiate drugs. It was realized that in order to achieve any significant effect, other enkephalin-metabolizing enzymes also had to be inhibited, in particular the aminopeptidase N (APN). Such dual NEP/APN inhibitors completely block enkephalin metabolism and have strong antinociceptive properties.

Endothelin Converting Enzyme (ECE) catalyses the final step in the biosynthesis of the potent vasoconstrictor peptide endothelin (ET). This involves cleavage of the Trp-Val bond in the inactive intermediate, big endothelin. ECE-1 is a zinc metalloprotease which is homologous with neutral endopeptidase (NEP; neprilysin; EC 3.4.24.11, see above). Like NEP, ECE-1 is inhibited by the compound phosphoramidon and is a type II integral membrane protein. Unlike NEP, however, ECE-1 exists as a disulfide-linked dimer and is not inhibited by other NEP inhibitors such as thiorphan. Immunocytochemical studies indicate a predominant cell-surface location for ECE-1 where it exists as an ectoenzyme. ECE-1 is localized to endothelial cells and some secretory cells, e.g. β-cells in the pancreas, and in smooth muscle cells. Potent and selective inhibitors of ECE, or dual inhibitors of ECE and NEP, may have therapeutic applications in cardiovascular and renal medicine. Endothelin (ET) which is a 21 amino acid bicyclic peptide containing two intramolecular disulfide bonds, is one of the most potent vasoconstricting peptides identified to date and administration to animals results in a sustained increase in blood pressure emphasizing its potential role in cardiovascular regulation. The endogenous production of ET-1 in humans contributes to the maintenance of basal vascular tone. The endothelin system and related enzymes like ECE therefore represent a likely candidate for the development of novel pharmaceutical agents. Thus, the clinical interest in ECE, in particular the interest in ECE inhibitors as potential clinical agents derives from the actions of ECE, in particular in the context of the biosynthesis of ET. Consequently, compounds showing a significant endothelin converting enzyme inhibitory activity are useful in treating and preventing various diseases which are induced or suspected to be induced by ET, such as for example, cardiovascular diseases including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; asthma; stroke, Alzheimer's disease; complication of diabetes mellitus; ulcer such as gastric ulcer; cancer such as lung cancer; endotoxin shock; sepsis; and the like.

The Polypeptides of the present invention are in particular of interest in the context of cardiovascular diseases.

Procedures for Obtaining Polynucleotides of the Present Invention

Polynucleotides of the present invention may be obtained, using standard cloning and screening techniques, from a cDNA library derived from mRNA in cells of human testis tissue, using the expressed sequence tag (EST) analysis (Adams, M. D., et al. Science (1991) 252:1651–1656; Adams, M. D. et al., Nature, (1992) 355:632–634; Adams, M. D., et al., Nature (1995) 377 Supp:3–174). Polynucleotides of the invention can also be obtained from natural sources such as genomic DNA libraries or can be synthesized using well known and commercially available techniques (e.g. F. M. Ausubel et al., 2000, Current Protocols in Molecular Biology).

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise one of the amino acid sequences selected from the group of of SEQ ID NO:2, SEQ ID NO:4 and SEQ ID NO:6, and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in one of SEQ ID NO:1, SEQ ID NO:3 or SEQ ID NO:5, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to one of SEQ ID NO:1, SEQ ID NO:3 or SEQ ID NO:5. Typically these nucleotide sequences are at least 70% identical, preferably at least 80% and in particular at least 85% identical, more preferably at least 90% identical, still more preferably at least 95%, still more preferably at least 96%, still more preferably at least 97%, still more preferably at least 98%, still more preferably at least 99%, identical to that of the referent. The probes or primers will generally comprise at least 15 nucleotides, preferably, at least 30 nucleotides and may have at least 50 nucleotides. Particularly preferred probes will have between 30 and 50 nucleotides. Particularly preferred primers will have between 20 and 25 nucleotides.

A polynucleotide encoding a polypeptide of the present invention, including homologs and orthologs from species other than human, may be obtained by a process which comprises the steps of screening an appropriate library under stringent hybridization conditions with a labeled probe having the sequence of one of SEQ ID NO: 1, SEQ ID NO:3 or SEQ ID NO:5, or a fragment thereof; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate (w/v), and 20 microgram/ml denatured, sheared salmon sperm DNA; followed by washing the filters in 0.1×SSC at about 65° C. Thus the present invention also includes polynucleotides obtainable by screening an appropriate library under stringent hybridization conditions with a labeled probe having the sequence of one of SEQ ID NO:1, SEQ ID NO:3 or SEQ ID NO:5, or a fragment thereof.

The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low "processivity" (a measure of the ability of the enzyme to remain attached to the template during the polymerisation reaction), failing to complete a DNA copy of the mRNA template during 1st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an "adaptor" sequence ligated onto each end. Nucleic acid amplification (PCR) is then carried out to amplify the "missing" 5' end of the cDNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Vectors, Host Cells, Expression

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as Streptococci, Staphylococci, *E. coli*, *Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., Molecular Cloning, A Laboratory Manual (supra). Appropriate secretion signals may be incorporated into the desired polypeptide to allow secretion of the translated protein into the lumen of the endoplasmic reticulum, the periplasmic space or the extracellular environment.

These signals may be endogenous to the polypeptide or they may be heterologous signals, i.e. derived from a different species.

If a polypeptide of the present invention is to be expressed for use in screening assays, it is generally possible that the polypeptide be produced at the surface of the cell or alternatively in a soluble protein form. If the polypeptide is secreted into the medium, the medium can be recovered in order to recover and purify the polypeptide. If produced intracellularly, the cells must first be lysed before the polypeptide is recovered. If the polypeptide is bound at the surface of the cell (membrane bound polypeptide), usually membrane fractions are prepared in order to accumulate the membrane bound polypeptide.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and or purification.

Diagnostic Assays

This invention also relates to the use of polynucleotides of the present invention as diagnostic reagents. Detection of a mutated form of the gene characterized by one of the the polynucleotides selected from the group of SEQ ID NO:1, SEQ ID NO:3 and SEQ ID NO:5, which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled IGS5 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (ee, e.g., Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401). In another embodiment, an array of oligonucleotides probes comprising IGS5 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610–613 (1996)).

The diagnostic assays offer a process for diagnosing or determining a susceptibility to the Diseases through detection of mutation in the IGS5 gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radio-immuno-assays, competitive-binding assays, Western Blot analysis and ELISA assays.

Thus in another aspect, the present invention relates to a diagnostic kit which comprises:

(a) a polynucleotide of the present invention, preferably the nucleotide sequence of one of SEQ ID NO: 1, SEQ ID NO:3 or SEQ ID NO:5, or a fragment thereof;

(b) a nucleotide sequence complementary to that of (a);

(c) a polypeptide of the present invention, preferably the polypeptide of one of SEQ ID NO:2, SEQ ID NO:4 or SEQ ID NO:6, or a fragment thereof; or (d) an antibody to a polypeptide of the present invention, preferably to one of the polypeptides of SEQ ID NO:2, SEQ ID NO:4 or SEQ ID NO:6.

It will be appreciated that in any such kit, the component (a), (b), (c) or (d) may constitute a substantial component of said diagnostic kit. Such a kit will be of use in diagnosing a disease or susceptibility to a disease, particularly amongst others a disease as indicated above in the context of the polypeptides of the present invention.

Chromosome Assays

The nucleotide sequences of the present invention are also valuable for chromosome localization. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Tissue Localization

The nucleotide sequences of the present invention are also valuable for tissue localization. Such techniques allow the determination of expression patterns of the IGS5 polypeptides in tissues by detection of the mRNAs that encode them.

These techniques include in situ hybridization techniques and nucleotide amplification techniques, for example PCR. Such techniques are well known in the art. Results from these studies provide an indication of the normal functions of the polypeptides in the organism. In addition, comparative studies of the normal expression pattern of IGS5 mRNAs with that of mRNAs encoded by a IGS5 gene provide valuable insights into the role of mutant IGS5 polypeptides, or that of inappropriate expression of normal IGS5 polypeptides, in disease. Such inappropriate expression may be of a temporal, spatial or simply quantitative nature.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985). Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

Antibodies against polypeptides of the present invention may also be employed to treat the diseases as indicated above, amongst others.

Fusion Proteins

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Vaccines

Another aspect of the invention relates to a method for inducing an immunological response in a mammal which comprises administering to (for example by inoculation) the mammal a polypeptide of the present invention, adequate to produce antibody and/or T cell immune response to protect said animal from the Diseases hereinbefore mentioned, amongst others. Yet another aspect of the invention relates to a method of inducing immunological response in a mammal which comprises, delivering a polypeptide of the present invention via a vector directing expression of the polynucleotide and coding for the polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a polypeptide of the present invention wherein the composition comprises a polypeptide or polynucleotide of the present invention. Such immunological/vaccine formulations (compositions) may be either therapeutic immunological/vaccine formulations or prophylactic immunological/vaccine formulations. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

Polypeptides of the present invention are responsible for one or more biological functions, including one or more disease states, in particular the Diseases hereinbefore mentioned. It is therefore desirous to devise screening methods to identify compounds which stimulate or which inhibit the function of the polypeptide. Accordingly, in a further aspect, the present invention provides for a method of screening compounds to identify those which stimulate or which inhibit the function of the polypeptide. Compounds may be identified from a variety of sources, for example, cells, cell-free preparations, chemical libraries, and natural product mixtures. Such stimulators or inhibitors so-identified may be natural or modified substrates, ligands, receptors, enzymes, etc., as the case may be, of the polypeptide; or may be structural or functional mimetics thereof (see Coligan et al., Current Protocols in Immunology 1(2):Chapter 5 (1991)).

The screening method may simply measure the influence of a candidate compound on the activity of the polypeptide, or on cells or membranes bearing the polypeptide. Alternatively, the screening method may involve competition with a competitor. Further, these screening methods may test whether the candidate compound results in a signal generated by activation or inhibition of the polypeptide, using detection systems appropriate to the activity of the polypeptide or to the cells or membranes bearing the polypeptide. Inhibition of polypeptide activity is generally assayed in the presence of a known substrate and the effect of the candidate compound is observed by altered activity, e.g. by testing whether the candidate compound results in inhibition or stimulation of the polypeptide. For example, the screening methods may simply comprise the steps of mixing a candidate compound with a solution containing a polypeptide of the present invention, and a suitable substrate to form a mixture, measuring IGS5 activity in the mixture, and comparing the IGS5 activity of the mixture to a standard without candidate compound.

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide from suitably manipulated cells or tissues.

Examples of potential polypeptide inhibitors include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Thus, in another aspect, the present invention relates to a screening kit for identifying in particular inhibitors, stimulators, ligands, receptors, substrates, enzymes, etc. for polypeptides of the present invention; or compounds which decrease or enhance the production of such polypeptides, which comprises:

(a) a polypeptide of the present invention;

(b) a recombinant cell expressing a polypeptide of the present invention;

(c) a cell membrane expressing a polypeptide of the present invention; or (d) an antibody to a polypeptide of the present invention; which polypeptide is preferably one of that of SEQ ID NO:2, SEQ ID NO:4 or SEQ ID NO:6.

It will be appreciated that in any such kit, the component (a), (b), (c) or (d) may constitute a substantial part of said kit.

It will be readily appreciated by the skilled artisan that a polypeptide of the present invention may also be used in a method for the structure-based design of a stimulator or inhibitor of the polypeptide, by:

(a) determining in the first instance the three-dimensional structure of the polypeptide;

(b) deducing the three-dimensional structure for the likely reactive or binding site(s) of a stimulator or inhibitor;

(c) synthesizing candidate compounds that are predicted to bind to or react with the deduced binding or reactive site; and (d) testing whether the candidate compounds are indeed stimulators or inhibitors.

It will be further appreciated that this will normally be an iterative process.

Prophylactic and Therapeutic Methods

In a further aspect, the present invention provides methods of treating abnormal conditions such as, for instance, those dysfunctions, disorders or diseases to be treated, hereinabove generally referred to as "the diseases" in the context of the polypeptides of the present invention, related to either an excess of, or an under-expression of IGS5 polypeptide activity.

If the activity of the polypeptide is in excess, several approaches are available. One approach comprises administering to a subject in need thereof an inhibitor compound as hereinabove described, optionally in combination with a pharmaceutically acceptable carrier, in an amount effective to inhibit the function of the polypeptide, such as, for example, by blocking the binding of substrates, enzymes, etc., and thereby alleviating the abnormal condition. In another approach, soluble forms of the polypeptides still capable of binding the substrate, enzymes, etc. in competition with endogenous polypeptide may be administered. Typical examples of such competitors include fragments of the IGS5 polypeptide.

In still another approach, expression of the gene encoding endogenous IGS5 polypeptide can be inhibited using expression blocking techniques. Known such techniques involve the use of antisense sequences, either internally generated or separately administered (see, for example, O'Connor, J. Neurochem. (1991) 56:560 in Oligodeoxynucleotides as Antisense Inhibitors of Gene Expression, CRC Press, Boca Raton, Fla. (1988)). Alternatively, oligonucleotides which form triple helices ("triplexes") with the gene can be supplied (see, for example, Lee et al., Nucleic Acids Res (1979) 6:3073; Cooney et al., Science (1988) 241:456; Dervan et al., Science (1991) 251:1360). These oligomers can be administered per se or the relevant oligomers can be expressed in vivo. Synthetic antisense or triplex oligonucleotides may comprise modified bases or modified backbones. Examples of the latter include methylphosphonate, phosphorothioate or peptide nucleic acid backbones. Such backbones are incorporated in the antisense or triplex oligonucleotide in order to provide protection from degradation by nucleases and are well known in the art. Antisense and triplex molecules synthesized with these or other modified backbones also form part of the present invention.

In addition, expression of the IGS5 polypeptide may be prevented by using ribozymes specific to the IGS5 mRNA sequence. Ribozymes are catalytically active RNAs that can be natural or synthetic (see for example Usman, N, et al., Curr. Opin. Struct. Biol (1996) 6(4), 527–33.) Synthetic ribozymes can be designed to specifically cleave IGS5 mRNAs at selected positions thereby preventing translation of the IGS5 mRNAs into functional polypeptide. Ribozymes may be synthesized with a natural ribose phosphate backbone and natural bases, as normally found in RNA molecules. Alternatively the ribozymes may be synthesized with non-natural backbones to provide protection from ribonuclease degradation, for example, 2'-O-methyl RNA, and may contain modified bases.

For treating abnormal conditions related to an under-expression of IGS5 and its activity, several approaches are also available. One approach comprises administering to a subject a therapeutically effective amount of a compound which stimulates a polypeptide of the present invention in combination with a pharmaceutically acceptable carrier, to thereby alleviate the abnormal condition. Alternatively, gene therapy may be employed to effect the endogenous production of IGS5 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

Formulation and Administration

In a further aspect, the present invention provides for pharmaceutical compositions comprising a therapeutically effective amount of a polypeptide, such as the soluble form of a polypeptide of the present invention, stimulating or inhibiting peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Polynucleotide and polypeptide sequences form a valuable information resource with which it is possible to identify further sequences of similar homology. This is most easily facilitated by storing the sequence in a computer readable medium and then using the stored data to search a sequence database using well known searching tools, such as those in the GCC and Lasergene software packages. Accordingly, in a further aspect, the present invention provides for a computer readable medium having stored thereon a polynucleotide comprising the sequences of SEQ ID NO:1, SEQ ID NO:3 or SEQ ID NO:5 and/or a polypeptide sequence encoded thereby.

All publications, including but not limited to patents and patent applications, cited in this specification are herein incorporated by reference as if each individual publication were specifically and individually indicated to be incorporated by reference herein as though fully set forth.

The following examples are only intended to further illustrate the invention, in more detail, and therefore these examples are not deemed to restrict the scope of the invention in any way.

TABLE 1

IGS5-DNA ("IGS5DNA") of SEQ ID NO:1

5' -

TGCACCACCCCTGGCTGCGTGATAGCAGCTGCCAGGATCCTCCAGAACATGGACCCGACC

ACGGAACCGTGTGACGACTTCTACCAGTTTGCATGCGGAGGCTGGCTGCGGCGCCACGTG

ATCCCTGAGACCAACTCAAGATACAGCATCTTTGACGTCCTCCGCGACGAGCTGGAGGTC

ATCCTCAAAGCGGTGCTGGAGAATTCGACTGCCAAGGACCGGCCGGCTGTGGAGAAGGCC

AGGACGCTGTACCGCTCCTGCATGAACCAGAGTGTGATAGAGAAGCGAGGCTCTCAGCCC

CTGCTGGACATCTTGGAGGTGGTGGGAGGCTGGCGGTGGCGATGGACAGGTGGAACGAG

ACCGTAGGACTCGAGTGGGAGCTGGAGCGGCAGCTGGCGCTGATGAACTCACAGTTCAAC

AGGCGCGTCCTCATCGACCTCTTCATCTGGAACGACGACCAGAACTCCAGCCGGCACATC

TABLE 1-continued

IGS5-DNA ("IGS5DNA") of SEQ ID NO:1

ATCTACATAGACCAGCCCACCTTGGGCATGCCCTCCCGAGAGTACTACTTCAACGGCGGC

AGCAACCGGAAGGTGCGGGAAGCCTACCTGCAGTTCATGGTGTCAGTGGCCACGTTGCTG

CGGGAGGATGCAAACCTGCCCAGGGACAGCTGCCTGGTGCAGGAGGAGATGATGCAGGTG

CTGGAGCTGGAGACACAGCTGGCCAAGGCCACGGTACCCCAGGAGGAGAGACACGACGTC

ATCGCCTTGTACCACCGGATGGGACTGGAGGAGCTGCAAAGCCAGTTTGGCCTGAAGGGA

TTTAACTGGACTCTGTTCATACAAACTGTGCTATCCTCTGTCAAAATCAAGCTGCTGCCA

GATGAGGAAGTGGTGGTCTATGGCATCCCCTACCTGCAGAACCTTGAAAACATCATCGAC

ACCTACTCAGCCAGGACCATACAGAACTACCTGGTCTGGCGCCTGGTGCTGGACCGCATT

GGTAGCCTAAGCCAGAGATTCAAGGACACACGAGTGAACTACCGCAAGGCGCTGTTTGGC

ACAATGGTGGAGGAGGTGCGCTGGCGTGAATGTGTCGGCTACGTCAACAGCAACATGGAG

AACGCCGTGGGCTCCCTCTACGTCAGGGAGGCGTTCCCTGGAGACAGCAAGAGCATGGTC

AGAGAACTCATTGACAAGGTGCGGACAGTGTTTGTGGAGACGCTGGACGAGCTGGGCTGG

ATGGACGAGGAGTCCAAGAAGAAGGCGCAGGAGAAGGCCATGAGCATCCGGGAGCAGATC

GGGCAGCCTGACTACATCCTGGAGGAGATGAACAGGCGCCTGGACGAGGAGTACTCCAAT

CTGAACTTCTCAGAGGACCTGTACTTTGAGAACAGTCTGCAGAACCTCAAGGTGGGCGCC

CAGCGGAGCCTCAGGAAGCTTCGGGAAAAGGTGGACCCAAATCTCTGGATGATCGGGGCG

GCGGTGGTCAATGCGTTCTACTCCCCAAACCGAAACCAGATTGTATTCCCTGCCGGGATC

CTCCAGCCCCCCTTCTTCAGCAAGGAGCAGCCACAGGCCTTGAACTTTGGAGGCATTGGG

ATGGTGATCGGCACGAGATCACGCACGGCTTTGACGACAATGGCCGGAACTTCGACAAG

AATGGCAACATGATGGATTGGTGGAGTAACTTCTCCACCCAGCACTTCGGGAGCAGTCA

GAGTGCATGATCTACCAGTACGGCAACTACTCCTGGGACCTGGCAGACGAACAGAACGTG

AACGGATTCAACACCCTTGGGGAAAACATTGCTGACAACGGAGGGGTGCGGCAAGCCTAT

AAGGCCTACCTCAAGTGGATGGCAGAGGGTGGCAAGGACCAGCAGCTGCCCGGCCTGGAT

CTCACCCATGAGCAGCTCTTCTTCATCAACTACGCCCAGGTGTGGTGCGGGTCCTACCGG

CCCGAGTTCGCCATCCAATCCATCAAGACAGACGTCCACAGTCCCTGAAGTACAGGGTA

CTGGGGTCGCTGCAGAACCTGGCCGCCTTCGCAGACACGTTCCACTGTGCCCGGGGCACC

CCCATGCACCCCAAGGAGCGATGCCGCGTGTGGTAG - 3'

TABLE 2

IGS5-protein ("IGS5PROT") of SEQ ID NO:2

CTTPGCVIAAARILQNMDPTTEPCDDFYQFACGGWLRRHVIPETNSRYSIFDVLRDELEV

ILKAVLENSTAKDRPAVEKARTLYRSCMNQSVIEKRGSQPLLDILEVVGGWPVAMDRWNE

TVGLEWELERQLALMNSQFNRRVLIDLFIWNDDQNSSRHIIYIDQPTLGMPSREYYFNGG

SNRKVREAYLQFMVSVATLLREDANLPRDSCLVQEDMMQVLELETQLAKATVPQEERHDV

IALYHRMGLEELQSQFGLKGFNWTLFIQTVLSSVKIKLLPDEEVVVYGIPYLQNLENIID

TYSARTIQNYLVWRLVLDRIGSLSQRFKDTRVNYRKALFGTMVEEVRWRECVGYVNSNME

NAVGSLYVREAFPGDSKSMVRELIDKVRTVFVETLDELGWMDEESKKKAQEKAMSIREQI

GHPDYILEEMNRRLDEEYSNLNFSEDLYFENSLQNLKVGAQRSLRKLREKVDPNLWIIGA

TABLE 2-continued

IGS5-protein ("IGS5PROT") of SEQ ID NO:2

AVVNAFYSPNRNQIVFPAGILQPPFFSKEQPQALNFGGIGMVIGHEITHGFDDNGRNFDK

NGNMMDWWSNFSTQHFREQSECMIYQYGNYSWDLADEQNVNGFNTLGENIADNGGVRQAY

KAYLKWMAEGGKDQQLPGLDLTHEQLFFINYAQVWCGSYRPEFAIQSIKTDVHSPLKYRV

LGSLQNLAAFADTFHCARGTPMHPKERCRVW

TABLE 3

IGS5-DNA-1 ("IGS5DNA1") of SEQ ID NO: 3

5' -

ATGGGGAAGTCCGAAGGCCCCGTGGGATGGTGGAGAGCGCTGGCCGTGCAGGGCAGAAG

CGCCCGGGGTTCCTGGAGGGGGGGCTGCTGCTGCTGCTGCTGGTGACCGCTGCCCTG

GTGGCCTTGGGTGTCCTCTACGCCGACCGCAGAGGGAAGCAGCTGCCACGCCTTGCTAGC

CGGCTGTGCTTCTTACAGGAGGAGAGGACCTTTGTAAAACGAAAACCCCGAGGGATCCCA

GAGGCCCAAGAGGTGAGCGAGGTCTGCACCACCCCTGGCTGCGTGATAGCAGCTGCCAGG

ATCCTCCAGAACATGGACCCGACCACGGAACCGTGTGACGACTTCTACCAGTTTGCATGC

GGAGGCTGGCTGCGGCGCCACGTGATCCCTGAGACCAACTCAAGATACAGCATCTTTGAC

GTCCTCCGCGACGAGCTGGAGGTCATCCTCAAAGCGGTGCTGGAGAATTCGACTGCCAAG

GACCGGCCGGCTGTGGAGAAGGCCAGGACGCTGTACCGCTCCTGCATGAACCAGAGTGTG

ATAGAGAAGCGAGGCTCTCAGCCCCTGCTGGACATCTTGGAGGTGGTGGGAGGCTGGCCG

GTGGCGATGGACAGGTGGAACGAGACCGTAGGACTCGAGTGGGAGCTGGAGCGGCAGCTG

GCGCTGATGAACTCACAGTTCAACAGGGGCGTCGTCATCGACCTCTTCATCTGGAACGAC

GACCAGAACTCCAGCCGGCACATCATCTACATAGACCAGCCCACCTTGGGCATGCCCTCC

CGAGAGTAGTACTTCAACGGCGGCAGCAACCGGAAGGTGCGGGAAGCCTACCTGCAGTTC

ATGGTGTCAGTGGCCACGTTGCTGCGGGAGGATGCAAACCTGCCCAGGGACAGCTGCCTG

GTGCAGGAGGACATGATGCAGGTGCTGGAGCTGGAGACACAGCTGGCCAAGGCCACGGTA

CCCCAGGAGGAGAGACACCACGTCATCGCCTTGTACCACCGGATGGGACTGGAGGAGCTG

CAAAGCCAGTTTGGCCTGAAGGGATTTAACTGGACTCTGTTCATACAAACTGTGCTATCC

TCTGTCAAAATCAAGCTGCTGCCAGATGAGGAAGTGGTGGTCTATGGCATCGCCTACCTG

GAGAACCTTGAAAACATCATCGACACCTACTCAGCCAGGACCATACAGAACTACCTGGTC

TGGCGCCTGGTGCTGGACCGCATTGGTAGCCTAAGCCAGAGATTCAAGGACACACGAGTG

AACTACCGCAAGGGGCTGTTTGGCACAATGGTGGAGGAGGTGCGCTGGCGTGAATGTGTG

GGCTACGTCAACAGCAACATGGAGAACGCCGTGGGCTCCCTCTACGTCAGGGAGGCGTTC

CCTGGAGACAGCAAGAGCATGGTCAGAGAACTCATTGACAAGGTGCGGACAGTGTTTGTG

GAGACGCTGGACGAGCTGGGCTGGATGGACGAGGAGTCCAAGAAGAAGGCGGAGGAGAAG

GCCATGAGCATCCGGGAGCAGATCGGGCACCCTGACTACATCCTGGAGGAGATGAACAGG

CGCCTGGACGAGGAGTACTCCAATCTGAACTTCTCAGAGGACCTGTACTTTGAGAACAGT

CTGCAGAACCTCAAGGTGGGCGCCCAGCGGAGCCTCAGGAAGCTTCGGGAAAAGGTGGAC

CCAAATCTCTGGATCATCGGGGCGGCGGTGGTCAATGCGTTCTACTCCCAAACCGAAAC

CAGATTGTATTCCCTGCCGGGATCCTCCAGCCCCCCTTCTTCAGCAAGGAGCAGCCACAG

TABLE 3-continued

IGS5-DNA-1 ("IGS5DNA1") of SEQ ID NO: 3

GCCTTGAACTTTGGAGGCATTGGGATGGTGATCGGGCACGAGATCACGCACGGCTTTGAC

GACAATGGCCGGAACTTCGACAAGAATGGCAACATGATGGATTGGTGGAGTAACTTCTGC

ACCCAGCACTTCCGGGAGCAGTCAGAGTGCATGATCTACCAGTACGGCAACTACTCCTGG

CACCTGGCAGACGAACAGAACGTGAACCGATTCAACACCCTTGGGGAAAACATTGCTGAC

AACGGAGGGGTGCGGCAAGCCTATAAGGCCTACCTCAAGTGGATGGCAGAGGGTGGCAAG

GACCAGCAGCTGCCCGGGCTGGATCTCACCCATGAGCAGCTCTTCTTCATCAACTACGCC

CAGGTGTGGTGCGGGTCCTACCGGCCCGAGTTCGCCATCCAATCCATCAAGACAGACGTC

CACAGTCCCCTGAAGTACAGGGTACTGGGGTCGCTGCAGAACCTGGCCGCCTTCGCAGAC

ACGTTCCACTGTGCCCGGGGCACCCCCATGCACCCCAAGGAGCGATGCCGCGTGTGGTAG

- 3'

TABLE 4

IGS5-protein-1 ("IGS5PROT1") of SEQ ID NO:4

MGKSEGPVGMVESAGRAGQKRPGFLEGGLLLLLLLVTAALVALGVLYADRRGKQLPRLAS

RLCFLQEERTFVKRKPRGIPEAQEVSEVCTTPGCVIAAARILQNMDPTTEPCDDFYQFAC

GGWLRRHVIPETNSRYSIFDVLRDELEVILKAVLENSTAKDRPAVEKARTLYRSCMNQSV

IEKRGSQPLLDILEVVGGWPVAMDRWNETVGLEWELERQLALMNSQFNRRVLIDLFIWND

DQNSSRHIIYIDQPTLGMPSREYYFNGGSNRKVREAYLQFMVSVATLLREDANLPRDSCL

VQEDMMQVLELETQLAKATVPQEERHDVIALYHRMGLEELQSQFGLKGFNWTLFIQTVLS

SVKIKLLPDEEVVVYGIPYLQNLENIIDTYSARTIQNYLVWRLVLDRIGSLSQRFKDTRV

NYRKALFGTMVEEVRWRECVGYVNSNMENAVGSLYVREAFPGDSKSMVRELIDKVRTVFV

ETLDELGWMDEESKKKAQEKAMSIREQIGHPDYILEEMNRRLDEEYSNLNFSEDLYFENS

LQNLKVGAQRSLRKLREKVDPNLWIIGAAVVNAFYSPNRNQIVFPAGILQPPFFSKEQPQ

ALNFGGIGMVIGHEITHGFDDNGRNFDKNGNMMDWWSNFSTQHFREQSECMIYQYGNYSW

DLADEQNVNGFNTLGENIADNGGVRQAYKAYLKWMAEGGKDQQLPGLDLTHEQLFFINYA

QVWCGSYRPEFAIQSIKTDVHSPLKYRVLGSLQNLAAFADTFHCARGTPMHPKERCRVW

TABLE 5

IGS5-DNA-2 ("IGS5DNA2") of SEQ ID NO:5

5' -

ATGGGGAAGTCCGAAGGCCCAGTGGGGATGGTGGAGAGCGCCGGCCGTGCAGGGCAGAAG

CGCCCGGGGTTCCTGGAGGGGGGCTGCTGCTGCTGCTGCTGGTGACCGCTGCCCTG

GTGGCCTTGGGTGTCCTCTACGCCGACCGCAGAGGGATCCCAGAGGCCCAAGAGGTGAGC

GAGGTCTGCACCACCCCTGGCTGCGTGATAGCAGCTGCCAGGATCCTCCAGAACATGGAC

CCGACCACGGAACCGTGTGAGGACTTGTACCAGTTTGCATGCGGAGGCTGGCTGCGGCGC

CACGTGATCCCTGAGACCAACTCAAGATACAGCATCTTTGACGTCCTGCGCGACGAGCTG

GAGGTCATCCTCAAAGCGGTGCTGGAGAATTCGACTGCCAAGGACCGGCCGGCTGTGGAG

AAGGCCAGGACGCTGTACCGCTCCTGCATGAACCAGAGTGTGATAGAGAAGCGAGGCTCT

TABLE 5-continued

IGS5-DNA-2 ("IGS5DNA2") of SEQ ID NO:5

CAGCCCCTGCTGGACATCTTGGAGGTGGTGGGAGGCTGGCCGGTGGCGATGGACAGGTGG

AACGAGACCGTAGGACTGGAGTGGGAGCTGGAGCGGCAGCTGGCGCTGATGAACTCACAG

TTCAACAGGCGCGTCCTCATCGACCTCTTCATCTGGAACGACGACCAGAACTCCAGCCGG

CACATCATCTACATAGACCAGCCCACCTTGGGCATGCCCTCCCGAGAGTACTACTTCAAC

GGCGGCAGCAACCGGAAGGTGCGGGAAGCCTACCTGGAGTTCATGGTGTCAGTGGCCACG

TTGCTGCGGGAGGATGCAAACCTGCCCAGGGACAGCTGCCTGGTGCAGGAGGACATGATG

CAGGTGCTGGAGCTGGAGACACAGCTGGCCAAGGCCACGGTACCCCAGGAGGAGAGACAC

GACGTCATCGCCTTGTACCACCGGATGGGACTGGAGGAGCTGCAAAGCCAGTTTGGCCTG

AAGGGATTTAACTGGACTCTGTTCATACAAACTGTGCTATCCTCTGTCAAAATCAAGCTG

CTGCCAGATGAGGAAGTGGTGGTCTATGGCATCCCCTACCTGCAGAACCTTGAAAACATC

ATCGACACCTACTCAGCCAGGACCATACAGAACTAGCTGGTCTGGCGCCTGGTGCTGGAC

CGCATTGGTAGCCTAAGCCAGAGATTCAAGGACACACGAGTGAACTACCGCAAGGCGCTG

TTTGGCACAATGGTGGAGGAGGTGCGCTGGCGTGAATGTGTGGGCTACGTCAACAGCAAC

ATGGAGAACGCCGTGGGCTCCCTCTACGTCAGGGAGGCGTTCCCTGGAGACAGCAAGAGC

ATGGTCAGAGAAGTCATTGACAAGGTGCGGACAGTGTTTGTGGAGACGCTGGACGAGCTG

GGCTGGATGGACGAGGAGTCCAAGAAGAAGGCGCAGGAGAAGGCCATGAGCATCCGGGAG

CAGATCGGGCACCCTGACTACATCCTGGAGGAGATGAACAGGCGCCTGGACGAGGAGTAC

TCCAATCTGAACTTCTCAGAGGACCTGTACTTTGAGAACAGTCTGCAGAACCTCAAGGTG

GGCGCCCAGCGGAGCCTGAGGAAGCTTCGGGAAAAGGTGGAGCCAAATCTCTGGATCATC

GGGGCCGCGGTGGTCAATGCGTTCTACTCCCCAAACCGAAACCAGATTGTATTCCCTGCC

GGGATCCTCCAGCCCCCCTTCTTCAGCAAGGAGCAGCCACAGGCCTTGAACTTTGGAGGC

ATTGGGATGGTGATCGGGCACGAGATCACGCACGGCTTTGAGGACAATGGCCGGAACTTC

GACAAGAATGGCAACATGATGGATTGGTGGAGTAACTTCTCGACCCAGCACTTCGGGGAG

CAGTCAGAGTGCATGATCTACCAGTACGGCAACTACTCCTGGGACCTGGCAGACGAACAG

AACGTGAACGGATTCAACACCCTTGGGGAAAACATTGCTGACAACGGAGGGGTGCGGCAA

GCCTATAAGGCCTACCTCAAGTGGATGGCAGAGGGTGGCAAGGACCAGCAGCTGCCCGGC

CTGGATCTCACCCATGAGCAGCTCTTCTTCATCAACTACGCCCAGGTGTGGTGCGGGTCC

TACCGGCCCGAGTTCGCCATCCAATCCATCAAGACAGACGTCCACAGTCCCCTGAAGTAC

AGGGTACTGGGGTCGCTGCAGAACCTGGCCGCCTTCGCAGACACGTTCCACTGTGCCCGG

GGCACCCCCATGCACCCCAAGGAGCGATGCCGCGTGTGGTAG - 3'

TABLE 6

IGS5-protein-2 ("IGS5PROT2") of SEQ ID NO:6

MGKSEGPVGMVESAGRAGQKRPGFLEGGLLLLLLLVTAALVALGVLYADRRGIPEAQEVS

EVCTTPGCVIAAARILQNMDPTTEPCDDFYQFACGGWLRRHVIPETNSRYSIFDVLRDEL

EVILKAVLENSTAKDRPAVEKARTLYRSCMNQSVIEKRGSQPLLDILEVVGGWPVAMDRW

NETVGLEWELERQLALMNSQFNRRVLIDLFIWNDDQNSSRHIIYIDQPTLGMPSREYYFN

GGSNRKVREAYLQFMVSVATLLREDANLPRDSCLVQEDMMQVLELETQLAKATVPQEERH

TABLE 6-continued

IGS5-protein-2 ("IGS5PROT2") of SEQ ID NO:6

DVIALYHRMGLEELQSQFGLKGFNWTLFIQTVLSSVKIKLLPDEEVVVYGIPYLQNLENI

IDTYSARTIQNYLVWRLVLDRIGSLSQRFKDTRVNYRKALFGTMVEEVRWRECVGYVNSN

MENAVGSLYVREAFPGDSKSMVRELIDKVRTVFVETLDELGWMDEESKKKAQEKAMSIRE

QIGHPDYILEEMNRRLDEEYSNLNFSEDLYFENSLQNLKVGAQRSLRKLREKVDPNLWII

GAAVVNAFYSPNRNQIVFPAGILQPPFFSKEQPQALNFGGIGMVIGHEITHGFDDNGRNF

DKNGNMMDWWSNFSTQHFREQSECMIYQYGNYSWDLADEQNVNGFNTLGENIADNGGVRQ

AYKAYLKWMAEGGKDQQLPGLDLTHEQLFFINYAQVWCGSYRPEFAIQSIKTDVHSPLKY

RVLGSLQNLAAFADTFHCARGTPMHPKERCRVW

EXAMPLE 1

The Cloning of cDNA Encoding a Novel Member of the NEP/ECE Metalloprotease Family

EXAMPLE 1a

Homology PCR Cloning of a cDNA Fragment of a Novel Member of the NEP/ECE Metalloprotease Family In the DNA databank of expressed sequence tags (ESTs) 4 overlapping EST sequences (accession nos. AA524283, AI088893, AI217369 and AI380811) were detected which contained a small open reading frame encoding a stretch of protein that showed similarity to the C-terminal part of members of the neutral endopeptidase 24.11/endothelin converting enzyme (NEP/ECE) metalloprotease protein family (Turner A. J. et al. Faseb J. (1997) 11: 355–364). The NEP/ECE-like small open reading frame in these ESTs was terminated by a stop codon (in the case of AA524283) and was preceded in all 4 ESTs by a sequence that contained stop codons in all 3 reading frames. This preceeding sequence appeared totally unrelated to NEP/ECE metalloprotease family members.

Although the polarity of the small open reading frame was opposite to the 5'->3' orientation of the mRNA from which these ESTs had been derived, these sequences were used as the basis for a RT-PCR homology cloning approach. In parallel, additional EST sequences, that showed the same structure as the 4 ESTs mentioned before, were observed to appear in the public domain databanks, e.g. accession nos: AI825876, AI888306, AI422224, AI422225, AI469281, AA975272, AA494534, AW006103, AI827701, AI650385, AI827898, AI934499 and AA422157.

The RT-PCR reactions were carried out using a reverse primer (IP11689; SEQ ID NO:7) designed on the EST cluster (within the area showing similarity to the NEP/ECE family) and a degenerated forward primer (IP11685; SEQ ID NO:8), centered on a conserved peptide motif (VNA(F,Y)Y) of the NEP/ECE family.

For the synthesis of cDNA 2 µg human lung total RNA (Clontech #64023-1), 1 µl oligo(dT)$_{12-18}$ (500 µg/ml) and 9 µl H$_2$O were combined (final volume=12 µl), heated to 70° C. for 10 minutes and then chilled on ice. 4 µl 5× first strand buffer (250 mM Tris-HCl pH 8.3, 375 mM KCl, 15 mM MgCl$_2$), 2 µl 0.1M DTT, 1 µl 10 mM dNTP mix and 1 µl (200 U) Superscript™ II (Life Technologies) reverse transcriptase were added. The mixture was incubated at 42° C. for 50 minutes and the reaction was inactivated by heating at 70° C. for 15 minutes.

The PCR reaction was performed in a 50 µl volume containing 1 µl of the cDNA synthesis reaction, 5 µl of GeneAmp™ 10×PCR buffer (500 mM KCl, 100 mM Tris pH 8.3, 15 mM MgCl$_2$, 0.01% (w/v) gelatin; Perkin Elmer), 2 µl of 10 mM dNTP mix, 10 pmoles each of the forward and reverse primers and 5 units AmpliTaq™ polymerase (Perkin Elmer). After an initial denaturation at 95° C. for 5 min., PCR reactions were cycled 40× as follows: 1 min denaturation at 94° C., 1 min annealing at 60° C. and 1 min extension at 72° C. PCR reaction products were analyzed by agarose gel electrophoresis.

The IP11685/IP11689 RT-PCR reaction produced an amplicon of ±600 base pairs (bp). The fragment was purified from gel using the Qiaex-II™ purification kit (Qiagen) and ligated into the pGEM-T Easy plasmid according to the procedure recommended by the supplier (pGEM-T Easy system, Promega). The recombinant plasmids were then used to transform competent E. coli SURE™ 2 bacteria (Stratagene). Transformed cells were plated on LB agar plates containing ampicillin (100 µg/l), IPTG (0.5 mM) and X-gal (50 µg/ml). Plasmid DNA was purified from minicultures of individual colonies using the BioRobot™ 9600 nucleic acid purification system (Qiagen).

DNA Sequencing reactions were carried out on the purified plasmid DNA with the ABI Prism™ BigDye™ Terminator Cycle Sequencing Ready Reaction kit (PE-ABI), using insert-flanking or internal (IGS5 specific) primers. Plasmid inserts were completely sequenced on both strands. Cycle Sequencing reaction products were purified via EtOH/NaOAc precipitation and analyzed on an ABI 373 automated sequencer. The DNA sequence of the inserts of recombinant clones YCE14, YCE15 and YCE16 (derived from the IP11685/IP11689 amplicon) extended the open reading frame of the original EST cluster in the direction of the N-terminus and further confirmed that this open reading frame was derived from a novel member of the NEP/ECE metalloprotease protein family (see FIG. 1). This upstream sequence thus deviated completely from the upstream sequence present in the EST sequences. This novel sequence is referred to within the context of the present invention generally as "IGS5."

EXAMPLE 1b

Cloning of cDNA Containing the Putative Ectodomain of IGS5

In order to obtain additional IGS5 cDNA sequence another round of RT-PCR reactions were carried out on human lung RNA under the conditions described above using the IGS5 specific reverse primer IP12190 (SEQ ID NO:9) and a degenerated forward primer (IP12433; SEQ ID NO:10), centered on a conserved peptide motif (LXXLX-WMD) of the NEP/ECE family. The IP12190/12433 RT-PCR reaction produced an amplicon of ±600 bp that was cloned into the pGEM-T Easy vector yielding clones YCE19, YCE22 and YCE23. All clones were fully sequenced and allowed to extend the IGS5 open reading frame further upstream (see FIG. 1).

To obtain cDNA clones that would cover the 5' end of the IGS5 transcript, semi-nested 5'-RACE PCR reactions were done on human heart Marathon-Ready™ cDNA using the adaptor primer 1 (AP1: SEQ ID NO:11) provided with the Marathon™ cDNA amplification kit (Clontech K1802-1) in combination with IGS5 specific primers IP12189 SEQ ID NO:12) and IP12585 (SEQ ID NO:13). PCR RACE reactions were performed according to the instructions of the Marathon-Ready™ cDNA user manual provided by Clontech. RACE products were separated on agarose gel, visualized with ethidium bromide and blotted onto Hybond N+ membranes. Blots were prehybridized at 65° C. for 2 h in modified Church buffer (0.5 M phosphate, 7% SDS, 10 mM EDTA) and then hybridized overnight at 65° C. in the same buffer containing 2×10$^6$ cpm/ml of the $^{32}$P-labelled insert of clone YCE23. The YCE23 insert was radiolabelled via random primed incorporation of ($\alpha$-$^{32}$P)dCTP to a specific activity of >10$^9$ cpm/μg using the Prime-It II kit™ (Stratagene) according to the instructions provided by the supplier. Hybridized blots were washed at high stringency (2×30 min at room temperature in 2×SSC/0.1% SDS followed by 2 washes of 40 min at 65° C. in 0.1×SSC, 0.1% SDS) and autoradiographed overnight. Hybridizing fragments were purified from gel, cloned into the PGEM-T Easy vector (yielding clones YCE 59, YCE 64 and YCE 65) and sequenced as described above.

The DNA sequences of all isolated clones could be assembled into a single contig (IGS5CONS; see FIG. 1) that extended the open reading frame of IGS5 further upstream but an ATG start of translation codon was not yet encountered. Primer IP11689 had been designed on EST AI380811 and did not contain the last 4 nucleotides before the stop codon present in the aligned EST sequences. In order to generate an open reading frame that terminated at the stop codon the last (consensus) 22 nucleotides of the aligned EST sequences were included in the overall assembly of IGS5CONS.

Figure 1:
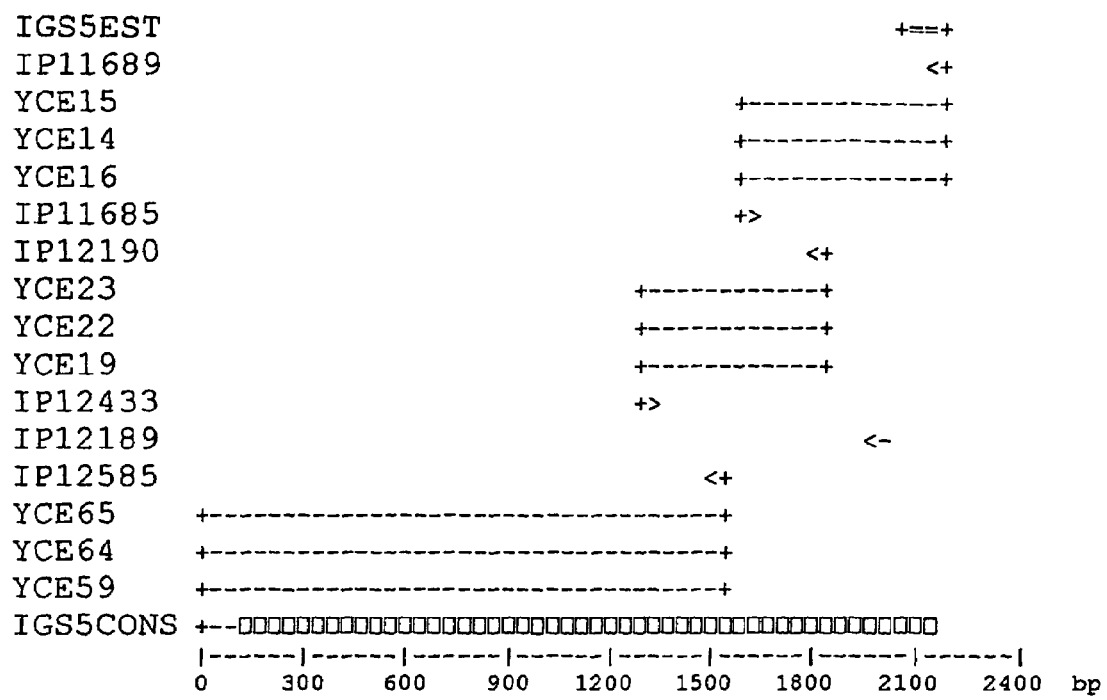
FIG. 1: Schematic representation of the relative positions of the different cDNA clones that were isolated and fully sequenced to generate the partial IGS5 consensus cDNA sequence. PCR primers that were used for 5' RACE and semi-homology PCR cloning are indicated and have been described in this document (indicated by the respective IP#). IGS5CONS denotes the consensus contig that was obtained after merging all obtained sequences. The 691 amino acids long open reading frame present in the IGS5 contig, that is postulated to contain the ectodomain of the IGS5 enzyme (IGS5DNA, IGS5PROT) is indicated with open boxes ("☐☐"). The part of the aligned EST sequences (accession no AA524283, AI088893, AI217369 and AI380811) that bears homology to members of the NEP/ECE family is indicated with "+==+" (IGS5EST). "bp"=base pairs.

Homology searches showed that the (partial) encoded protein was most similar to neutral endopeptidase (NEP; see example 2). However, the initial 20 amino acids of the IGS5CONS open reading frame did not show any similarity to NEP. This could possibly be due to the fact that they were derived from an intron. Indeed exon 4 of human NEP starts at a position that corresponds approximately to the position downstream of these 20 amino acids (D'Adamio L. et al. Proc. Natl. Acad. Sci. USA (1989) 86: 7103–7107). Hydropathy analysis (Kyte J. et al. (1982) J. Mol. Biol. 157: 105–132; Klein P. et al. (1985) Biochim. Biophys. Acta 815:468–476) did not indicate the presence of a transmembrane domain within the predicted IGS5CONS amino acid sequence, although such a transmembrane domain would be expected to occur (or at least overlap with) within the initial 20 amino acids. For these reasons it was preferred to exclude the initial sequence part of the IGS5 contig (FIG. 1). The resulting DNA sequence (IGS5DNA; SEQ ID NO:1) is 2076 nucleotides long (including the stop codon) and encodes a protein of 691 residues (IGS5PROT, SEQ ID NO:2). Alignment of IGS5PROT with the human NEP protein sequence showed that the IGS5PROT sequence corresponds to the complete ectodomain sequence of NEP. IGS5PROT can thus be expected to carry the complete enzymatic activity of the putative IGS5 enzyme, as was demonstrated for the ectodomain of NEP (Fossiez F. et al. Biochem. J. (1992) 284, 53–59).

TABLE 7

Overview of oligo primers used in Example 1

SEQ ID NO: 7 IP11689: 5'-ACACGGCATCGCTCCTTG-3'

SEQ ID NO: 8 IP11685: 5'-CCCCCTGGACGGTGAA (C or T) GC (A, C, G or T) T (A or T) (C or T) TA-3'

SEQ ID NO: 9 IP12190: 5'-AATCCGTTCACGTTCTGTTCGTCTGCC-3'

SEQ ID NO: 10 IP12433: 5'-CCTGGAGGAGCTG (A, C or G) (A, C or T) (A, C, G or T) TGGATG (A or G) A-3'

SEQ ID NO: 11 AP1:     5'-CCATCCTAATACGACTCACTATAGGGC-3'

SEQ ID NO: 12 IP12189: 5'-GTCCTTGCCACCCTCTGCCATCC-3'

SEQ ID NO: 13 IP12585: 5'-ACCACCCCGCCCCGATGATCCAGAG-3'

EXAMPLE 2

Alignment of IGS5 with Protein Sequences of Members of the NEP/ECE Metalloprotease Family For the IGS5 Sequence cloned in example 1a, homology searches of up to date protein databanks and translated DNA databanks were executed using the BLAST algorithm (Altschul S. F. et al. (1997), Nucleic Acids Res. 25:3389–3402). These searches showed that the IGS5 protein was most similar (54–55% identities over ±700 aligned residues) to mouse, rat and human neutral endopeptidase (SW: NEP_MOUSE, accession n° Q61391; SW:NEP_RAT, accession n° P07861 and SW:NEP_HUMAN accession n° P08473).

Thus, this alignment of the almost complete IGS5 protein sequence with the other members of the NEP/ECE family shows the relation of IGS5 to metalloproteases in general, and in particular to the NEP and/or ECE metalloprotease families. From this structural alignment it is concluded that the IGS5 has the functionality of metalloproteases, which in turn are of interest in the context of several dysfunctions, disorders or diseases in animals and humans.

EXAMPLE 3

The Cloning of cDNA Encoding a Novel Member of the NEP/ECE Metalloprotease Family EXAMPLE 3a Homology PCR cloning of a cDNA fragment of a novel member of the NEP/ECE metalloprotease family.

In the DNA databank of expressed sequence tags (ESTs) 4 overlapping EST sequences (accession nos. AA524283, AI088893, AI217369 and AI380811) were detected which contained a small open reading frame encoding a stretch of protein that showed similarity to the C-terminal part of members of the neutral endopeptidase 24.11/endothelin converting enzyme (NEP/ECE) metalloprotease protein family (Turner A. J. et al., Faseb J. (1997) 11: 355–364). The NEP/ECE-like small open reading frame in these ESTs was terminated by a stop codon (in the case of AA524283) and was preceded in all 4 ESTs by a sequence that contained stop codons in all 3 reading frames. This preceding sequence appeared totally unrelated to NEP/ECE metalloprotease family members. Although the polarity of the small open reading frame was opposite to the 5'->3' orientation of the mRNA from which these ESTs had been derived, it was decided to use these sequences as the basis for a RT-PCR homology cloning approach. In parallel, additional EST sequences, that showed the same structure as the 4 ESTs mentioned before were observed to appear in the public domain databanks, e.g. accession nos: AI825876, AI888306, AI422224, AI422225, AI469281, AA975272, AA494534, AW006103, AI827701, AI650385, AI827898, AI934499 and AA422157. The RT-PCR reactions were carried out using a reverse primer (IP11689; SEQ ID NO:7) designed on the EST cluster (within the area showing similarity to the NEP/ECE family) and a degenerated forward primer (IP11685; SEQ ID NO:8), centered on a conserved peptide motif (VNA(F,Y)Y) of the NEP/ECE family.

For the synthesis of cDNA 2 µg human lung total RNA (Clontech #64023-1), 1 µl oligo(dT)$_{12-18}$ (500 µg/ml) and 9 µl H$_2$O were combined (final volume=12 µl), heated to 70° C. for 10 minutes and then chilled on ice. 4 µl 5× first strand buffer (250 mM Tris-HCl pH 8.3, 375 mM KCl, 15 mM MgCl$_2$), 2 µl 0.1 M DTT, 1 µl 10 mM dNTP mix and 1 µl (200 U) Superscript™ II (Life Technologies) reverse transcriptase were added. The mixture was incubated at 42° C. for 50 minutes and the reaction was inactivated by heating at 70° C. for 15 minutes.

The PCR reaction was performed in a 50 µl volume containing 1 µl of the cDNA synthesis reaction, 5 µl of GeneAmp™ 10×PCR buffer (500 mM KCl, 100 mM Tris pH 8.3, 15 mM MgCl$_2$, 0.01% (w/v) gelatin; PE Biosystems), 2 µl of 10 mM dNTP mix, 10 pmoles each of the forward and reverse primers and 5 units AmpliTaq™ polymerase (PE Biosystems). After an initial denaturation at 95° C. for 5 min., PCR reaction tubes were cycled 40× as follows: 1 min denaturation at 94° C., 1 min annealing at 60° C. and 1 min extension at 72° C. PCR reaction products were analyzed by agarose gel electrophoresis.

The IP11685/IP11689 RT-PCR reaction produced an amplicon of ±600 base pairs (bp). The fragment was purified from gel using the Qiaex-II™ purification kit (Qiagen) and ligated into the pGEM™-T Easy plasmid according to the procedure recommended by the supplier (pGEM™-T Easy system, Promega). The recombinant plasmids were then used to transform competent E. coli SURE™ 2 bacteria (Stratagene). Transformed cells were plated on LB agar plates containing ampicillin (100 µg/ml), IPTG (0.5 mM) and X-gal (50 µg/ml). Plasmid DNA was purified from mini-cultures of individual colonies using the BioRobot™ 9600 nucleic acid purification system (Qiagen).

Figure 2:
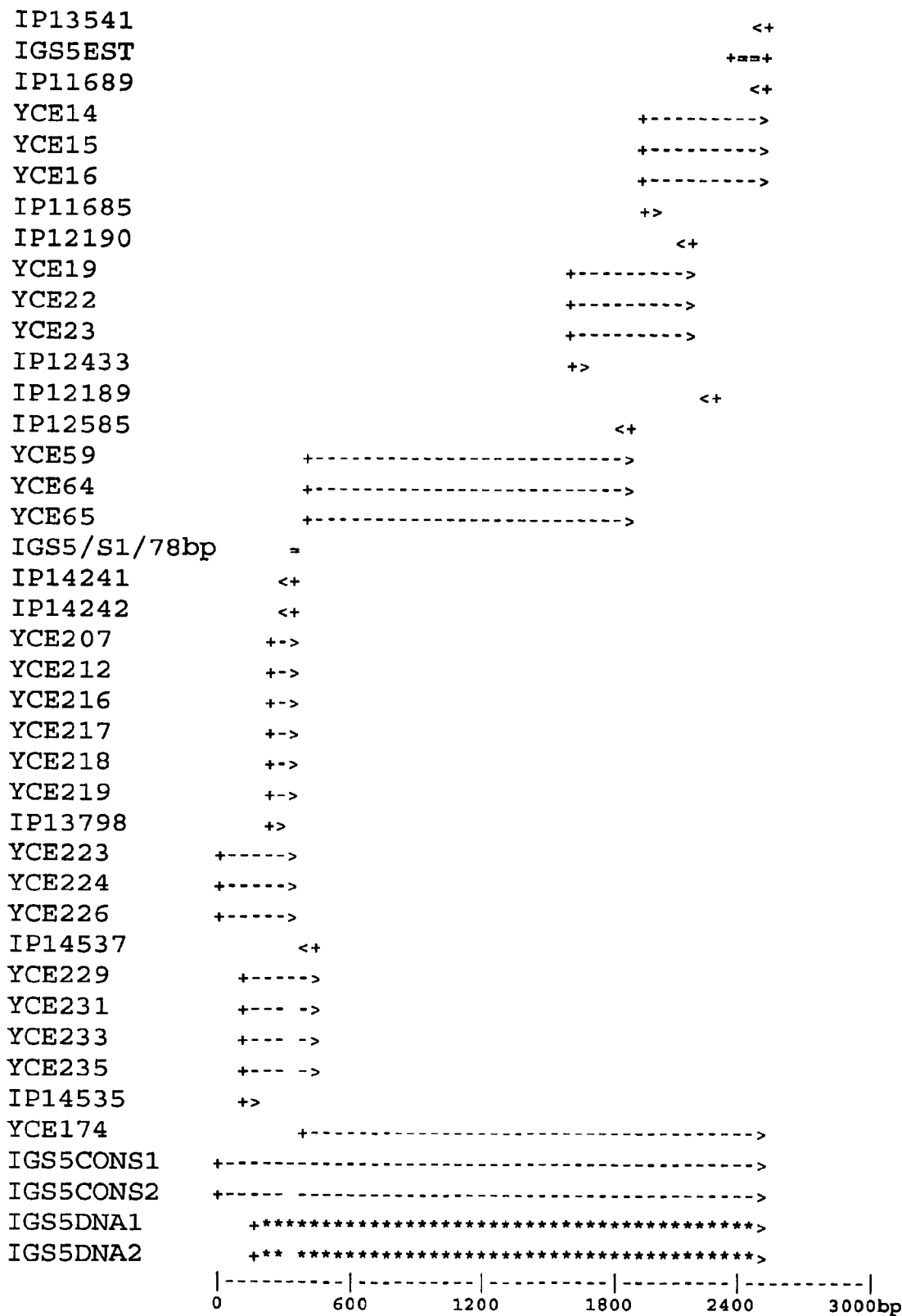
FIG. 2 Schematic representation of the relative positions of the different cDNA clones that were isolated and fully sequenced to generate the IGS5DNA1 and IGS5DNA2 cDNA sequences. PCR primers that were used for PCR, 5' RACE and semi-homology PCR cloning are indicated and have been described in this document (indicated by the respective IP#). IGS5CONS1 and IGS5CONS2 denote the 2 different consensus contigs that were obtained after merging all obtained sequences. IGS5DNA1 and IGS5DNA2 denote the open reading frames present in IGS5CONS1 and IGS5CONS2 respectively ("**") The part of the aligned EST sequences (accession n° AA524283, AI088893, AI217369 and AI 380811) that bears homology to members of the NEP/ECE family is indicated with "+==+" (IGS5EST). "bp"=base pairs. The 78 bp fragment identified within genomic clone IGS5/S1 is denoted as "IGS5/S1/78 bp." The absence of the 78 bp alternate exon sequence within clones YCE231, YCE233 and YCE235 and within IGS5CONS2 and IGS5DNA2 is indicated by a gap.

DNA sequencing reactions were carried out on the purified plasmid DNA with the ABI Prism™ BigDye™ Terminator Cycle Sequencing Ready Reaction kit (PE Biosystems), using insert-flanking or internal primers. Plasmid inserts were completely sequenced on both strands. Cycle Sequencing reaction products were purified via EtOH/NaOAc precipitation and analyzed on an ABI 377 automated sequencer. The DNA sequence of the inserts of recombinant clones YCE14, YCE15 and YCE16 (derived from the IP11685/IP11689 amplicon) extended the open reading frame of the original EST cluster in the direction of the N-terminus and further supported the hypothesis that this open reading frame was derived from a novel member of the NEP/ECE metalloprotease protein family (FIG. 2). This upstream sequence thus deviated completely from the upstream sequence present in the EST sequences. This novel sequence is referred to within the context of the present invention generally as "IGS5."

EXAMPLE 3b

Cloning of cDNA Fragments Containing the Full Length Coding Sequence of IGS5

In order to obtain additional IGS5 cDNA sequence another round of RT-PCR reactions were carried out on human lung RNA under the conditions described above using the IGS5 specific reverse primer IP12190 (SEQ ID NO:9) and a degenerated forward primer (IP12433; SEQ ID NO:10), centered on a conserved peptide motif (LXXLX-WMD) of the NEP/ECE protein family. The IP12190/12433 RT-PCR reaction produced an amplicon of ±600 bp that was cloned into the pGEM™-T Easy vector yielding clones YCE19, YCE22 and YCE23. All clones were fully sequenced and allowed to extend the IGS5 open reading frame further upstream (see FIG. 2).

To obtain cDNA clones that would cover the 5' end of the IGS5 transcript, semi-nested 5'-RACE PCR reactions were done on human heart Marathon-Ready™ cDNA using the adaptor primer 1 (AP1: SEQ ID NO:11) provided with the Marathon™ cDNA amplification kit (Clontech K1802-1) in combination with IGS5 specific primers IP12189 (SEQ ID NO:12) and IP12585 (SEQ ID NO13). PCR RACE reactions were performed according to the instructions of the Marathon-Ready™ cDNA user manual provided by Clontech. RACE products were separated on agarose gel, visualized with ethidium bromide and blotted onto Hybond™-N$^+$ membranes (Amersham). Blots were prehybridized at 65° C.

for 2 h in modified Church buffer (0.5 M phosphate, 7% SDS, 10 mM EDTA) and then hybridized overnight at 65° C. in the same buffer containing 2×10⁶ cpm/ml of the $^{32}$P-labelled insert of clone YCE23. The YCE23 insert was radiolabelled via random primed incorporation of (α-$^{32}$P) dCTP to a specific activity of >10⁹ cpm/μg using the Prime-It II kit™ (Stratagene) according to the instructions provided by the supplier. Hybridized blots were washed at high stringency (2×30 min at room temperature in 2×SSC/0.1% SDS followed by 2 washes of 40 min at 65° C. in 0.1×SSC, 0.1% SDS) and autoradiographed overnight. Hybridizing fragments were purified from gel, cloned into the pGEM™-T Easy vector (yielding clones YCE 59, YCE 64 and YCE 65) and sequenced as described above.

The DNA sequences of all isolated clones could be assembled into a single contig that extended the open reading frame of IGS5 further upstream although no start of translation codon was yet encountered. Primer IP11689 had been designed on EST AI380811 and did not incorporate the last 4 nucleotides before the stop codon present in the aligned EST sequences. In order to generate an open reading frame that terminated at this stop codon the last (consensus) 22 nucleotides of the aligned EST sequences were included in the contig.

Several attempts to clone the still missing amino-terminal part of the IGS5 coding sequence via 5' RACE PCR extension or via screening of cDNA libraries failed. Therefore it was tried to obtain genomic sequence information in the area around and upstream of the 5' end of the preliminary IGS5 contig. Approximately 550,000 plaques of a human genomic DNA library, constructed in the lambda EMBL3 phage vector (Clontech HL1067j) were lifted onto Hybond™-N⁺ membranes. Membrane lifts were prehybridized at 65° C. for 2 h in modified Church buffer and then hybridized overnight at 65° C. in the same buffer containing 2×10⁶ cpm/ml of a $^{32}$P-labeled ±150 bp EcoRI/EcoRII fragment, located at the 5' end of clone YCE59. The cDNA probe was radiolabelled via random primed incorporation of (α-$^{32}$P) dCTP to a specific activity of >10⁹ cpm/μg using the Prime-It II kit™ (Stratagene) according to the instructions provided by the supplier. Hybridized membranes were washed at high stringency (2×30 min at room temperature in 2×SSC/0.1% SDS followed by 1 wash of 40 min at 65° C. in 0.1×SSC/0.1% SDS) and autoradiographed. Hybridizing plaques were subjected to a second round of screening and pure single plaques were obtained. Recombinant phage DNA was purified from infected liquid cultures using the Qiagen™ Lambda Midi Kit (Qiagen) and sequenced as described above using flanking EMBL3 vector primers and IGS5 internal primers. From the insert of clone IGS5/S1 approximately 5,000 nucleotides upstream of the 5' end of the preliminary IGS5 contig were sequenced. Homology searches of translated DNA databanks showed that this 5,000 bp fragment contained a stretch of 78 bp which encoded a peptide that was most similar (15 identical residues over 25 aligned) to an alternatively spliced 69 bp fragment in the mouse SEP sequence (GenBank accession no AF157105), which is a recently described novel member of the NEP/ECE family (Ikeda et al. (1999) JBC 274: 32469–32477). This 78 bp human fragment was preceded by and followed by putative consensus splice acceptor and donor sites respectively but did not contain an "ATG" start of translation codon.

In order to obtain cDNA clones containing the amino-terminal part of the IGS5 coding sequence, semi-nested 5' RACE PCR reactions were carried out on human testis Marathon-Ready™ cDNA (Clontech 7414-1) using the adapter primer 1 (AP1: SEQ ID NO:11) provided with the Marathon™ cDNA amplification kit (Clontech K1802-1) in combination with IGS5 specific anti-sense primers IP14,241 (SEQ ID NO:14) and IP14242 (SEQ ID NO:15) which were designed within the 78 bp genomic fragment described above. PCR RACE reactions were performed according to the instructions of the Marathon Ready™ cDNA user manual provided by Clontech (reaction volume=25 μl). RACE products were separated on agarose gel, visualised with ethidium bromide and analyzed via Southern blot.

To generate a specific hybridizaton probe for the blotted RACE products, a semi-homology PCR reaction was carried out on the above obtained nested RACE products using the reverse oligonucleotide primer IP14241 (SEQ ID NO:14) and a degenerated forward primer (IP13798; SEQ ID NO:16) which was centered on a peptide motif (GLMV-LLLL) within the transmembrane domain of the mouse SEP protein. The PCR reaction was performed in a 25 μl volume containing 1 μl of the semi-nested 5' RACE PCR reaction product, 2.5 μl of GeneAmp™ 10×PCR buffer (500 mM KCl, 100 mM Tris pH 8.3, 15 mM MgCl₂, 0.01% (w/v) gelatin; PE Biosystems), 1 μl of 10 mM dNTP mix, 10 pmoles each of the forward and reverse primers and 2.5 units AmpliTaq-Gold™ polymerase (PE Biosystems). After an initial denaturation at 95° C. for 10 min, PCR reaction tubes were cycled 35× as follows: 1 min denaturation at 95° C., 30 seconds annealing at 50° C. and 30 seconds extension at 72° C. PCR reaction products were analyzed via agarose gel electrophoresis. The semi-homology PCR reaction produced an amplicon of ±110 base pairs. The fragment was purified from gel using the Qiaex-II™ purification kit (Qiagen) and ligated into the pGEM™-T plasmid according to the procedure recommended by the supplier (pGEM™-T system, Promega). The recombinant plasmids were then used to transform competent E. coli SURE™ 2 bacteria (Stratagene). Transformed cells were plated on LB agar plates containing ampicillin (100 μg/l), IPTG (0.5 mM) and X-gal (50 μg/ml). Plasmid DNA was purified from mini-cultures of individual colonies using the BioRobot™ 9600 nucleic acid purification system (Qiagen) and sequenced as described above. The DNA sequence of the inserts of recombinant clones YCE207, YCE212, YCE216, YCE217, YCE218 and YCE219 could be assembled with the 78 bp genomic fragment described above into a single contig (see FIG. 2).

Southern blots of the semi-nested 5' RACE PCR reaction products were prehybridized at 65° C. for 1 h in modified Church buffer and then hybridized overnight at 65° C. in the same buffer containing 2×10⁶ cpm/ml of the $^{32}$P-labelled insert of clone YCE207. Hybridized blots were washed at high stringency and autoradiographed. Hybridizing fragments were purified from gel, cloned into the pGEM™-T vector (yielding clones YCE223, YCE224 and YCE226) and sequenced as described above. The DNA sequences of these clones could be assembled with the 78 bp genomic fragment and with clones YCE207, YCE212, YCE216, YCE217, YCE218 and YCE219 into a single contig (FIG. 2). The resulting contig contained an open reading frame which started at an "ATG" initiation codon and encoded a protein which showed high similarity with the N-terminal sequence of the mouse SEP protein.

To obtain cDNA clones covering the amino-terminal part of the IGS5 coding sequence and overlapping with clone YCE59, PCR reactions were set up on human testis Marathon-Ready™ cDNA (Clontech 7414-1) using a specific forward primer (IP14535; SEQ ID NO:17) based on the 5' UTR sequence of IGS5 and a specific reverse primer (IP14537; SEQ ID NO:18) located within YCE59. The PCR reaction was performed in a 25 µl volume containing 2.5 µl of human testis Marathon-Ready™ cDNA, 2.5 µl of Gene-Amp™ 10×PCR buffer (500 mM KCl, 100 mM Tris pH 8.3, 15 mM MgCl$_2$, 0.01% (w/v) gelatin; PE Biosystems), 1 µl of 10 mM dNTP mix, 10 pmoles each of the forward and reverse primers and 2.5 units AmpliTaq-Gold™ polymerase (PE Biosystems). After an initial denaturation at 95° C. for 10 min., PCR reaction tubes were cycled 41× as follows: 1 min denaturation at 95° C., 1 min annealing at 53° C. and 1 min extension at 72° C. PCR reaction products were analysed by agarose gel electrophoresis. The PCR reaction produced two amplicons of ±300 and 380 base pairs respectively. The 300 bp and 380 bp fragments were purified from gel, cloned into the pGEM™-T vector and sequenced as described above. This yielded clones YCE231, YCE233 and YCE235 (300 bp fragment) and YCE229 (380 bp fragment).

Assembly of the DNA sequences of all isolated clones showed the presence of two types of cDNA sequences, that differed by the presence or absence of the 78 bp segment, inititially identified within genomic clone IGS5/S1. These two sequences likely originate from alternatively spliced RNA molecules. The longest transcript contains an open reading frame of 2337 nucleotides (encoding a protein of 779 residues) whereas the shorter transcript contains an open reading frame of 2259 nucleotides (encoding a protein of 753 residues). We refer to the coding sequence and protein sequence of the long form as IGS5DNA1 (shown in SEQ ID NO:3, 2340 bp including the stop codon tag) and IGS5PROT1 (SEQ ID NO:4) respectively, whereas the coding sequence and protein sequence of the shorter form are referred to as IGS5DNA2 (shown in SEQ ID NO:5, 2262 bp including the stop codon tag) and IGS5PROT2 (SEQ ID NO:6) respectively. Downstream of the postulated methionine initiaton codon within IGS5DNA1 and IGS5DNA2 an additional in-frame methionine codon is present at codon position 10. Although we have opted for the first methionine codon as being the initiaton codon some (or even exclusive) initiation of translation at codon position 10 cannot be excluded, since both methionines appear to be within an equally favorable "Kozak" initiation of translation context (Kozak M., Gene (1999): 234: 187–208). Hydropathy analysis (Kyte J. et al., J. Mol. Biol. (1982) 157: 105–132; Klein P. et al., Biochim. Biophys. Acta (1985) 815: 468–476) of the IGS5PROT1 and IGS5PROT2 sequences showed the presence of a single transmembrane domain between residues 22 to 50. This indicates that IGS5PROT1 and IGS5PROT2 are type II integral membrane proteins and thus have a membrane topology similar to other members of the NEP/ECE protein family.

TABLE 8

Overview of the oligonucleotide primers that were used in Example 3.

SEQ ID NO: 7 IP11689: 5'-ACACGGCATCGCTCCTTG-3'

SEQ ID NO: 8 IP11685: 5'-CCCCCTGGACGGTGAA (C or T) GC (A, C, G or T) T (A or T) (C or T) TA-3'

SEQ ID NO: 9 IP12190: 5'-AATCCGTTCACGTTCTGTTCGTCTGCC-3'

SEQ ID NO: 10 IP12433: 5'-CCTGGAGGAGCTG (A, C or G) (A, C or T) (A, C, G or T) TGGATG (A or G) A-3'

SEQ ID NO: 11 AP1:     5'-CCATCCTAATACGACTCACTATAGGGC-3'

SEQ ID NO: 12 IP12189: 5'-GTCCTTGCCACCCTCTGCCATCC-3'

SEQ ID NO: 13 IP12585: 5'-ACCACCCCGCCCCGATGATCCAGAG-3'

SEQ ID NO: 14 IP14241: 5'-ACAGCCGGCTAGCAAGGCGTGGCAGCTG-3'

SEQ ID NO: 15 IP14242: 5'-ACGACAGCCGGCTAGCAAGGCGTGGCAG-3'

SEQ ID NO: 16 IP13798: 5'-GG (A, C, G or T) CT (C or G) ATGGT (A, C, G or T) CT (C or G) CT (C or G) CT (C or G) CT (C or G)-3'

SEQ ID NO: 17 IP14535: 5'-CTCCTGAGTGAGCAAAGGTTCC-3'

SEQ ID NO: 18 IP14537: 5'-GCAAACTGGTAGAAGTCGTCACAC-3'

EXAMPLE 4

Alignment of IGS5 with Protein Sequences of Members of the NEP/ECE Metalloprotease Family For the IGS5 sequence cloned in example 3, homology searches of up to date protein databanks and translated DNA databanks were executed using the BLAST algorithm (Altschul S. F. et al, Nucleic Acids Res. (1997) 25:3389–3402). These searches showed that IGS5PROT1 was most similar (76% identities over 778 aligned residues) to mouse SEP (GenBank accession n° AF157105) and also showed 54–55% identities over 696 aligned residues to mouse, rat and human neutral endopeptidases (SW:NEP_MOUSE, accession n° Q61391; SW:NEP_RAT, accession n° P07861; SW:NEP_HUMAN, accession n° P08473). Homology searches of IGS5PROT2 showed that this sequence was most similar (78% identities over 752 aligned residues) to mouse SEP □ (GenBank accession no AF157106). In analogy with the mouse SEP and SEP □ proteins it is to be expected that IGS5PROT1 and IGS5PROT2 represent the membrane-bound and soluble forms of the IGS5 protein respectively. This is corroborated by the presence of dibasic residues (KRK) encoded at the 3' end of the the alternatively spliced 78 bp exon.

Thus, this alignment of the complete IGS5 protein sequence with the other members of the NEP/ECE family shows the relation of IGS5 to NEP/ECE metalloproteases in general, and in particular to the SEP and NEP family members. From this structural alignment it is concluded that the IGS5 protein has the functionality of metalloproteases, which in turn are of interest in the context of several dysfunctions, disorders or diseases in animals and humans.

EXAMPLE 5

RNA Expression Analysis of IGS5

IGS5 expression analysis on Human RNA Master Blot™. A solution of Express-Hyb™ (Clontech #8015-1) and sheared salmon testis DNA was prepared as follows: 15 ml of Express-Hyb was preheated at 50–60° C. 1.5 mg of sheared salmon testis DNA was heated at 95° C. for 5 minutes and then quickly chilled on ice. The heat-denatured sheared salmon testis DNA was mixed with the preheated Express-Hyb™. The human RNA Master Blot™ (Clontech #7770-1) was prehybridised in 10 ml of the solution prepared above for 30 minutes with contiguous agitation at 65° C. The $^{32}$P labelled YCE15 probe (labelled with Prime-it II™ kit, Stratagene) was heat-denatured and added to the remaining 5 ml of the Express-Hyb™ solution. Hybridisation was done overnight at 65° C. Washings were done in 2×SSC/1% SDS for 100 minutes (5×20 min.) at 65° C. Two additional 20 minutes washes were performed in 200 ml 0.1×SSC/0.5% SDS at 55° C. Finally the Master Blot was autoradiographed using X-ray film.

Figure 3:
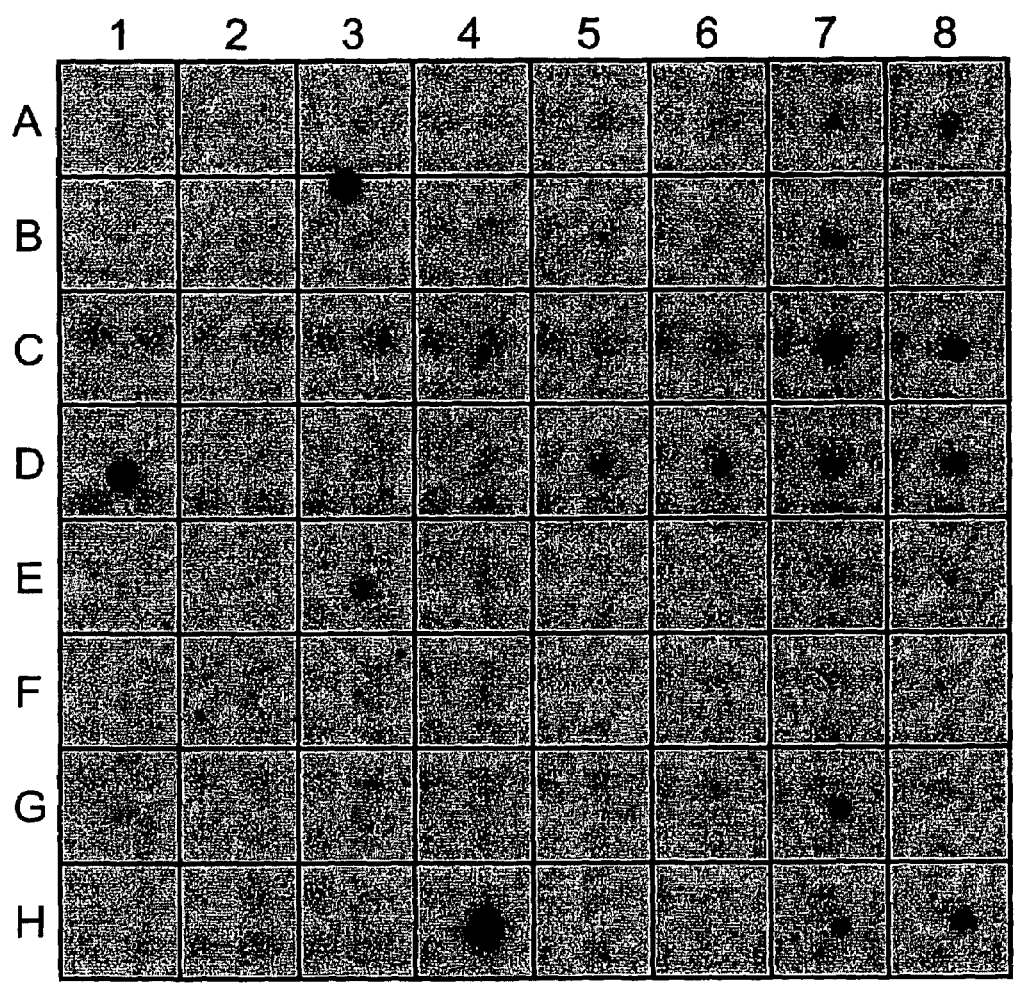
FIG. 3 RNA Master Blot™ analysis of the IGS5 gene.

Hybridization of the IGS5 probe on the Master Blot™ showed expression in a wide range of tissues, and in particular expression in testis, small intestine, prostate and stomach (FIG. 3).

IGS5 expression analysis on Human Brain Multiple Tissue Northern Blots II and IV (#7755-1 and #7769-1 respectively). An Express-Hyb™ solution (Clontech #8015-1) was preheated at 68° C. The blot was prehybridised at 68° C. for 1 hour. 100 µg sheared salmon testis DNA was added to the $^{32}$P labelled YCE15 probe (labelled with Prime-it II™ kit, Stratagene) and heat-denatured at 95° C. for 10 minutes. The probe was added to the remaining 5 ml of the Express-Hyb™ solution and hybridisation was done for 2 hours at 68° C. Washings were done in 2×SSC/0.05% SDS for 40 minutes (2×20 min.) at RT. Two additional 20 minutes washes were performed in 200 ml 0.1×SSC/0.1% SDS at 55° C. The blot was autoradiographed using X-ray film.

This Northern blot analysis showed a major hybridizing band of ±3 kb and a minor band of ±5.5–6 kb in all tissues investigated.

EXAMPLE 6

Expression and Purification of the His-Tagged Ectodomain of Human IGS5

The aim of the experiment was to produce soluble IGS5 protein using the baculoviral expression system. A recombinant baculovirus was constructed that expressed the $His_6$-tagged IGS5 ectodomain upon infection of the Sf9 cell-line. Soluble IGS5 protein was then purified from the culture supernatant in a two step procedure involving lentil-lectin and Zn-IMAC chromatography.

We fused the signal peptide of the pro-opiomelanocortin precursor (POMC) to the His-tagged extracellular part of the IGS5 coding sequence. As the enzymatically active site (metalloprotease) of the protein is located at the C-terminal end, we preferred to add the His-purification tag at the N-terminus of the protein. Furthermore a Gly-Ser linker was inserted between the POMC signal peptide and the IGS5 ectodomain. The expressed IGS5 protein started at residue 60 of IGS5PROT2 (SEVC . . . ) and thus comprised almost the complete IGS5 ectodomain. The cloning strategy involved a combination of synthetic oligonucleotide assembly, overlap PCR and 3-points-ligation. This resulted in the expression of a protein consisting of the POMC signal (cleaved upon secretion), a Gly-Ser linker, a His6 peptide and the IGS5 extracellular domain.

EXAMPLE 6a

Construction of the pAcSG2SOLhuIGS5His6 Baculo Transfer Vector.

For the construction of the pAcSG2SOLhuIGS5 baculo transfer vector the following DNA fragments were generated:

1. The pAcSG2 vector (BD PharMingen) was StuI/NotI digested. The 5527 bp fragment was extracted from agarose gel using the QiaExII extraction kit (Westburg) and dissolved in 30 µl 10 mM Tris-HCl pH8.5.
2. pGEMT clone YCE174 was assembled from clones YCE15, YCE22, YCE64 and YCE65 via a combination of PCR and restriction digestion/ligation. Primer IP13541, which in contrast to IP11689 did contain the last 4 nucleotides of the IGS5 coding sequence and the stop codon, was used in this procedure (Table 9). YCE174 therefore contained almost the complete coding region of the huIGS5 extracellular domain down to (and including) the stop codon (FIG. 2). YCE174 was XhoI/NotI digested resulting in a 3025 bp, a 1723 bp and a 448 bp fragment as shown by agarose gel electrophoresis. The 1723 bp fragment, containing the coding region for the huIGS5 ectodomain, was extracted from gel (QiaexII, Qiagen) and dissolved in 20 µl 10 mM Tris-HCl pH8.5.
3. A synthetic nucleic acid fragment (180 bp) containing a StuI recognition site at the 5' end, followed by the POMC signal sequence, a Gly-Ser linker, a His6 tag and 65 bp of the 5' end of the IGS5 ectodomain coding sequence was assembled by combining the oligonucleotides IP14165, IP14114, IP14115, IP14116, IP14117, IP14118, IP14119, and IP14120, followed by overlap PCR with primers IP14166 and IP14110 (Table 9; see also FIG. 4). The StuI site present in the natural POMC signal peptide coding sequence was removed by introducing a silent mutation (IP14115, nucleotide 30 G->A) at bp position 57.

TABLE 9

Overview of the oligonucleotide primers
that were used in Example 6.

SEQ ID NO: 19 IP14165:5'-GACAAGGCCTATTATGCCGAGATCGTGCTGCAGCCGCTCG-3'

SEQ ID NO: 20 IP14114:5'-AAGGCCAGCAACAGGGCCCCCGAGCGGCTGCAGCACGATC-3'

SEQ ID NO: 21 IP14115:5'-GGGGCCCTGTTGCTGGCCTTGCTGCTTCAAGCCTCCATGG-3'

SEQ ID NO: 22 IP14116:5'-GTGAGAACCGCCACGCACTTCCATGGAGGCTTGAAGCAGC-3'

SEQ ID NO: 23 IP14117:5'-AAGTGCGTGGCGGTTCTCACCATCACCACCATCACAGCGA-3'

SEQ ID NO: 24 IP14118:5'-AGCCAGGGGTGGTGCAGACCTCGCTGTGATGGTGGTGATG-3'

SEQ ID NO: 25 IP14119:5'-GGTCTGCACCACCCCTGGCTGCGTGATAGCAGCTGCCAGG-3'

SEQ ID NO: 26 IP14120:5'-GGGTCCATGTTCTGGAGGATCCTGGCAGCTGCTATCACGC-3'

SEQ ID NO: 27 IP14166:5'-GACAAGGCCTATTATG-3'

SEQ ID NO: 28 IP14110:5'-GGGTCCATGTTCTG-3'

SEQ ID NO: 29 IP14111:5'-AGCGAGGTCTGCAC-3'

SEQ ID NO: 30 IP14112:5'-GTAGATGATGTGCCG-3'

SEQ ID NO: 31 IP13541:5'-GCACTAGTCTTGGCTACCACACGCGGCATCGCTCCTTG-3'

A second PCR fragment (495 bp) was amplified from the clone YCE174 template using primers IP14111 and IP14112. The first and second PCR product share a 65 bp long overlapping region. By using a mixture of both PCR products as a template, an overlap PCR was performed with primers IP14166 and IP14112, generating a final 610 bp PCR fragment. This fragment was purified on a QiaQuick Spin Column (Qiagen), StuI.XhoI digested and the resulting 496 bp fragment was extracted from agarose gel (QiaexII).

The three DNA fragments (5527, 1723 and 496 bp) that were generated as described above, were combined in a ligation reaction. The ligation mixture was incubated overnight at 16° C. and used to transform competent DH5alphaF' cells. The transformed bacteria were plated on LB agar/ampicillin plates (100 µg/ml ampicillin). Plates were incubated overnight at 37° C. 30 random colonies were cultured in 5 ml LB medium supplemented with 100 µg/ml ampicillin. Plasmid DNA was prepared using the Biorobot™ 9600 Nucleic Acid Purification System (Qiagen) and screened via BamHI digestion. 7 clones that displayed the correct restriction pattern were further analyzed by XhoI, StuI, AlwNI, HindIII and HincII digestion and sequence analysis of the insert. One clone with the correct restriction pattern and expected insert sequence, was finally selected and deposited in the culture collection (strainlist) as ICCG4502. (This clone contains a silent mutation at bp position 878 (G->A) of the transfer vector.)

Figure 5:
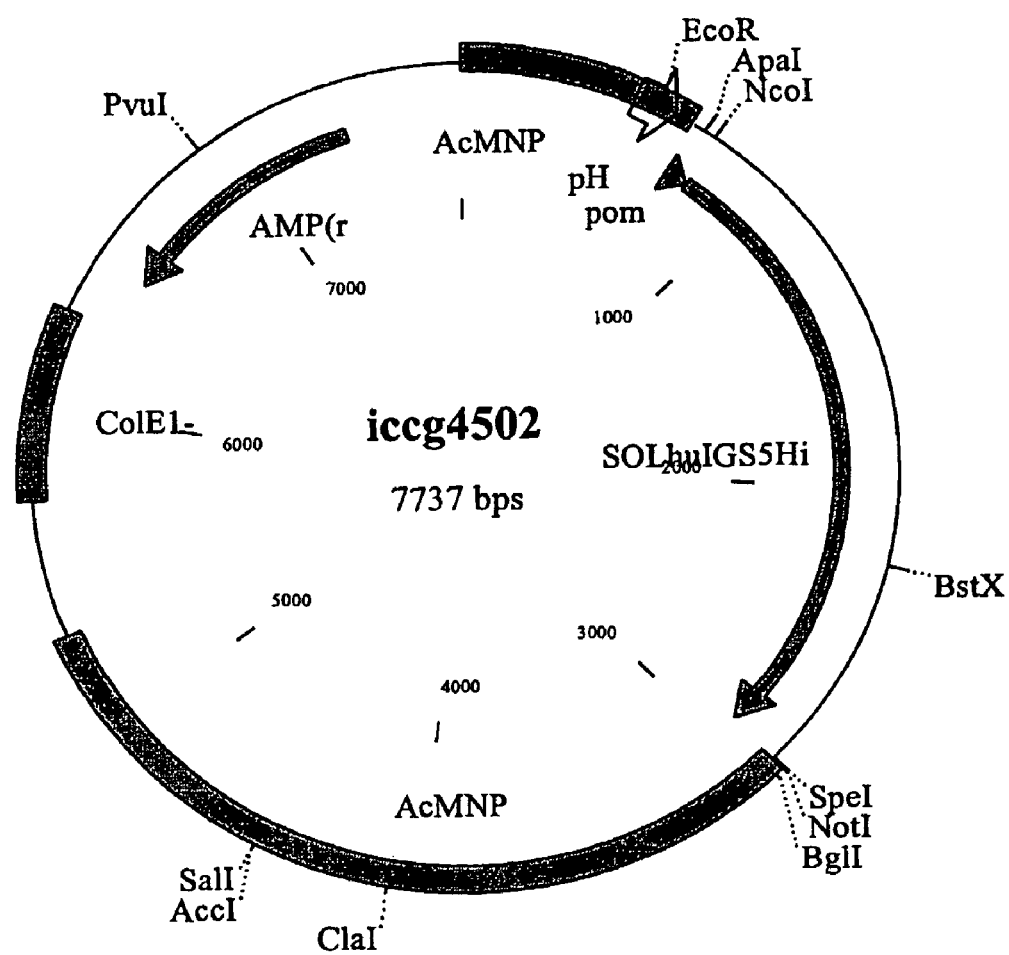
FIG. 5 Plasmid map of vector pAcSG2SOLhuIGS5His6.

A sterile Qiagen Midi DNA prep (Westburg) was made from the deposited clone, which yielded 110 µg DNA. Restriction analysis by XhoI, AlwNI, StuI, HindIII and HincII digestion revealed the correct restriction pattern as shown by agarose gel electrophoresis. Sequence analysis confirmed the expected sequence. The map of the pAcSG2SOLhuIGS5His6 baculo transfer vector is shown in FIG. 5.

EXAMPLE 6b

Generation of a Recombinant Baculovirus for Expression of Soluble huIGS5His6

A recombinant baculovirus, expressing the extracellular domain (minus a few AA) of the N-terminal His tagged human IGS5 was generated by cotransfection (Ca-phosphate transfection method) of the pAcSG2SOLhuIGS5His6 transfer vector DNA (ICCG 4502) in the host insect cell (*Spodoptera frugiperda* Sf9 cells) with the linearized genomic DNA of a modified version of the wild type baculoviral genome, (BaculoGold; Pharmingen catno 21100 D) in the host insect cells (*Spodoptera frugiperda* Sf9 cells). The BaculoGold DNA contains a lethal deletion and does not code for viable virus. Co-transfection of the BaculoGold DNA with a complementing Baculovirus transfer vector rescues the lethal deletion by homologous recombination. Using this approach 3 individual candidate recombinants were plaque-purified. All candidate recombinants were amplified.

EXAMPLE 6c

Eukaryotic Expression

Kinetic expression analysis. Sf9 cells (IGCL 83.0), exponentially growing in suspension in spinner flasks at 27° C. in TC100 medium (JRH Biosciences Catn° 56941), supplemented with 10% inactivated Foetal Calf Serum (Gibco BRL Catn° 10 084 168), were collected by low speed centrifugation and seeded at $5.10^5$ cells/Fk (25 cm$^2$) in serum-free TC100 medium. Candidate recombinant viral clones were added at a multiplicity of infection (MOI) of 3 pfu/cell and cell/virus cultures were subsequently incubated at 27° C. Conditioned medium (CM) was harvested at 24, 48 and 72 h post infection by 2 consecutive low speed centrifugations. Samples were analysed by SDS PAGE gel electrophoresis and Western blotting.

Western blot revealed a clear band at approximately 81 kDa in the CM of all candidate clones, corresponding to the theoretical Mr of the mature protein (81.2 kDa) (not shown). Expression levels of all 3 clones peaked at 48–72 h post-infection. Clone 2 was selected for further amplification and was deposited as IGBV73. Optimal harvest time was set at 72 h post infection.

Deglycosylation study. The soluble human IGS5 protein sequence contains 8 potential N-glycosylation sites (FIG. 6). Since the purification protocol involves binding of the sugar residues on a lentil-lectin column, samples of CM of all candidate recombinant viral clones, harvested at 72 h post infection, were used for a deglycosylation study with N-glycosidase F, to check whether the recombinant soluble His6IGS5 protein is indeed expressed as a glycosylated protein.

Samples were supplemented with SDS to a final concentration of 1% and incubated at 95° C. for 5'. After addition of 1 volume of the 2× incubation buffer (250 mM phosphate buffer, 50 mM EDTA, 5% N-octylglycoside, 1% 2-mercaptoethanol) and an additional 5' incubation time at 95° C., the sample was cooled to 37° C. 1 U of N-glycosidase F (Boehringer mannheim, catno 1 365 177) was added and after overnight incubation at 37° C., the sample was reduced with 100 mM DTT (final concentration).

Figure 7:
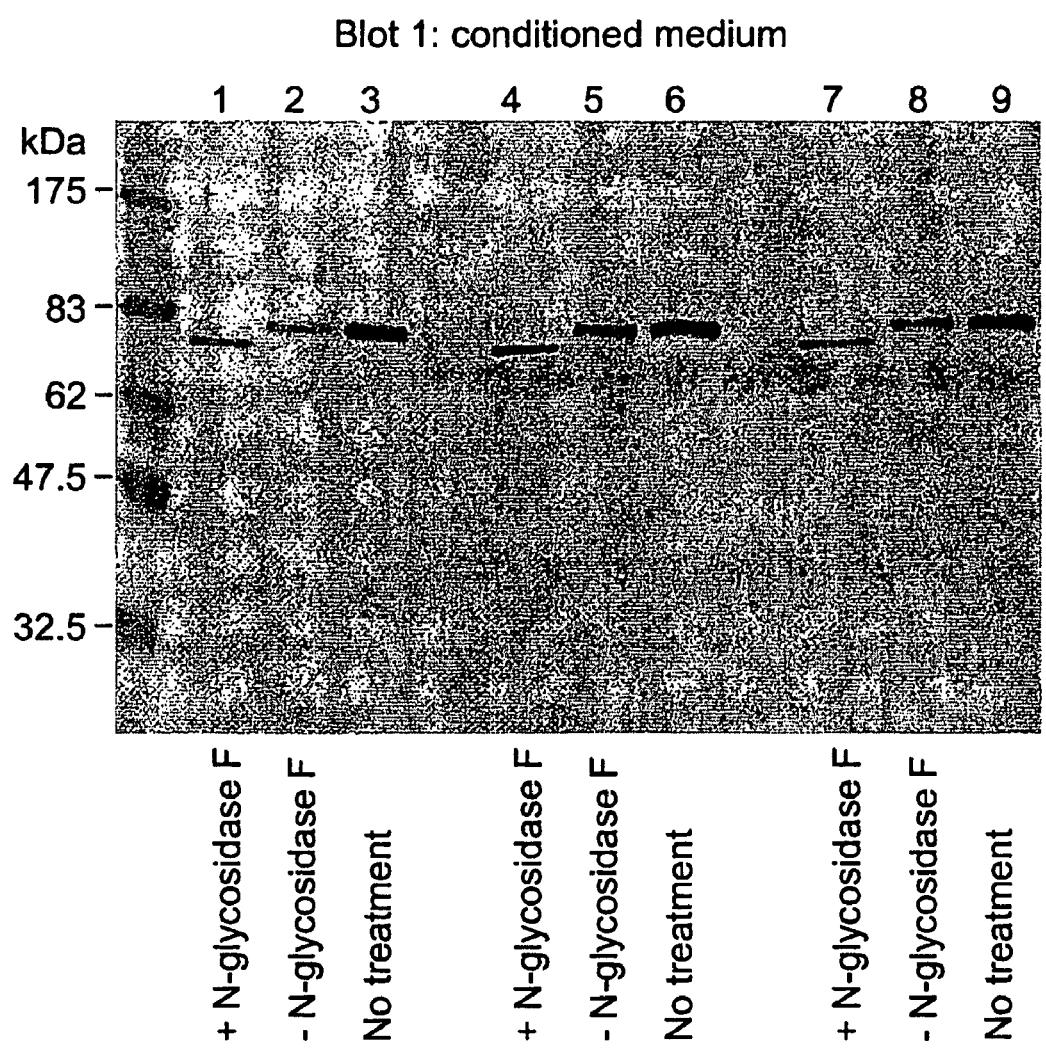
FIG. 7 Deglycosylation study—Western blot analysis. 72 h CM harvest of the infection with the 3 recombinant soluble His6IGS5 clones (clone 1: lanes 1 to 3, clone2: lanes 4 to 6, clone 3: lanes 7 to 9) was treated as described with and without addition of N-glycosidase F. 10 μl CM equivalent was loaded on gel versus 20 μl of the non-treated CM as a control.

Western blot analysis of N-glycosidase F treated CM samples and non-treated controls show a shift in Mr when samples are deglycosylated (FIG. 7), demonstrating that the soluble human His-tagged IGS5 is expressed as a glycosylated protein.

EXAMPLE 6d

Purification

Preparative production and sample pretreatment. Sf9 cells (IGCL 83-2) exponentially growing in suspension in spinner flasks at 27° C. in TC100 medium (JRH Biosciences, cat n° 56941) supplemented with 10% inactivated Foetal Calf Serum (Gibco BRL, cat n° 10 084 168) were collected by low speed centrifugation and resuspended at a density of $2.10^6$ cells/ml in TC100 medium, supplemented with 0.013 TIU aprotinin/ml (Pentex). Recombinant virus IGBV73 was added to the cells at a multiplicity of infection (MOI) of 2.25 pfu/cell. The cell/virus suspension was subsequently incubated at 27° C. in glass roller bottles (3×500 ml/1260 cm$^2$) for 72 h. The CM (1.5 l) was then cleared from cells and cell debris by two consecutive low speed centrifugations. 1 tablet of EDTA free complete (EFC; Roche biochemicals, cat n° 1873580) was added to 300 ml cleared Baculo CM. HEPES, glycerol and Tween 20 were added to a final concentration of resp. 20 mM, 5% (v/v) and 0.005% (w/v). The pH of the CM was adjusted to 7.4 and the sample was filtrated (Durapore Membrane Filters 0.2μ GV). All purification steps were performed at 4° C.

Lentil Lectin Chromatography. The baculo sample was loaded overnight at 0.3 ml/min on a 5 ml Lentil Lectin Sepharose resin in a C10/10 column (Pharmacia), which had been equilibrated in buffer A (20 mM Hepes, pH7.4, 150 mM NaCl, 5% glycerol, 0.005% Tween 20) supplemented with 1 tablet EFC/500 mL. The column was washed with equilibration buffer until the absorbance at 280 nm reached baseline level and the bound proteins were eluted at 1 ml/min by applying buffer A containing 0.5 M alfa-methylpyrrannoside. The column was regenerated by applying 100 mM acetate, 500 mM NaCl, pH 5.0. The elution and regeneration liquids were collected manually and the pools were analyzed by SDS-PAGE on 12.5% Phast gels (Pharmacia) and silver staining. Prestained markers (Gibco) were included as relative molecular weight (Mr) standard.

The major amount of proteins were retrieved in the flow through and an IGS5-candidate band with a Mr of about 85.000 was observed in elution pools 1–3 (FIG. 8). Western blot analysis of the lentil chromatography with the anti-His tag mab showed that the soluble hIGS5 protein (Mr ~85 000) is quantitatively bound to the Lentil Lectin resin and that the his-tagged protein is recovered over the whole elution peak, but mainly in pools 1 and 2 (FIG. 9). The Lentil lectin elution pools 1 and 2 were further processed on the Zinc-IMAC column (runs A and B).

Immobilized metal affinity chromatography (IMAC) and dialysis. 1 ml Chelating HiTrap (Pharmacia) was loaded with zinc ions as described by the manufacturer and equilibrated with buffer B (20 mM Hepes, 100 mM NaCl, 5% glycerol, 0.005% (w/v) Tween 20, pH 7.2). Lentil elution pools 1 and 2 were loaded separately at 0.5 ml/min on the HiTrap column (IMAC run A and IMAC run B). A blank run was included to compare the chromatographic absorbance profile. The column was washed with buffer B till baseline level and bound proteins were eluted by applying an imidazole step gradient (20, 50, 100 and 200 mM) in buffer B. Fractions were collected manually. The IMAC column was regenerated by applying 20 mM Hepes, 50 mM EDTA, 500 mM NaCl, pH 7.2. Elution and regeneration pools were analyzed by SDS-PAGE (12.5% Phast gels, Pharmacia) and silver staining. The 200 mM imidazole pool was transferred to a slide a-lyzer-cassette (MWCO 10.000, Pierce) and dialyzed overnight against buffer B (130 fold excess, no buffer refreshment). The amount of soluble IGS5 in the dialyzed pool was determined with the micro-BCA method (Pierce). BSA was included as reference. The dialyzed baculo IGS5 was biochemically characterized by (1) SDS-PAGE under reducing and non reducing conditions and (2) Western blot with an anti His-tag mAb (21E1B4, Innogenetics) followed by incubation with alkaline phosphatase labeled rabbit anti-mouse Ig (Dako) and detection with NBT/BCIP staining. The glycosilation status of the soluble IGS5 was verified by PGNase F treatment (BioRad).

SDS-PAGE analysis and silver staining showed that the bulk of contaminating proteins were eluted by applying the 20 mM and 50 mM imidazole step (FIG. 10). The hIGS5 protein was retrieved in the 100 mM and 200 mM imidazole elution steps. The 85 kDa band in the 200 mM imidazole pool is a single band on the SDS-PAGE, which reacts with the anti his-tag mAb (FIG. 9). Silver staining did not reveal any difference in purity between the hIGS5 material obtained from IMAC run A and run B. Starting from 300 ml of baculo CM, 340 μg of over 95% pure his-tagged hIGS5 ectodomain was obtained by the 2 step purification procedure (i.e. a yield of about 1 mg/L).

The 200 mM imidazole Zn-IMAC pool was after SDS-PAGE blotted on PVDF membrane and the proteins were visualised by amido black staining. The PVDF bands were successively washed with 20% acetonitrile, and 20% methanol and dried. Amino-terminal sequencing was performed by Edman degradation using a Procise™ 492A (Applied biosystems) according to the manufacturer's description. Amino terminal sequencing confirmed that the Baculo IGS5 is recovered in the 85 kDa protein band.

EXAMPLE 7

Enzyme Inhibition Assay

The enzymatic activity of IGS5 polypeptides of the invention was tested with regard to the metabolism of biologically active peptides. In particular it was tested whether these IGS5 polypeptides may act on a variety of vasoactive peptides known in the state of the art such as atrial natriuretic peptide (ANP), bradykinin, big endothelin (Big ET-1), endothelin (ET-1), substance P and angiotensin-1. In the context of the present invention in particular it was tested whether the IGS5 ectodomain, which is a novel human metalloprotease, hydrolyzes said vasoactive peptides. For comparison the assay was also performed for a known member of the metalloprotease family which was described earlier as soluble secreted endopeptidase (SEP) by Emoto et al. (J. Biol. Chem., Vol. 274 (1999): pp. 32469–32477). Furthermore, it was tested whether the activity of IGS5 to convert a Big-ET-1 analogue (the so-called 17 aa Big-ET) may be inhibited by reference compounds that are used to determine the inhibition properties with regard to enzymes having ECE and/or NEP-characteristics. Compounds used to test the inhibition of IGS5-activity on the Big-ET-1 analogue were the compound phosphoramidon which inhibits endopeptidases like NEP and ECE, the compound thiorphan which specifically inhibits NEP, and the compound CGS-35066 which is a selective ECE inhibitor.

EXAMPLE 7a

Materials

Enzyme: IGS-5 (sol hu)(his)6; or: His6-tagged IGS5 ectodomain;
  stock solution: 53 mg/ml in 20 mM HEPES pH 7.2, 5% glycerol, 0.005% Tween20, 100 mM NaCl, purity>99%; storage at 4° C.
  working solution: stock solution diluted with assay buffer to 10 mg/ml.

Substrate:
Mca-Asp-Ile-Ala-Trp-Phe-Dpa-Thr-Pro-Glu-His-Val-Val-Pro-Tyr-Gly-Leu-Gly-COOH;

Fluorescence-quenched Big-ET-1 analogue;
  Mca=(7-Methoxycoumarin-4-yl);
  Dpa=(3-(2,4-Dinitrophenyl)-L-2,3-diaminopropionyl;
  stock solution: 100 µM in assay buffer; storage at −20° C. (commercially available from supplier: Polypeptide Laboratories, Wolfenbüttel, Germany)
Assay buffer: 100 mM Tris pH 7.0, 250 mM NaCl.

All test compounds were dissolved in DMSO at 10 mM and were further diluted with assay buffer.

EXAMPLE 7b

Assay Procedure

A quantity of 70 µl of the assay buffer, of 10 µl enzyme working solution and of 10 µl test compound solution were mixed in an Eppendorf vial and preincubated at 37° C. for 15 minutes. Then, 10 µl substrate stock solution was added and the reaction mixture was incubated at 37° C. for 60 minutes to allow for enzymatic hydrolysis. Subsequently the enzymatic reaction was terminated by heating at 95° C. for 5 minutes. After centrifugation (Heraeus Biofuge B, 3 min) the supernatant was subjected to HPLC analysis.

EXAMPLE 7c

HPLC Procedure

In order to separate the remaining substrate from the cleavage products reversed phase HPLC technique was used with a CC 125/4 Nucleosil 300/5 $C_{18}$ RP column and a CC 8/4 Nucleosil 100/5 C18 precolumn (commercially available from Macherey-Nagel, Duren, Germany). Thus, 60 µl of the reaction samples obtained in Example 7b were injected into the HPLC, and the column was eluted at a flow rate of 1 ml/min by applying the following gradient and solutions:

| Solution A: 100% | $H_2O$ + 0.5 M $H_3PO_4$, pH = 2.0 |
|---|---|
| Solution B: 100% | acetonitrile + 0.5 M $H_3PO_4$ |

| 0–2 min | 20% | B |
| 2–6 min | 20–60% | B |
| 6–8 min | 60% | B |
| 8–10 min | 60–90% | B |
| 10–13 min | 90% | B |
| 13–15 min | 90–100% | B |

Peptides were detected by absorbance at 214 nm and by fluorescence with an excitation wavelength of 328 nm and an emission wavelength of 393 nm.

EXAMPLE 7d

Calculations

The increasing fluorescence signal of the HPLC-peak of the peptide with the unquenched Mca-fluorophor after hydrolysis was taken as the basis for any calculation.

This signal was compared for the samples with and without inhibitor and % inhibition was calculated on basis of the respective peak areas.

$$\% \ inhib = 100 * (1 - A_{inhib}/A_{control})$$

All samples were run in duplicate and mean values were used.

A standard inhibitor (10 nM and 100 nM Phosphoramidon) and a solvent control (0.1%) was added to each assay run.

EXAMPLE 7e

Results

With regard to the IGS5 polypeptides of the present invention the results of Example 7 show that these IGS5 metalloprotease polypeptides hydrolyze in vitro a variety of vasoactive peptides known in the state of the art, in particular such as Big ET-1, ET-1, ANP and bradykinin. The results of the hydrolysis assay in comparison to the activity of SEP are shown in Table 10. From these results it is concluded that IGS5 may be particularly involved in the metabolism of said biologically active peptides.

TABLE 10

Hydrolysis of vasoactive peptides by IGS5 polypeptides in comparison to SEP (soluble secreted endopeptidase).

| Vasoactive Peptide | % Hydrolysis by IGS5 Polypeptide Conditions: 100 µg IGS5 polypeptide; 0.5 µM substrate; 2 h, 37° C. | % Hydrolysis by SEP (Emoto et al.) Conditions: 10 µg SEP; 0.5 µM substrate; 12 h, 37° C. |
|---|---|---|
| ANP | 5 (80*) | >95 |
| Bradykinin | 100 (62**) | >95 |
| Big ET-1 | (?)*** | 42 |
| ET-1 | 30 | 92 |
| Substance P | n.d. | >95 |
| Angiotensin 1 | n.d. | >95 |
| 17 aa Big ET | 41 | n.d. |

*500 µg IGS5 polypeptide
**10 µg IGS5 polypeptide
***activity was detected, but could not be quantified due to problems with the HPLC-detection Furthermore, the results of the experiments with reference compounds for inhibition of ECE- and/or NEP-activity show that the activity of IGS5 metalloprotease polypeptides of the present invention to convert the Big-ET-1 analogue 17 aa Big-ET is inhibited by phosphoramidon, a reference compound for ECE/NEP-inhibition, but IGS5 is not efficiently inhibited by the NEP-inhibitor thiorphan. These results are shown in Table 11. IGS5 polypeptides are also not inhibited by the selective ECE-inhibitor CGS-35066, a potent and selective non-peptidic inhibitor of endothelin-converting enzyme-1 with sustained duration of action. (De Lombart et al., J. Med. Chem. 2000, Feb. 10; 43(3):488–504).

TABLE 11

Inhibition of IGS5 polypeptide's activity to convert the Big-ET-1 analogue 17 aa Big-ET.

| Inhibitor Compound | $IC_{50}$ nM |
|---|---|
| Phosphoramidon | 18 |
| Thiorphan | >1000 |
| CGS-35066 | 1300 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

We claim:

1. An isolated polynucleotide selected from the group consisting of polynucleotides that remain hybridized with the complement of SEQ ID NO: 1, SEQ ID NO: 3 or SEQ ID NO: 5 in 0.1×SSC at 65° C. and encode a polypeptide with zinc metalloprotease activity, and polynucleotides complementary thereto.

2. A vector comprising a polynucleotide of claim 1 operatively linked with a regulatory element.

3. A vector according to claim 2, wherein the vector is an expression vector and the regulatory element is a promoter.

4. An isolated cell comprising the vector of claim 2.

5. A process for producing a polypeptide having a zinc metalloprotease activity, said process comprising culturing the cell of claim 4 under conditions suitable for the expression of said polypeptide and recovering the polypeptide.

6. A pharmaceutical composition comprising a compound selected from the group consisting of:
   (a) an isolated polynucleotide according to claim 1; and
   (b) a nucleic acid molecule complementary to SEQ ID NO:1, 2 or 5 that modulates the expression of the polynucleotide according to claim 1.

* * * * *